(12) United States Patent
Iacovitti et al.

(10) Patent No.: US 7,195,910 B2
(45) Date of Patent: Mar. 27, 2007

(54) HUMAN TYROSINE HYDROXYLASE PROMOTER AND USES THEREOF

(75) Inventors: Lorraine Iacovitti, Gwynedd Valley, PA (US); Mark Alexander Kessler, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 282 days.

(21) Appl. No.: 10/215,647

(22) Filed: Aug. 9, 2002

(65) Prior Publication Data

US 2003/0129170 A1 Jul. 10, 2003

Related U.S. Application Data

(63) Continuation-in-part of application No. 09/942,325, filed on Aug. 29, 2001, now abandoned.

(60) Provisional application No. 60/228,931, filed on Aug. 30, 2000.

(51) Int. Cl.
C12N 15/79 (2006.01)
C12N 15/12 (2006.01)
C07H 21/04 (2006.01)

(52) U.S. Cl. .................. 435/320.1; 536/24.1; 536/23.5

(58) Field of Classification Search .................. 514/44; 536/23.1, 24.1; 435/320.1

See application file for complete search history.

(56) References Cited

FOREIGN PATENT DOCUMENTS

| WO | WO 9740172 A | 10/1997 |
|---|---|---|
| WO | WO 9832879 | 7/1998 |
| WO | WO 0023571 A | 4/2000 |

OTHER PUBLICATIONS

Crystal RG. Science 270:404-410.1995.*
Verma IM and Somia N. Nature 389: 239-242. 1997.*
Anderson WF. Nature 392 (SUPP):25-30, 1998.*
Kmiec EB. American Scientist 87:240-247, 1999.*
Romano et al. Stem Cells 2000; 18:19-39.*
Verweij CL, Guidos C, Crabtree GR, Cell type specificity and activation requirements for NFAT-1 . . . , 1990, J Biol Chem 265:15788-15795.*
Romano G, Suon S, Jin H, Donaldson AE, Iacovitti L, Characterization of five evolutionary conserved regions of the human tyrosin hydroxylase (TH) promoter: . . . , 2005, J Cell Physiol 204:666-677.*
Sasaoka T, Kobayashi K, Nagatsu I, Takahashi R, Kimura M, Yokoyama T, Katsuki M, Nagatsu T, Analysis of the human tyrosine hydroxylase promoter-chloramphenicol acetyltranferase chimeric gene expression in trangenic mice, 1992, Mol Brain Res 16:274-286.*
Kessler MA, Yang M, Gollomp KL, Jin H, Iacovitti L, The human tyrosine hydroxylase gene promoter, 2003, Mol Brain Res 112:8-23.*

Kessler, M., et al. (2000), Society for Neurosci.(Abstract), 26(2):4-9.
Nagatsu, I., et al. (1994), J. Neural Transmission, 96:85-104.
Schimmel, J.J., et al. (1999), Mol. Brain Res., 74:1-14.
Sawamoto, K., et al. (2001), J. Neurosci., 21(11):3895-3903.
Bjorklund, A. and Stenevi, U. (1979) Brain Research, 177, 555-560.
McGeer, P.L., et al. (1988) Annals.of.Neurology, 24, 574-576.
Thomson, J.A., et al. (1998) Science, 282, 1145-1147.
Gage, F.H. (2000) Science, 287, 1433-1438.
Teitelman, G., et al. (1993) Development, 118, 1031-1039.
Holden, Constance (2002) Science, vol. 297, 500-502.
Aiuti, Alessandro, et al. (2002) Science, vol. 296, 2410-2413.
Bonner-Weir, Susan and Sharma, Arun (2002) Journal of Pathology, 197, 519-526.
Robertson, Paul R. M.D. (1992) The New England Journal of Medicine, vol. 327, No. 26, 1861-1868.
Iturriza, Fermin C. and Thibault Jean (1993) Neuroendocrinology, 57, 476-480.
Vogler, C. et al. (2001) Pediatric and Development Pathology, 4, 421-433.
Arenas, E. (2002) Brain Research Bulletin, vol. 57, No. 6, 795-808.
Sawamoto, Kazunobu et al. (2001) PNAS, vol. 98, No. 11, 6423-6428.
Kim, Ella L. et al. (1998) Nucleic Acids Research, vol. 26, No. 7, 1793-1800.
Altschul, S. F., Gish, W., Miller, W., Myers, E. W. and Lipman, D. J., Basic local alignment search tool, Journal of Molecular Biology, 215 (1990) 403-410.
Nuclear Receptors Nomenclature Committee, A unified nomenclature system for the nuclear receptor superfamily, Cell, 97 (1999) 161-163.
Aubin, J., Lemieux, M., Tremblay, M., Behringer, R. R. and Jeannotte, L., Transcriptional interferences at the Hoxa4/Hoxa5 locus: importance of correct Hoxa5 expression for the proper specificationof the axial skeleton, Developmental Dynamics, 212 (1998) 141-156.

(Continued)

Primary Examiner—Dave Trong Nguyen
Assistant Examiner—Patrick S. Riggins
(74) Attorney, Agent, or Firm—Nixon Peabody

(57) ABSTRACT

The present invention provides an isolated, purified and characterized human tyrosine hydroxylase (hTH) promoter nucleic acid sequence. The invention further provides a method of selecting TH positive (TH+) cells by preparing a construct comprising a hTH promoter operably linked to a heterologous nucleic acid sequence, for example, green fluorescent protein encoding sequence, and transfecting cells, particularly stem cells, with the construct. The invention also provides a hTH promoter, useful in gene therapeutic applications in driving therapeutic genes or other nucleic acid sequences operably linked to the hTH promoter. Additionally, the invention provides cell lines and transgenic animals expressing a transgene comprising the hTH promoter operably linked to a heterologous sequence, which cell lines and transgenic animals are useful for isolating TH+ cells for transplantation or for screening of therapeutic agents that affect TH+ function. Methods of producing cell lines and transgenic animals also provided.

6 Claims, 22 Drawing Sheets

OTHER PUBLICATIONS

Baffi, J. S., Palkovits, M., Castillo, S. O., Mezey, E. and Nikodem, V. M., Differential expression of tyrosine hydroxylase in catecholaminergic neurons of neonatal wild-type and Nurr1-deficient mice, Neuroscience, 93 (1999) 631-642.

Buervenich, S., Carmine, A., Arvidsson, M., Xiang, F., Zhang, Z., Sydow, O., Jonsson, E. G., Sedvall, G. C., Leonard, S., Ross, R. G., Freedman, R., Chowdari, K. V., Nimgaonkar, V. L., Perlmann, T., Anvert, M. and Olson, L., NURR1 mutations in cases of schizophrenia and manic-depressive disorder, American Journal of Medical Genetics, Dec. 4, 2000; 96 808-813.

Buscher, D., Bosse, B., Heymer, J. and Ruther, U., Evidence for genetic control of Sonic hedgehog by Gli3 in mouse limb development, Mechanisms.of.Development, 62 (1997) 175-182.

Chalfie, M., Green fluorescent protein. [Review] [42 refs], Photochemistry.& Photobiology., 62 (1995) 651-656.

Craig, S. P., Buckle, V. J., Lamouroux, A., Mallet, J. and Craig, I., Localization of the human tyrosine hydroxylase gene to 11p15: gene duplication and evolution of metabolic pathways, Cytogenetics.& Cell Genetics, 42 (1986) 29-32.

Daadi, M. M. and Weiss, S., Generation of tyrosine hydroxylase-producing neurons from precursors of the embryonic and adult forebrain f, Journal of Neuroscience, 19 (1999) 4484-4497.

Driever, W. and Nusslein-Volhard, C., The bicoid protein determines position in the Drosophila embryo in a concentration-dependent manner, Cell, 54 (1988) 95-104.

Drouin, J., Lamolet, B., Lamonerie, T., Lanctot, C. and Tremblay, J. J., The PTX family of homeodomain transcription factors during pituitary developments. [Review] [16 refs], Molecular & Cellular Endocrinology, 140 (1998) 31-36.

Du, X. and Iacovitti, L., Multiple signaling pathways direct the initiation of tyrosine hydroxylase gene expression in cultured brain neurons, Brain Research.Molecular.Brain Research, 50 (1997) 1-8.

German, M. S., Wang, J., Chadwick, R. B. and Rutter, W. J., Synergistic activation of the insulin gene by a LIM-homeo domain protein and a basic helix-loop-helix protein: building a functional insulin minienhancer complex, Genes & Development, 6 (1992) 2165-2176.

Ghosh, D., TFD: the transcription factors database, Nucleic.Acids. Research., 20 Suppl (1992) 2091-2093.

Giguere, V., Orphan nuclear receptors: from gene to function. [Review] [639 refs], Endocrine Reviews, 20 (1999) 689-725.

Hobert, O. and Westphal, H., Functions of LIM-homeobox genes. [Review] [78 refs], Trends in Genetics, Feb. 16, 2000; (2000) 75-83.

Horner, M. A., Quintin, S., Domeier, M. E., Kimble, J., Labouesse, M. and Mango, S. E., pha-4, an HNF-3 homolog, specifies pharyngeal organ identity in Caenorhabditis elegans, Genes & Development, 12 (1998) 1947-1952.

Hynes, M., Porter, J. A., Chiang, C., Chang, D., Tessier-Lavigne, M., Beachy, P. A. and Rosenthal, A., Induction of midbrain dopaminergic neurons by Sonic hedgehog, Neuron, 15 (1995) 35-44.

Hynes, M. and Rosenthal, A., Specification of dopaminergic and serotonergic neurons in the vertebrate CNS. [Review] [85 refs], Current Opinion in Neurobiology, 9 (1999) 26-36.

Iler, N., Rowitch, D. H., Echelard, Y., McMahon, A. P. and Abate-Shen, C., A single homeodomain binding site restricts spatial expression of Wnt-1 in the developing brain, Mechanisms of Development, 53 (1995) 87-96.

Kaneda, N., Kobayashi, K., Ichinose, H., Kishi, F., Nakazawa, A., Kurosawa, Y., Fujita, K. and Nagatsu, T., Isolation of a novel cDNA clone for human tyrosine hydroxylase: alternative RNA splicing produces four kinds of mRNA from a single gene, Biochemical & Biophysical Research Communications, 146 (1987) 971-975.

Karlsson, O., Thor, S., Norberg, T., Ohlsson, H. and Edlund, T., Insulin gene enhancer binding protein Isl-1 is a member of a novel class of proteins containing both a homeo- and a Cys-His domain, Nature, 344 (1990) 879-882.

Kawai, S. and Sugiura, T., Characterization of human bone morphogenetic protein (BMP)-4 and -7 gene promoters: activation of BMP promoters by Gli, a sonic hedgehog mediator, Bone Jul. 29, 2001; (1.):54.-61., 29 (2001) 54-61.

Kawasaki, H., Mizuseki, K., Nishikawa, S., Kaneko, S., Kuwana, Y., Nakanishi, S., Nishikawa, S. I. and Sasai, Y., Induction of midbrain dopaminergic neurons from ES cells by stromal cell-derived inducing activity, Neuron Oct. 28, 2000; (1.):31.-40., 28 31-40.

Kawasaki, H., Suemori, H., Mizuseki, K., Watanabe, K., Urano, F., Ichinose, N. and Sasai, Y., Generation of dopaminergic neurons and pigmented epithelia from primate ES cells by stromal cell-derived inducing activity, Proceedings of the National Academy of Sciences of the United States of America, 99 (2002) 1580-1585.

Kinzler, K. W., Bigner, S. H., Bigner, D. D., Trent, J. M., Law, M. L., O'Brien, S. J., Wong, A. J. and Vogelstein, B., Identification of an amplified, highly expressed gene in a human glioma, Science, 236 (1987) 70-73.

Kuziora, M. A. and McGinnis, W., Autoregulation of a Drosophila homeotic selector gene, Cell, 55 (1988) 477-485.

Lebel, M., Gauthier, Y., Moreau, A. and Drouin, J., Pitx3 activates mouse tyrosine hydroxylase promoter via a high-affinity binding site, Journal.of.Neurochemistry. 77. (2.):558.-567., Apr. 2001, 558-567, 2001.

Lee, J., Platt, K. A., Censullo, P. and Ruiz, Gli1 is a target of Sonic hedgehog that induces ventral neural tube development, Development, 124 (1997) 2537-2552.

Lee, S. H., Lumelsky, N., Studer, L., Auerbach, J. M. and McKay, R.D., Efficient generation of midbrain and hindbrain neurons from mouse embryonic stem cells, Nature Biotechnology Jun. 18, 2000; (6.):675.-9., 18 675-679.

LeMotte, P. K., Kuroiwa, A., Fessler, L. I. and Gehring, W.J., The homeotic gene Sex Combs Reduced of Drosophila: gene structure and embryonic expression, EMBO Journal, 8 (1989) 219-227.

Litingtung, Y. and Chiang, C., Specification of ventral neuron types is mediated by an antagonistic interaction between Shh and Gli3, Nature Neuroscience, Oct. 3, 2000; 979-985.

Liu, J., Merlie, J. P., Todd, R. D. and O'Malley, K. L., Identification of cell type-specific promoter elements associated with the rat tyrosine hydroxylase gene using transgenic founder analysis, Brain Research.Molecular.Brain Research., 50 (1997) 33-42.

Lonnerberg, P., Schoenherr, C. J., Anderson, D. J. and Ibanez, C. F., Cell type-specific regulation of choline acetyltransferase gene expression. Role of the neuron-restrictive silencer element and cholinergic-specific enhancer sequences, Journal of Biological Chemistry, 271 (1996) 33358-33365.

Lubon, H. and Hennighausen, L., Nuclear proteins from lactating mammary glands bind to the promoter of a milk protein gene, Nucleic Acids Research, 15 (1987) 2103-2121.

Mahaffey, J. W. and Kaufman, T. C., Distribution of the Sex combs reduced gene products in Drosophila melanogaster, Genetics, 117 (1987) 51-60.

McGinnis, W., Jack, T., Chadwick, R., Regulski, M., Bergson, C., McGinnis, N. and Kuziora, M. A., Establishment and maintenance of position-specific expression of the Drosophila homeotic selector gene Deformed. [Review] [71 refs], Advances in Genetics, 27 (1990) 363-402.

Meloni, R., Albanese, V., Ravasard, P., Treilhou, F. and Mallet, J., A tetranucleotide polymorphic microsatellite, located in the first intron of the tyrosine hydroxylase gene, acts as a transcription regulatory element in vitro, Human.Molecular.Genetics, 7 (1998) 423-428.

Milbrandt, J., Nerve growth factor induces a gene homologous to the glucocorticoid receptor gene, Neuron, 1 (1988) 183-188.

Min, N., Joh, T. H., Kim, K. S., Peng, C. and Son, J. H., 5' upstream DNA sequence of the rat tyrosine hydroxylase gene directs high-level and tissue-specific expression to catecholaminergic neurons in the central nervous system of transgenic mice, Brain Research. Molecular.Brain Research., 27 (1994) 281-289.

Miwa, K. and Strominger, J. L., The HLA-DQ beta gene upstream region contains an immunoglobulin-like octamer motif that binds cell-type specific nuclear factors, Nucleic Acids Research, 15 (1902) 8057-8067.

Morello, R., Zhou, G., Dreyer, S. D., Harvey, S. J., Ninomiya, Y., Thorner, P. S., Miner, J. H., Cole, W., Winterpacht, A., Zabel, B., Oberg, K. C. and Lee, B., Regulation of glomerular basement membrane collagen expression by LMX1B contributes to renal disease in nail patella syndrome, Nature Genetics, Feb. 27, 2001; 205-208.

Murphy, E. P. and Conneely, O. M., Neuroendocrine regulation of the hypothalamic pituitary adrenal axis by the nurr1/nur77 subfamily of nuclear receptors, Molecular.Endocrinology, 11 (1997) 39-47.

Nagatsu, I., Karasawa, N., Yamada, K., Sakai, M., Fujii, T., Takeuchi, T., Arai, R., Kobayashi, K. and Nagatsu, T., Expression of human tyrosine hydroxylase-chloramphenicol acetyltransferase (CAT) fusion gene in the brains of transgenic mice as examined by CAT immunocytochemistry, Journal.of.Neural Transmission.—General.Section., 96 (1994) 85-104.

Nagatsu, T., Levitt, M. and Udenfriend, S., Tyrosine Hydroxylase, The Initial Step in Norepinephrine Biosynthesis, Journal of Biological Chemistry, 239 (1964) 2910-2917.

O'Malley, K. L., Anhalt, M. J., Martin, B. M., Kelsoe, J. R., Winfield, S. L. and Ginns, E. I., Isolation and characterization of the human tyrosine hydroxylase gene: identification of 5' alternative splice sites responsible for multiple mRNAs, Biochemistry, 26 (1987) 2910-2914.

Packer, A. I., Crotty, D. A., Elwell, V. A. and Wolgemuth, D. J., Expression of the murine Hoxa4 gene requires both autoregulation and a conserved retinoic acid response element, Development, 125 (1998) 1991-1998.

Perlmann, T. and Jansson, L., A novel pathway for vitamin A signaling mediated by RXR heterodimerization with NGFI-B and NURR1, Genes & Development, 9 (1995) 769-782.

Peverali, F. A., D'Esposito, M., Acampora, D., Bunone, G., Negri, M., Faiella, A., Stomaiuolo, A., Pannese, M., Migliaccio, E. and Simeone, A., Expression of HOX homeogenes in human neuroblastoma cell culture lines, Differentiation, 45 (1990) 61-69.

Philips, A., Lesage, S., Gingras, R., Maira, M. H., Gauthier, Y., Hugo, P. and Drouin, J., Novel dimeric Nur77 signaling mechanism in endocrine and lymphoid cells, Molecular & Cellular Biology, 17 (1997) 5946-5951.

[0229] Powell, J. F., Boni, C., Lamouroux, A., Craig, I. W. and Mallet, J., Assignment of the human tyrosine hydroxylase gene to chromosome 11, FEBS Letters., 175 (1984) 37-40.

[0230] Prestridge, D. S., Signal Scan: a computer program that scans DNA sequences for eukaryotic transcriptional elements, Computer.Applications.in the.Biosciences., 7 (1991) 203-206.

Riddle, R. D., Johnson, R. L., Laufer, E. and Tubin, C., Sonic hedgehog mediates the polarizing activity of the ZPA, Cell, 75 (1993) 1401-1416.

Roelink, H., Porter, J. A., Chiang, C., Tanabe, Y., Chang, D. T., Beachy, P. A. and Jessell, T. M., Floor plate and motor neuron induction by different concentrations of the amino-terminal cleavage product of sonic hedgehog autoproteolysis, Cell, 81 (1995) 445-455.

Ruppert, J. M., Vogelstein, B. and Kinzler, K. W., The zinc finger protein GLI transforms primary cells in cooperation with adenovirus EIA, Molecular & Cellular Biology, 11 (1991) 1724-1728.

Sacchetti, P., Mitchell, T. R., Granneman, J. G. and Bannon, M. J., Nurr1 enhances transcription of the human dopamine transporter gene through a novel mechanism, Journal.of.Neurochemistry. 76.(5.):1565.-1572., Mar. 2001.

Sanchez-Pernaute, R., Studer, L., Bankiewicz, K. S., Major, E. O. and McKay, R. D., In vitro generation and transplantation of precursor-derived human dopmaine neurons, Journal.of.Neuroscience Research. Aug. 15, 2001;65.(4.):284.-8., 65 284-288.

Saucedo-Cardenas, O., Quintana-Hau, J. D., Le, W. D., Smidt, M. P., Cox, J. J., De Mayo, F., Burbach, J. P. and Conneely, O. M., Nurr1 is essential for the induction of the dopaminergic phenotype and the survival of ventral mesencephalic late dopaminergic precursor neurons, Proceedings.of.the.National.Academy.of.Sciences.of.the.United.States.of.A- merica., 95 (1998) 4013-4018.

Sawamoto, K., Nakao, N., Kobayashi, K., Matsushita, N., Takahashi, H., Kakishita, K., Yamamoto, A., Yoshizaki, T., Terashima, T., Murakami, F., Itakura, T. and Okano, H., Visualization, direct isolation, and transplantation of midbrain dopaminergic neurons, Proceedings.of.the.National.Academy.of.Sciences.of.the.United.States.of.A- merica. 98. (11.):64 23.-6428., May 22, 2001 (1 A.D.) 6423-6428, 2001.

Schimmel, J. J., Crews, L., Roffler-Tarlov, S. and Chikaraishi, D. M., 4.5kb of the rat tyrosine hydroxylase 5' flanking sequence directs tissue specific expression during development and contains consensus sites for multiple transcription factors, Molecular.Brain Research. 74.(1.-2.): 1.-14., (1999).

Schoenherr, C. J., Paquette, A. J. and Anderson, D. J., Identification of potential target genes for the neuron-restrictive silencer factor, Proceedings of the National Academy of Sciences of the United States of America, 93 (1996) 9881-9886.

Scott, M. P., Vertebrate homeobox gene nomenclature, Cell, 71 (1992) 551-553.

Simeone, A., Acampora, D., Gulisano, M., Stornaiuolo, A. and Boncinelli, E., Nested expression domains of four homeobox genes in developing rostral brain. [see comments.], Nature, 358 (1992) 687 -690.

Simeone, A., Acampora, D., Nigro, V., Faiella, A., D'Esposito, M., Stomaiuolo, A., Mavilio, F. and Boncinelli, E., Differential regulation by retinoic acid of the homeobox genes of the four HOX loci in human embryonal carcinoma cells, Mechanisms of Development, 33 (1991) 215-227.

Smidt, M. P., Asbreuk, C. H., Cox, J. J., Chen, H., Johnson, R. L. and Burbach, J. P., A second independent pathway for development of mesencephalic dopaminergic neurons requires Lmx1b, Nature Neuroscience, Apr. 3, 2000; 337-341.

Smidt, M. P., van Schaick, H. S., Lanctot, C., Tremblay, J. J., Cox, J. J., van der Kleij, A. A., Wolterink, G., Drouin, J. and Burbach, J. P., A homeodomain gene Ptx3 has highly restricted brain expression in mesencephalic dopaminergic neurons, Proceedings.of.the.National.Academy.o-f.Sciences.of.the.United.States.of.America., 94 (1997) 13305-13310.

Stull, N. D., Jung, J. W. and Iacovitti, L., Induction of a dopaminergic phenotype in cultured striatal neurons by bone morphogenetic proteins, Brain Research.Developmental Brain Research, Sep. 23, 2001;130 91-98.

Tornqvist, N., Hermanson, E., Perlmann, T. and Stromberg, I., Generation of tyrosine hydroxylase-immunoreactive neurons in ventral mesencephalic tissue of Nurr1 deficient mice, Dev.Brain Research, 133 (2002) 37-47.68. Stull, N. D., Jung, J. W. and Iacovitti, L., Induction of a dopaminergic phenotype in cultured striatal neurons by bone morphogenetic proteins, Brain Research. Developmental Brain Research, Sep. 23, 2001;130 91-98.

Trocme, C., Sarkis, C., Hermel, J. M., Duchateau, R., Harrison, S., Simonneau, M., Al-Shawi, R. and Mallet, J., CRE and TRE sequences of the rat tyrosine hydroxylase promoter are required for TH basal expression in adult mice but not in the embryo, European.Journal.of.Neuro- science, 10 (1998) 508-521.

Wakayama, T., Tabar, V., Rodriguez, I., Perry, A. C., Studer, L. and Mombaerts, P., Differentiation of embryonic stem cell lines generated from adult somatic cells by nuclear transfer. [see comments], Science Apr. 27, 2001;292.(5517.):740.-3., 292 (1 A.D.) 740-743.

Wilson, T. E., Fahrner, T. J., Johnston, M. and Milbrandt, J., Identification of the DNA binding site for NGFI-B by genetic selection in yeast, Science, 252 (1991) 1296-1300.

Wingender, E., Chen, X., Fricke, E., Geffers, R., Hehl, R., Liebich, I., Krull, M., Matys, V., Michael, H., Ohnhauser, R., Pruss, M., Schacherer, F., Thiele, S. and Urbach, S., The TRANSFAC system on gene expression regulation, Nucleic Acids Research, Jan. 1. 2001;29 281-283.

Zhang, S. C., Wernig, M., Duncan, I. D., Brustle, O. and Thomson, J. A., In vitro differentiation of transplantable neural precursors from human embryonic stem cells. [see comments.], Nature Biotechnology, Dec. 19, 2001; 1129-1133.

Albanese, V., Biguet,N. F., Kiefer,H., Bayard,E., Mallet,J., and Meloni,R. (2001). Quantitative effects on gene silencing by allelic variation at a tetranucleotide microsatellite. Human Molecular Genetics 10, 1785-1792.

* cited by examiner

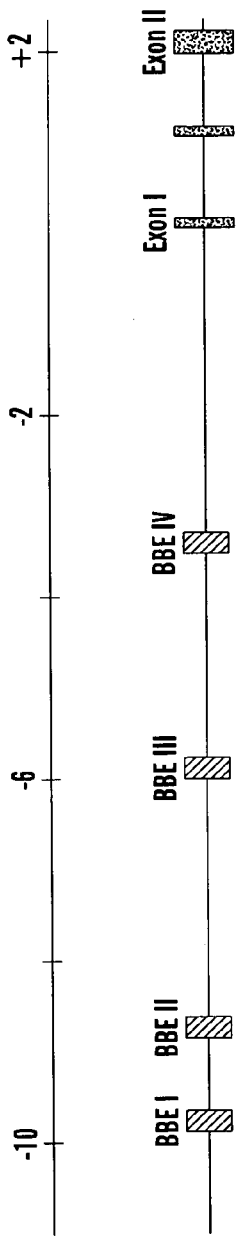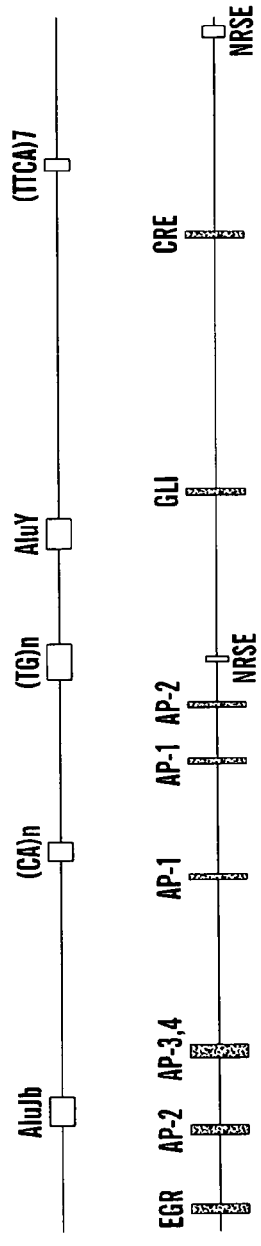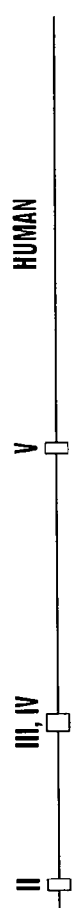
FIG. 3A
FIG. 3B
FIG. 3C
FIG. 3D
FIG. 3E
FIG. 3F
FIG. 3G

```
hTH bicoid binding elements I-IV BBTAATCYV
I   (+)   tgTAATCcc  1142-1150  (-9826,-9818)
II  (-)   gcTAATCcc  2169-2161  (-8799,-8807)
III (+)   gcTAATCcc  5042-5050  (-5926,-5918)
IV  (+)   tgTAATCcc  7513-7521  (-3455,-3447)
```
*FIG. 9A*
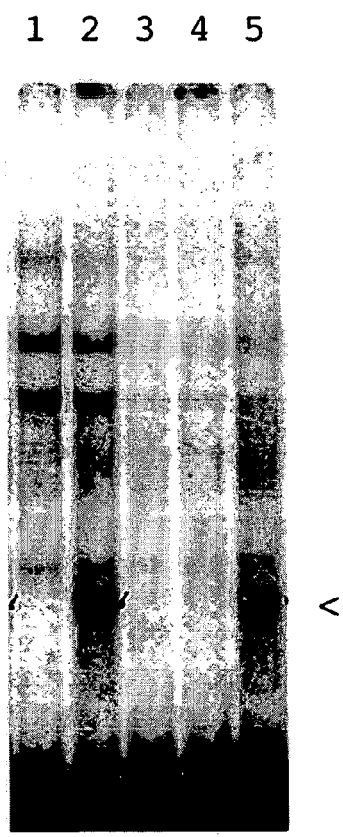
*FIG. 9B*
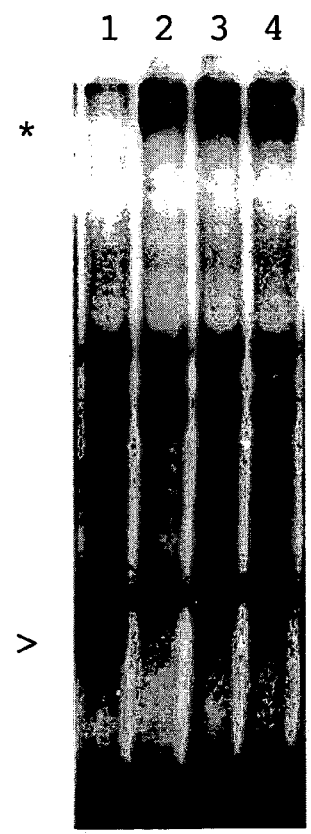
*FIG. 9C*

SEQ ID NO: 1
```
tcgacgtgaa cgaatcggtc acacacacgc agaaaggtgc cgctgctggg
gacctgtggg gcggggcgg ggcagaagga aggtccctg tttgggggac
cctttattaa aaacaggcgg caagctgagg cgtccagctg agttcatccc
aggccccaaa gtaatcgcac ggccaataag ccctgcctaa gatgaggacg
ggtgggtctg gaccgaggcc ctggcgggag ggagggtcct gggcgtgcca
ccagctctcc ggtcggaagc ttctgcatgg gccgtgccct gcgctgggag
actcctgccc gggcagcctt gctccaaggt cggctccaca gagggtgccc
gccctctcag ccctggcctg tggcacctgc ccacagccct ttcttccctg
gatgcagttt ttgcccctc tgtgtcctcg gctgcacgag tagggctttt
cttgggttgg ctcccgcct ggcccggact gacccggact ggctgaggct
gaggctgaca gtgcaggaa ggagccagaa gccactatgg ctgctgtgca
gagaccaagg tgtctcccta cacctgtggc ccccagggcc ccagggacac
agggtccaca ccctgcccca cctgctccat ctccgggacg ccctcgctcc
ccaatctgat tgcacagggt gggggccca gcagccttgg tgacagttct
tcatcccaag ggcccgccca gtttctcctg gctcctgggg atgggagtgg
cctgggttgt ggccccacca gctctgtgac agggctcttg atgcttctca
ggccctagtt tccctgagac ctgctggcca ggagctcagg cctcctggtt
tctggttact ttcctcccc tagaaagcag ccttggcaga cagaacagag
gcccagaaga tcccgggagg ctccccaggc ccagaatctg gggaacttgc
aaggatttgg aatcctggcc gggtgtggta gcgagcctg taatcccaga
atttggggag gctaaggtgg gaggattact tgaggccagg agattgagac
cagcctgggc aacacagtga gacccctct ctacaaaaaa attttaaaa
atagccaggc gtgctggtgt gcccctgcag ctccagctac ttgggaggct
gaaatgggag gatggcttga gcccgggagg tcaaggctgc agtgagccat
gatcaagcca ctgcacttca gcctgggtga caaagaccct gtctctcaaa
ataaacattt aaaaaataga agttaaatcc tcttttggag actgtggggt
gaggggagtg tggccacacc acagcccttc cacctcccca ttgtgtgccc
cgaactgtgc tgtgctggcc actggcctca ccctccctga agcatggcag
gtcccccacc cccaaggcca tgctggggtg gggacagggg ccatgtgctt
cccacttgga gggggctgtt ccagacacct ccctggccgc ccctggcagg
gtctcggctg tactggatgt gaggaccgtg ggcctccctt ccccagact
atgagagcct ccaaaattgg gaccgtgctg tttcccttc cgtgctgttt
cccaagggc acccaggaaa tgcttgctgc gtgaatcagt gaatgagtga
gttcattcac ctggggctg ggtggggacg atggagcctt ccagcctcct
gggacctgcc ctcagtgtgg aaagtgagga ggcatctgtc ttcctgagga
aaacctgggc ttagtcctcc ctctggccca ggaggggacc ggaccccaca
gctggaggga gccggcttag ctgacagcga gtgtattaaa aacaagcttt
ggagcaaagc ggacaagctc aggtgttggt agagttcatc ccaggcccca
aagtaatcac atggcaaaca agccctgtct aaatatcacg gcggctgggg
cagcggcacg cagcggcctg gaaatgtcag ccggggggtgg gggctcctcc
gagccccggg attagcagag gtacctgaag tgaatgcgcc cacctcctcc
ttcctgctcc tgctcaggac ctgggctggg ccagcccggg gcacctgggg
```

*FIG. 11A*

```
aggggctcag agggtctcac tggggccagg ggctcttctt tcagccccag
cccgggctgg ttcccatggg gtagcaggct gaggagagtg gggagactga
gcttggccgg agtggggcgg acgcacttcc agcccaaac cagcagccca
cgggtggggg cagagaaagc tgcccccctg caggcccagt gagtcctcga
gagagggggc cacccggcca tggggggggtg gtgatgttgg ttcggggaac
ctagggcatc tggaccagcc cctggacaag gcggtcacag cagccactgc
ctgagcaggc cacctgcggg cttccctcca ggtctgccca tcggctcagg
gcttccagag cccaagggag caacacgttt ctcctgagca cgggtggagg
gaaaataagg atgtttacga tcgagttgcc catggaagcg ttaccaagcc
ccctggagac tcatctcacc gcagtgggac ctttgcattc tctcaggcgg
tgggggtctc tgccgtgttg tccgtaaagt gtcagcgtgg ggccaactgg
ggacctcagc agccacgtcc aaccctcatc tgaaacaaga actggaggcc
tggctgctc ctcccttccc gccctcagga gcacagggtg gcaggaggtg
aactccatgg gcgaggggct cttgctcttg caggccccca aagtcagtca
ggtgcagaag ggaaggacag gattcaggga caggagacac acaggggggtc
ccctctgttc caggatgctc ccaaatctga gcccagctgc ccccagggtg
gagggtgcgt ggacagccgg ccaagagggg cggggccaca gaaggccctg
gcgaggccgt ggggccaagc agaggagcct acagtggctg gccagacggg
tcctaggtga tgcaaggggt cctccgcacc cctgttctgt ttccccggct
ctgacccagt gtgcggcctc tcctccatgt ctgtatgtgg ctgcctccaa
ggcccctctc ctcaggccct gtatgtccaa gctgggcctc cttcctctga
tcgcccttgg gagaggtggc attgaggtca cctcctcccc tcccagagtc
tgcatcttgt gggcaaatgc cccagtgcct cccaccatcc tccatgcatg
cagctgcctg cccaggtccc ctgtgaacgc agcccagggc cgtgcaggcc
acaggcgggg ctcatctccc caggtggggc ctccaagtct acacctgtgg
ctgggaaggg gagtcacagc acagatggaa tgaagcacat gagccctggg
tgtggacctg cctcagctca gagcagcggt gggaccacat cttctccctg
ccacaggcca ggtgactagc acccaagccc gtggcactgg cactgctggg
gggccagggc gggctgtggc cttgcaagga gatgtgattt gctgtcaaag
cacagctgcc gcctcggtga gtgactaatg agaactgaat gccgctctta
ttgcttttca ctcgactaat ttgtcagagg ctgtcaagag ccaggggggag
ggggcagagg gtggggaccg gaggtctgat tgagtcaccg gcatggggggc
gaggctgggt gcccggaggg gtctgcaaga aaccaggagc acctggcagg
aactcaggggc cggtggggac cttggccatg atgtcgtgtg agagtccgga
gggacacagg agctgggtc accctgttttg ttccatatca atggctggtc
agctcttcta agccctact gtacacacac atgcacatgc atacatagga
cacacacaca cacttacaca aacacgca tgcatgcatg tggacataaa
atcatacact cacatgaata attttagaag catgtacaac acatgtacac
gcagagaagc actcccacac atgcttcctg gcacacacac acacgcgc
acacacacac acccttgaat gcacactctg tctcccacac agacacagac
cagcgaaaac tccaggccaa gctctggtgc gtgggttccc aagcctggct
gcacacacaa ccagggtgct ctcggcaatt ccagcatctc catacccctg
gagcctcttg tcctggtgtg ggcttcctgg tgatgtgggc cagccaggta
tgggtggaac cgtcctactc cccctccagc ccaagcctg agccagcctg
agtctggcat ggagctcctg gagccaggtg agcagtgagg ggcgctggga
gctggggaga tgccctgtgg gtaggagatg cgcacccgc ccacccggat
```

*FIG. 11B*

```
acccttcctc ccagctgaat gcctggctgc cagggaccac ggtgacttct
cttgcttggc tctgtaacct gcccccttcg tacccttttcc ctccctctgc
ctccacctct gcccgactcg gtcccacagg accctctggc cactggatcc
ccttccctgg aagcacccct cactgctcac ctggctccag gagctccatg
ccagactcag gctggctcag gcttagggct ggaggggag taggacggtt
ccacccatac ctggctggcc cacatcacca ggaagcccac accaggacaa
gaggctccag gggtatggag atgctggaat tgccgagagc accctggttg
tgtgtgcagc caggcttggg aacccacgca ccagagcttg gcctggagtt
ttcgctggtc tgtgtctgtg ggcctttggg ggtcccacac acacaagggg
ctcaaggctg acccctcctc ccacaagggc ctgcaactgc taatccctga
tgccccccac tgtgtggatg gcaaaactga gtccagggcc caagggctg
agtcaggacc ctcttttcgg cccctacat ggtgggtctc aacactgagg
cagtccctac aggcaacaag gatggaagga cagcactggc tgtccaggct
ggagggactc agagaggagg ccactggggg actgcctga ggaggagggc
agcccgggcc tgagggcctg gcaggatttg gtggggaagg gaaagtggag
ccccaggtgg gcagcagcag tagcagaagg ggggcaggga gccgtctgtg
gggacaggg agggtccggc tgcctgtcca gggtgtggag gaggagaggc
agcccacagg ctcagagccc gaaggaggcg tggtgcctgc tctgccggcc
tcgctctggg cctgacttcc aaacacccaa ttatccctaa gtgcatccga
tcgactggca gggcggctgt tccggggccc acctcgtcca tgcgctccgc
ccgccctgct gtggggctcc atctgatggc ctcattaggg ataattgctc
tggcatttgg gtctgacagg gacggcggat tctgtcctgt gttgggggcgt
cttggttctt ccagcttggg ggatggaggg gagctgcttc cttacacggc
agagaaaggc cctgcacccc aggcggggca agatggcgtg aggggaggat
gcaggactca ctgtcccctg ccttcttggg acaatgggaa ctgagggaca
gcccagggtg gcatgacacc ccaaatcctc aggaggtccc ccactgtctc
ccaaatgtga gtgggggtct gggaggctgc aggccggtgt ccctgggagc
caggctctag aggggcatc tctggggacc ctggggaccc cgggctataa
agagaactgc ggagtagaca tgggcggggg ggcagtgtgt gctccagcat
gtgtgtgtgt gtgtgcatgt acacgtgtgc acctgtatcg cctgtgtgtg
tgcatgtgat gtgtacacgt gtcatgcatg cacgcacatg tgtagtgtgt
gctcgtgtgt ggtgtgtgcc tgtgtcatgt atgagcacac ttgtatatgt
tgtgtgtact gtgtcatata tgagtgtgtt tgcctgtgta gtgcatgcac
atccgtgtgt gcatctggtg tgtccgtggg tcattacgag tgcatcgtat
gtgtatcgtg tacatgagta cacttgtatg tgtggtgtgt acaggtgcca
tgtaagtgtg cttgtacata tatgcatgca tgtgtcatat gcatctgtgt
gtgcatgtgt gtggtgcaca catgtgttat gtctgagtgt gcctgtatgt
gtgctatgta cacgtcatgt gtgagtgtgc ttgcatgtgc agtgtgtgga
tgctgcttgt acctgtggtg tgtacctgtg tcatgggtgc tcacacgtgc
atggagtgtt gtgtgtgtgc ttgtgtgccc catgtgtgca tgtgtgtgtg
cctcacacag atgcctgcat ttgcctaggc acttgcaaga ggacaccatg
ctggctctca aagatcacag ggccacctga gcctgtgca caccacagcc
aggccatggc tagaccctgc agagccacag ggcgatgcct gtcagccagg
ggacccagaa cacctcctgg gcccctcccc agcacatggc tgggctcctc
cagcaggcct ggatttggga agggcccgtg gtgggcaagg ctggtgctgg
ggagcaggcc tggtggcctc agagactcgc cctgtgggcg gagcagcctc
acagccaggt tgaagtcagc 6720
```

FIG. 11C

```
actctgcccc tgccccacgc ggggagcggg caccagtccc agggcacaga
cgtgctgggt gattaatctg ggtgattaag cctcgggctg agaggctgtt
gagagagaac acgctccatt gtggagctgg ctcagcattc cttacggcca
tggtggcagg ggctgtaacc acagggacgg cggaagtggt ggagggtggt
ggggtatgga gggaagccca gagggctctg tgcaggaagg tggagcctgg
tgcaatggag gggacagcaa gggctcctca gacctctgcg ggcccccac
tcccctggtc acctgttttg tctctgatct ggcctgggtc ggccctcact
cctggcccca cctcatagcc cccctggtg gggctccgct ccagcccttc
tccttcccag gggccagtat gctggcccca ggggtctctt ggggcgtgac
ctcggcctcc agagaaccct gtcccagctc tgcccttccc tctgggtct
ctgtagatgg gacgctggtc acagcagcct gtctgatttg ttccctgtgg
cctaggttcc tgagcccac agtgccaggg gatggatgcc accggatctt
tgaaagacca gtgtcaggcc gggcgcagtg gctcacgcct gtaatcccag
cactttggga ggccgaggtg ggcggatcac gaagtcagga gatcgagacc
atcctggcta acacggtgaa accccgtctc cactaaaaat acaaaaagtt
agctgggcgt ggtggtgggc gcctgtagtc ccagctactc gggaggctga
ggcaggagaa tggcgtgaac cggggaggcg gagcttgcag tgagccgaga
tcgcgccatt gcactccagc ctgggtgaca gagcgagact cggtctcaaa
aaaaaaagaa aaaaggaaa gaccagtgtc ttgggagttg ggaaacctgg
gctggagact cactgcatga cccctgagaa gttgcacctc agaacctcag
tcctcgcatc tgcagaatgg gtctgtgaac acctcagctg cccgaacgtg
gatgccgcag gctgacccag cactgagctc taccaagacc agggggccagc
cgtgtgctcc ctccaggcct gtgcccagcg tggagaggcc tcgtcccgtg
ggcgctgggg tggagccttc ctggtgtttg tggacatctc tggagagggc
cagaggcagg tgggtgacac ggggcatggc tcaatcatgg gtggtccaga
ctggagaggt accctcgggc tgggagcggg gaggctggcc agggtggact
ttcggggcct ccatggatac cctcaccatc tggaatcgga gaggggcacg
gcacaaagga gggcggggcc agggccagga ctggagtcgg gggcacctct
gtgccaacag gggccttgga tctggggtac agcatggttc cccggccctg
aaggggctgg cgtgtgggac aggcttccca ggaatggata ggcagggatg
gatgctgcct gattggggcg ggaggctgga ggcagggcag gtgcaggcac
ctgagggcag cactcacctc cacagggtc caggggcctc cccagcctca
gtacctggcc tgggctcctg cctccagaga gcctggcccc aaggaagagt
ctagtaagct tagttcccat cgggcttcca tgaaagcaca actggcccgg
caggaaaccg aattaaaaag caatatttgt atcagtggaa gacatttgct
gaaaggttaa atccacatcc ggcagtgtgg gccatgagcc tccggcgtgg
tgttcatcag gcatgtctct cctcctggcc tgggcacctg agcactgggg
ctgccctggg cagagctggg gcaggtgct ggggggcctg gagctgcctc
accgagggat cctcagcagc cgaccctggg ggaggcaaat gagactcttt
ctggggacct tgaggggagc tcggggagc catgcagagc ttcaccaggc
ctggacactg ggcatggagg ctgggccacc caagggccat caccagggac
tcaggtgggt gggcctcagc cctgggtgac agaagctcac gggctgcagg
gcgaggccag aggctgagcc ttcaggctga ggtcttggag gcaaatccct
ccaacgccct tctgagcagg cacccagacc tactgtgggc aggacccaca
ggaggtggag gcctttgggg aacaccgtgg aggggcatag catctccgag
agaggacagg gtctgcactg ggtgctgaga gacagcaggg gccgagcggt
```

*FIG. 11D*

```
aggcttccct gccccaggg atgttccagg ggagcgcaag ggaggggcat
taatatcgtg gcaagaaagg gcaggcattg cagagtgagc agcgacggaa
ctgggttttg tgggatgcat aggagttcac ccggataaga ggtgggtgag
gaatgacact gcaaaccggg gatcacggag ccccaaatcc ttctgggcca
ggaagtggga agggttgggg ggtcttccct ttgctttgac tgagcactca
gcctgcctgc agaggcagc gaggagccac ggagggtgt gggacaggga
tgccatggct gaagcagttt taggaaaggt cccaggggct attgttgaag
agagaacggg gagcggggag tcccacagct gacaggagca gagtgggccc
tgagagatgc cagctctggg tgccacagtg accagccggg gtaggccttc
gagaagtcag ggagcgtcta gggcttctgg ctcctgctgg gcccagggtg
tcatcttggg ctgccaacac cagaaagccc agcagataca ggaagcccca
agccctgtcg gaaacggttc ttctccagga gggacagcgg tggcagcgtt
cagccgcagg ccatgcactc tggggccacg tccttccctc tgtacagtcc
agcattgtca aggcgggctc tggccatctc tgctgacccc agagggatgg
ggaggcctcc ccttccacca gaagggccag aagccaccct gggcagggc
atcactctcc ctgggtgggg cagcggcggg gagcaggagg tgccagtggg
cgtgggctgg atgcgggtgc ctgcggggcg gacatggaac ttggggggagg
ctctaggctg gggttgtcct caagggagtt ctcaggtcac cccagggtca
ccctcaaccc ggggcctggt ggggtagagg agaaactgca aaggtctctc
caaggggaag gcatcagggc cctcagcact gagggacgtg cgtgctcttc
aaagaagggg ccacaggacc ccgagggaag ccaggagcta gcagtgggcc
atagaggggc tgagtggggt gggtggaagc cgtccctggc cctggtcgcc
ctggcaaccc tggtggggac tgtgatgcag gaggtggcag ccatttggaa
acgcgtggcg tctccttaga gatgtcttct tcagcctccc agggtcctcc
acactggaca ggtgggccct cctgggacat tctggacccc acagggcgag
cttgggaagc cgctgcaagg gccacacctg cagggcccgg gggctgtggg
cagatggcac tcctaggaac cacgtctaca agacacacgg cctggaatct
tctggagaag caaacaaatt gcctcctgac atctgaggct ggaggctgga
ttccccgtct tgggctttc tgggtcggtc tgccacgagg ttctggtgtt
cattaaaagt gtgccctgg gctgccagaa agcccctccc tgtgtgctct
cttgagggct gtggggccaa ggggaccctg gctgtctcag cccccgcag
agcacgagcc cctggtcccc gcaagcccgc gggctgagga tgattcagac
agggctgggg agtgaaggca attagattcc acggacgagc cctttctcct
gcgcctccct ccttcctcac ccaccccgc ctccatcagg cacagcaggc
aggggtgggg gatgtaagga ggggaaggtg ggggacccag aggggctttt
gacgtcagct cagcttataa gaggctgctg ggccagggct gtggagacgg
agcccgga                                            10828

SEQ ID NO: 38
ggccgcataa cttcgtatag catacattat acgaagttat ggatccaccc
tctcttctca tctctgagcc gggtgttccc aaacttccct cctggtctgt
tcatccacca ggctctgagg gccagccctg cctggcaagg ggggaaccaa
ggggccaact ttagttttcc agaagcctct gtccagggga ggagtcgacg
tgaacgaatc ggtcacacac acgcagaaag gtgccgctgc tggggacctg
tggggcgggg gcggggcaga aggaaggtcc cctgtttggg ggaccctttta
```

*FIG. 11E*

```
ttaaaaacag gcggcaagct gaggcgtcca gctgagttca tcccaggccc
caaagtaatc gcacggccaa taagccctgc ctaagatgag gacgggtggg
tctggaccga ggccctggcg ggagggaggg tcctgggcgt gccaccagct
ctccggtcgg aagcttctgc atgggccgtg ccctgcgctg ggagactcct
gcccgggcag ccttgctcca aggtcggctc cacagagggt gcccgccctc
tcagccctgg cctgtggcac ctgcccacag ccctttcttc cctggatgca
gttttgccc cctctgtgtc ctcggctgca cgagtagggg ctttcttggg
ttggctgccc gcctggcccg gactgacccg gactggctga ggctgaggct
gacagtgcag ggaaggagcc agaagccact atggctgctg tgcagagacc
aaggtgtctc cctacacctg tggccccag ggcccaggg acacagggtc
cacaccctgc cccacctgct ccatctccgg gacgccctcg ctccccaatc
tgattgcaca gggtggggg cccagcagcc ttggtgacag ttcttcatcc
caagggcccg cccagtttct cctggctcct ggggatggga gtggcctggg
ttgtggcccc accagctctg tgacagggct cttgatgctt ctcaggccct
agtttccctg agacctgctg gccaggagct caggcctcct ggtttctggt
tactttcct cccctagaaa gcagccttgg cagacagaac agaggcccag
aagatcccgg gaggctcccc agcccagaa tctggggaac ttgcaaggat
ttggaatcct ggccgggtgt ggtagccgag cctgtaatcc cagaatttgg
ggaggctaag gtgggaggat tacttgaggc caggagattg agaccagcct
gggcaacaca gtgagacccc ctctctacaa aaaatttt aaaaatagcc
aggcgtgctg gtgtgcccct gcagctccag ctacttggga ggctgaaatg
ggaggatggc ttgagcccgg gaggtcaagg ctgcagtgag ccatgatcaa
gccactgcac ttcagcctgg gtgacaaaga ccctgtctct caaaataaac
atttaaaaaa tagaagttaa atcctctttt ggagactgtg gggtgagggg
agtgtggcca caccacagcc cttccacctc cccattgtgt gccccgaact
gtgctgtgct ggccactggc ctcaccctcc ctgaagcatg gcaggtcccc
caccccaag gccatgctgg ggtggggaca ggggccatgt gcttcccact
tggagggggc tgttccagac acctccctgg ccgcccctgg cagggtctcg
gctgtactgg atgtgaggac cgtgggcctc ccttcccca gactatgaga
gcctccaaaa ttgggaccgt gctgtttccc tttccgtgct gtttcccaaa
gggcacccag gaaatgcttg ctgcgtgaat cagtgaatga gtgagttcat
tcacctgggg gctggtggg gacgatggag ccttccagcc tcctgggacc
tgccctcagt gtggaaagtg aggaggcatc tgtcttcctg aggaaaacct
gggcttagtc ctccctctgg cccaggaggg gaccggaccc cacagctgga
gggagccggc ttagctgaca gcgagtgtat taaaaacaag ctttggagca
aagcggacaa gctcaggtgt tggtagagtt catcccaggc cccaaagtaa
tcacatggca aacaagccct gtctaaatat cacggcggct ggggcagcgg
cacgcagcgg cctggaaatg tcagccgggg gtgggggctc ctccgagccc
cgggattagc agaggtacct gaagtgaatg cgcccacctc ctccttcctg
ctcctgctca ggacctgggc tgggccagcc cggggcacct ggggagggc
tcagagggtc tcactgggc cagggctct tctttcagcc ccagcccggg
ctggttccca tggggtagca ggctgaggag agtggggaga ctgagcttgg
ccggagtggg gcggacgcac ttccaggccc aaaccagcag cccacgggtg
gggcagaga aagctgcccc cctgcaggcc cagtgagtcc tcgagagagg
gggccacccg gccatggggg ggtggtgatg ttggttcggg gaacctaggg
catctggacc agcccctgga caaggcggtc acagcagcca ctgcctgagc
```

```
aggccacctg cgggcttccc tccaggtctg cccatcggct cagggcttcc
agagcccaag ggagcaacac gtttctcctg agcacgggtg gagggaaaat
aaggatgttt acgatcgagt tgcccatgga agcgttacca agcccctgg
agactcatct caccgcagtg ggacctttgc attctctcag gcggtggggg
tctctgccgt gttgtccgta aagtgtcagc gtggggccaa ctggggacct
cagcagccac gtccaaccct catctgaaac aagaactgga ggcctgggct
gctcctccct tcccgccctc aggagcacag ggtggcagga ggtgaactcc
atgggcgagg ggctcttgct cttgcaggcc cccaaagtca gtcaggtgca
gaagggaagg acaggattca gggacaggag acacacaggg ggtcccctct
gttccaggat gctcccaaat ctgagcccag ctgccccag ggtggagggt
gcgtggacag ccggccaaga ggggcggggc cacagaaggc cctggcgagg
ccgtgggcc aagcagagga gcctacagtg gctggccaga cgggtcctag
gtgatgcaag gggtcctccg caccctgtt ctgtttcccc ggctctgacc
cagtgtgcgg cctctcctcc atgtctgtat gtggctgcct ccaaggcccc
tctcctcagg ccctgtatgt ccaagctggg cctccttcct ctgatcgccc
ttgggagagg tggcattgag gtcacctcct cccctcccag agtctgcatc
ttgtgggcaa atgccccagt gcctccacc atcctccatg catgcagctg
cctgcccagg tccctgtga acgcagccca gggccgtgca ggccacaggc
ggggctcatc tccccaggtg gggcctccaa gtctacacct gtggctggga
aggggagtca cagcacagat ggaatgaagc acatgagccc tgggtgtgga
cctgcctcag ctcagagcag cggtgggacc acatcttctc cctgccacag
gccaggtgac tagcacccaa gcccgtggca ctggcactgc tggggggcca
gggcggggctg tggccttgca aggagatgtg atttgctgtc aaagcacagc
tgccgcctcg gtgagtgact aatgagaact gaatgccgct cttattgctt
ttcactcgac taatttgtca gaggctgtca agagccaggg ggaggggca
gagggtgggg accggaggtc tgattgagtc accggcatgg gggcgaggct
gggtgccgg aggggtctgc aagaaaccag gagcacctgg caggaactca
gggccggtgg ggaccttggc catgatgtcg tgtgagagtc cggagggaca
caggagctgg ggtcaccctg tttgttccat atcaatggct ggtcagctct
tctaagcccc tactgtacac acacatgcac atgcatacat aggacacaca
cacacactta cacaaacaca cgcatgcatg catgtggaca taaaatcata
cactcacatg aataattta gaagcatgta caacacatgt acacgcagag
aagcactccc acacatgctt cctggcacac acacacac gcgcacacac
acacacctt gaatgcacac tctgtctccc acacagacac agaccagcga
aaactccagg ccaagctctg gtgcgtgggt tcccaagcct ggctgcacac
acaaccaggg tgctctcggc aattccagca tctccatacc cctggagcct
cttgtcctgg tgtgggcttc ctggtgatgt gggccagcca ggtatgggtg
gaaccgtcct actccccctc cagccccaag cctgagccag cctgagtctg
gcatggagct cctggagcca ggtgagcagt gagggcgct gggagctggg
gagatgccct gtgggtagga gatgcgcacc ccgcccaccc ggataccctt
cctcccagct gaatgcctgg ctgccaggga ccacggtgac ttctcttgct
tggctctgta acctgccccc ttcgtaccct ttccctccct ctgcctccac
ctctgcccga ctcggtccca caggaccctc tggccactgg atcccttcc
ctggaagcac ccctcactgc tcacctggct ccaggagctc catgccagac
tcaggctggc tcaggcttag ggctggaggg ggagtaggac ggttccaccc
atacctggct ggcccacatc accaggaagc ccacaccagg acaagaggct
ccagggtat ggagatgctg gaattgccga gagcaccctg gttgtgtgtg
```

*FIG. 11G*

```
cagccaggct tgggaaccca cgcaccagag cttggcctgg agttttcgct
ggtctgtgtc tgtgggcctt tgggggtccc acacacacaa ggggctcaag
gctgacccct cctcccacaa gggcctgcaa ctgctaatcc ctgatgcccc
ccactgtgtg gatggcaaaa ctgagtccag ggcccaaggg gctgagtcag
gaccctcttt tcggccccct acatggtggg tctcaacact gaggcagtcc
ctacaggcaa caaggatgga aggacagcac tggctgtcca ggctggaggg
actcagagag gaggccactg ggggactgcc tggaggagga gggcagcccg
ggcctgaggg cctggcagga tttggtgggg aagggaaagt ggagcccag
gtgggcagca gcagtagcag aaggggggca gggagccgtc tgtgggggac
agggagggtc cggctgcctg tccagggtgt ggaggaggag aggcagccca
caggctcaga gcccgaagga ggcgtggtgc ctgctctgcc ggcctcgctc
tgggcctgac ttccaaacac ccaattatcc ctaagtgcat ccgatcgact
ggcagggcgg ctgttccggg gcccacctcg tccatgcgct ccgcccgccc
tgctgtgggg ctccatctga tggcctcatt agggataatt gctctggcat
ttgggtctga cagggacggc ggattctgtc ctgtgttggg gcgtcttggt
tcttccagct tgggggatgg aggggagctg cttccttaca cggcagagaa
aggccctgca ccccaggcgg ggcaagatgg cgtgagggga ggatgcagga
ctcactgtcc cctgccttct tgggacaatg ggaactgagg gacagcccag
ggtggcatga caccccaaat cctcaggagg tcccccactg tctcccaaat
gtgagtgggg gtctgggagg ctgcaggccg gtgtccctgg gagccaggct
ctagaggggg catctctggg gaccctgggg accccgggct ataaagagaa
ctgcggagta gacatgggcg gggggcagt gtgtgctcca gcatgtgtgt
gtgtgtgtgc atgtacacgt gtgcacctgt atcgcctgtg tgtgtgcatg
tgatgtgtac acgtgtcatg catgcacgca catgtgtagt gtgtgctcgt
gtgtggtgtg tgcctgtgtc atgtatgagc acacttgtat atgttgtgtg
tactgtgtca tatatgagtg tgtttgcctg tgtagtgcat gcacatccgt
gtgtgcatct ggtgtgtccg tgggtcatta cgagtgcatc gtatgtgtat
cgtgtacatg agtacacttg tatgtgtggt gtgtacaggt gccatgtaag
tgtgcttgta catatatgca tgcatgtgtc atatgcatct gtgtgtgcat
gtgtgtggtg cacacatgtg ttatgtctga gtgtgcctgt atgtgtgcta
tgtacacgtc atgtgtgagt gtgcttgcat gtgcagtgtg tggatgctgc
ttgtacctgt ggtgtgtacc tgtgtcatgg gtgctcacac gtgcatggag
tgttgtgtgt gtgcttgtgt gccccatgtg tgcatgtgtg tgtgcctcac
acagatgcct gcatttgcct aggcacttgc aagaggacac catgctggct
ctcaaagatc acagggccac ctgagccctg tgcacaccac agccaggcca
tggctagacc ctgcagagcc acagggcgat gcctgtcagc caggggaccc
agaacacctc ctgggccct cccagcaca tggctgggct cctccagcag
gcctggattt gggaagggcc cgtggtgggc aaggctggtg ctggggagca
ggcctggtgg cctcagagac tcgccctgtg ggcggagcag cctcacagcc
aggttgaagt cagcactctg cccctgcccc acgcggggag cgggcaccag
tcccagggca cagacgtgct gggtgattaa tctgggtgat taagcctcgg
gctgagaggc tgttgagaga gaacacgctc cattgtggag ctggctcagc
attccttacg gccatggtgg caggggctgt aaccacaggg acggcggaag
tggtggaggg tggtggggta tggagggaag cccagagggc tctgtgcagg
aaggtggagc ctggtgcaat ggaggggaca gcaagggctc ctcagacctc
tgcggggccc ccactcccct ggtcacctgt tttgtctctg atctggcctg
ggtcggccct cactcctggc cccacctcat agccccccct ggtggggctc
```

*FIG. 11H*

```
cgctccagcc cttctccttc ccaggggcca gtatgctggc cccaggggtc
tcttggggcg tgacctcggc ctccagagaa ccctgtccca gctctgccct
tccctctggg gtctctgtag atgggacgct ggtcacagca gcctgtctga
tttgttccct gtggcctagg ttcctgagcc ccacagtgcc aggggatgga
tgccaccgga tctttgaaag accagtgtca ggccgggcgc agtggctcac
gcctgtaatc ccagcacttt gggaggccga ggtgggcgga tcacgaagtc
aggagatcga gaccatcctg gctaacacgg tgaaacccccg tctccactaa
aaatacaaaa agttagctgg gcgtggtggt gggcgcctgt agtcccagct
actcggggag ctgaggcagg agaatggcgt gaaccgggga ggcggagctt
gcagtgagcc gagatcgcgc cattgcactc cagcctgggt gacagagcga
gactcggtct caaaaaaaaa agaaaaaaag gaaagaccag tgtcttggga
gttgggaaac ctgggctgga gactcactgc atgacccctg agaagttgca
cctcagaacc tcagtcctcg catctgcaga atgggtctgt gaacacctca
gctgcccgaa cgtggatgcc gcaggctgac ccagcactga gctctaccaa
gaccaggggc cagccgtgtg ctccctccag gcctgtgccc agcgtggaga
ggcctcgtcc cgtgggcgct gggtggagc cttcctggtg tttgtggaca
tctctggaga gggccagagg caggtgggtg acacggggca tggctcaatc
atgggtggtc cagactggag aggtaccctc gggctgggag cggggaggct
ggccagggtg gactttcggg gcctccatgg ataccctcac catctggaat
cggagagggg cacggcacaa aggagggcgg ggccagggcc aggactggag
tcgggggcac ctctgtgcca acagggcct tggatctggg gtacagcatg
gttccccggc cctgaagggg ctggcgtgtg ggacaggctt cccaggaatg
gataggcagg gatggatgct gcctgattgg ggcgggaggc tggaggcagg
gcaggtgcag gcacctgagg gcagcactca cctccacagg ggtccagggg
cctccccagc ctcagtacct ggcctgggct cctgcctcca gagagcctgg
ccccaaggaa gagtctagta agcttagttc ccatcgggct tccatgaaag
cacaactggc ccggcaggaa accgaattaa aaagcaatat ttgtatcagt
ggaagacatt tgctgaaagg ttaaatccac atccggcagt gtggccatg
agcctccggc gtggtgttca tcaggcatgt ctctcctcct ggcctgggca
cctgagcact ggggctgccc tgggcagagc tggggcaggg tgctgggggg
cctggagctg cctcaccgag ggatcctcag cagccgaccc tggggaggc
aaatgagact ctttctgggg accttgaggg gagctcgggg gagccatgca
gagcttcacc aggcctggac actgggcatg gaggctgggc cacccaaggg
ccatcaccag ggactcaggt gggtgggcct cagccctggg tgacagaagc
tcacgggctg cagggcgagg ccagaggctg agccttcagg ctgaggtctt
ggaggcaaat ccctccaacg cccttctgag caggcaccca gacctactgt
gggcaggacc cacaggaggt ggaggccttt ggggaacacc gtggaggggc
atagcatctc cgagagagga cagggtctgc actgggtgct gagagacagc
aggggccgag cggtaggctt ccctgccccc agggatgttc cagggagcg
caagggaggg gcattaatat cgtggcaaga aagggcaggc attgcagagt
gagcagcgac ggaactgggt tttgtgggat gcataggagt tcacccggat
aagaggtggg tgaggaatga cactgcaaac cggggatcac ggagccccaa
atccttctgg gccaggaagt gggaagggtt gggggtctt cccttttgctt
tgactgagca ctcagcctgc ctgcagaggg cagcgaggag ccacggaggg
gtgtgggaca gggatgccat ggctgaagca gttttaggaa aggtcccagg
ggctattgtt gaagagagaa cggggagcgg ggagtcccac agctgacagg
```

*FIG. 11I*

```
agcagagtgg gccctgagag atgccagctc tgggtgccac agtgaccagc
cggggtaggc cttcgagaag tcagggagcg tctagggctt ctggctcctg
ctgggcccag ggtgtcatct tgggctgcca acaccagaaa gcccagcaga
tacaggaagc cccaagccct gtcggaaacg gttcttctcc aggagggaca
gcggtggcag cgttcagccg caggccatgc actctggggc cacgtccttc
cctctgtaca gtccagcatt gtcaaggcgg gctctggcca tctctgctga
ccccagaggg atggggaggc ctcccctcc accagaaggg ccagaagcca
ccctgggcag gggcatcact ctccctgggt ggggcagcgg cggggagcag
gaggtgccag tgggcgtggg ctggatgcgg gtgcctgcgg ggcggacatg
gaacttgggg gaggctctag gctggggttg tcctcaaggg agttctcagg
tcaccccagg gtcaccctca acccggggcc tggtggggta gaggagaaac
tgcaaaggtc tctccaaggg gaaggcatca gggccctcag cactgaggga
cgtgcgtgct cttcaaagaa ggggccacag gaccccgagg gaagccagga
gctagcagtg ggccatagag gggctgagtg gggtgggtgg aagccgtccc
tggccctggt cgccctggca acctggtgg ggactgtgat gcaggaggtg
gcagccattt ggaaacgcgt ggcgtctcct tagagatgtc ttcttcagcc
tcccagggtc ctccacactg gacaggtggg ccctcctggg acattctgga
ccccacaggg cgagcttggg aagccgctgc aagggccaca cctgcagggc
ccggggctg tgggcagatg gcactcctag gaaccacgtc tacaagacac
acggcctgga atcttctgga gaagcaaaca aattgcctcc tgacatctga
ggctggaggc tggattcccc gtcttggggc tttctgggtc ggtctgccac
gaggttctgg tgttcattaa aagtgtgccc ctgggctgcc agaaagcccc
tccctgtgtg ctctcttgag ggctgtgggg ccaaggggac cctggctgtc
tcagccccc gcagagcacg agccctggt ccccgcaagc ccgcgggctg
aggatgattc agacagggct gggagtgaa ggcaattaga ttccacggac
gagccctttc tcctgcgcct ccctccttcc tcacccaccc ccgcctccat
caggcacagc aggcaggggt ggggatgta aggaggggaa ggtgggggac
ccagaggggg ctttgacgtc agctcagctt ataagaggct gctgggccag
ggctgtggag acggagcccg gatccaccgg tcgccaccat ggtgagcaag
ggcgaggagc tgttcaccgg ggtggtgccc atcctggtcg agctggacgg
cgacgtaaac ggccacaagt tcagcgtgtc cggcgagggc gagggcgatg
ccacctacgg caagctgacc ctgaagttca tctgcaccac cggcaagctg
cccgtgccct ggcccaccct cgtgaccacc ctgacctacg gcgtgcagtg
cttcagccgc taccccgacc acatgaagca gcacgacttc ttcaagtccg
ccatgcccga aggctacgtc caggagcgca ccatcttctt caaggacgac
ggcaactaca agacccgcgc cgaggtgaag ttcgagggcg acaccctggt
gaaccgcatc gagctgaagg gcatcgactt caaggaggac ggcaacatcc
tggggcacaa gctggagtac aactacaaca gccacaacgt ctatatcatg
gccgacaagc agaagaacgg catcaaggtg aacttcaaga tccgccacaa
catcgaggac ggcagcgtgc agctcgccga ccactaccag cagaacaccc
ccatcggcga cggccccgtg ctgctgcccg acaaccacta cctgagcacc
cagtccgccc tgagcaaaga ccccaacgag aagcgcgatc acatggtcct
gctggagttc gtgaccgccg ccgggatcac tctcggcatg gacgagctgt
acaagtaaag cggccggccg cgactctagc tagatcataa tcagccatac
cacatttgta gaggttttac ttgctttaaa aaacctccca cacctccccc
tgaacctgaa acataaaatg aatgcaattg ttgttgttaa cttgtttatt
```

*FIG. 11J*

```
gcagcttata atggttacaa ataaagcaat agcatcacaa atttcacaaa
taaagcattt ttttcactgc attctagttg tggtttgtcc aaactcatca
atgtatc
```
12007

FIG. 11K

SEQUENCE LISTING

<160> NUMBER OF SEQ ID NOS: 38

<210> SEQ ID NO 1
<211> LENGTH: 10828
<212> TYPE: DNA
<213> ORGANISM: Homo sapiens

<400> SEQUENCE: 1

| | | | | | |
|---|---|---|---|---|---|
| tcgacgtgaa | cgaatcggtc | acacacacgc | agaaaggtgc | cgctgctggg | gacctgtggg | 60 |
| gcggggcgg | ggcagaagga | aggtcccctg | tttgggggac | cctttattaa | aaacaggcgg | 120 |
| caagctgagg | cgtccagctg | agttcatccc | aggccccaaa | gtaatcgcac | ggccaataag | 180 |
| ccctgcctaa | gatgaggacg | ggtggtctg | gaccgaggcc | ctggcgggag | ggagggtcct | 240 |
| gggcgtgcca | ccagctctcc | ggtcggaagc | ttctgcatgg | gccgtgccct | gcgctgggag | 300 |
| actcctgccc | gggcagcctt | gctccaaggt | cggctccaca | gaggtgccc | gccctctcag | 360 |
| ccctggcctg | tggcacctgc | ccacagccct | tcttccctg | gatgcagttt | tgccccctc | 420 |
| tgtgtcctcg | gctgcacgag | taggggcttt | cttgggttgg | ctgcccgcct | ggcccggact | 480 |
| gacccggact | ggctgaggct | gaggctgaca | gtgcagggaa | ggagccagaa | gccactatgg | 540 |
| ctgctgtgca | gagaccaagg | tgtctcccta | cacctgtggc | cccagggcc | ccagggacac | 600 |
| agggtccaca | ccctgcccca | cctgctccat | ctccgggacg | ccctcgctcc | ccaatctgat | 660 |
| tgcacagggt | gggggggccca | gcagccttgg | tgacagttct | tcatcccaag | ggcccgccca | 720 |
| gtttctcctg | gctcctgggg | atgggagtgg | cctgggttgt | ggccccacca | gctctgtgac | 780 |
| agggctcttg | atgcttctca | ggccctagtt | tccctgagac | ctgctggcca | ggagctcagg | 840 |
| cctcctggtt | tctggttact | tttcctcccc | tagaaagcag | ccttggcaga | cagaacagag | 900 |
| gcccagaaga | tcccgggagg | ctccccaggc | ccagaatctg | gggaacttgc | aaggatttgg | 960 |
| aatcctggcc | gggtgtggta | gccgagcctg | taatcccaga | atttggggag | gctaaggtgg | 1020 |
| gaggattact | tgaggccagg | agattgagac | cagcctgggc | aacacagtga | gaccccctct | 1080 |
| ctacaaaaaa | attttaaaa | atagccaggc | gtgctggtgt | gcccctgcag | ctccagctac | 1140 |
| ttggagggct | gaaatgggag | gatggcttga | gcccggagg | tcaaggctgc | agtgagccat | 1200 |
| gatcaagcca | ctgcacttca | gcctgggtga | caaagaccct | gtctctcaaa | ataaacattt | 1260 |
| aaaaaataga | agttaaatcc | tcttttggag | actgtgggt | gaggggagtg | tggccacacc | 1320 |
| acagcccttc | cacctcccca | ttgtgtgccc | cgaactgtgc | tgtgctggcc | actggcctca | 1380 |
| ccctccctga | agcatggcag | gtcccccacc | cccaaggcca | tgctgggtg | gggacagggg | 1440 |
| ccatgtgctt | cccacttgga | ggggctgtt | ccagacacct | ccctgccgc | ccctggcagg | 1500 |
| gtctcggctg | tactggatgt | gaggaccgtg | ggcctcccctt | ccccagact | atgagagcct | 1560 |
| ccaaaattgg | gaccgtgctg | tttcccttc | cgtgctgttt | cccaagggc | acccaggaaa | 1620 |
| tgcttgctgc | gtgaatcagt | gaatgagtga | gttcattcac | ctgggggctg | ggtggggacg | 1680 |
| atggagcctt | ccagcctcct | gggacctgcc | ctcagtgtgg | aaagtgagga | ggcatctgtc | 1740 |
| ttcctgagga | aaacctgggc | ttagtcctcc | ctctggccca | ggaggggacc | ggaccccaca | 1800 |
| gctgagggga | gccggcttag | ctgacagcga | gtgtattaaa | aacaagcttt | ggagcaaagc | 1860 |
| ggacaagctc | agtgttggt | agagttcatc | ccaggcccca | agtaatcac | atggcaaaca | 1920 |
| agccctgtct | aaatatcacg | gcggctgggg | cagcggcacg | cagcggcctg | gaaatgtcag | 1980 |
| ccggggtgg | gggctcctcc | gagccccggg | attagcagag | gtacctgaag | tgaatgcgcc | 2040 |

```
cacctcctcc ttcctgctcc tgctcaggac ctgggctggg ccagcccggg gcacctgggg    2100
aggggctcag agggtctcac tggggccagg ggctcttctt tcagcccag cccgggctgg      2160 ttcccatggg gtagcaggct gaggagagtg gggagactga gcttggccgg agtggggcgg     2220
acgcacttcc aggcccaaac cagcagccca cgggtggggg cagagaaagc tgccccctg     2280 caggcccagt gagtcctcga gagagggggc cacccggcca tggggggtg gtgatgttgg     2340 ttcggggaac ctagggcatc tggaccagcc cctggacaag gcggtcacag cagccactgc    2400
ctgagcaggc cacctgcggg cttccctcca ggtctgccca tcggctcagg gcttccagag    2460
cccaagggag caacacgttt ctcctgagca cgggtggagg gaaaataagg atgtttacga    2520
tcgagttgcc catggaagcg ttaccaagcc ccctggagac tcatctcacc gcagtgggac    2580 cttttgcattc tctcaggcgg tgggggtctc tgccgtgttg tccgtaaagt gtcagcgtgg   2640
ggccaactgg ggacctcagc agccacgtcc aaccctcatc tgaaacaaga actggaggcc   2700
tgggctgctc ctcccttccc gccctcagga gcacagggtg gcaggaggtg aactccatgg   2760 gcgagggct cttgctcttg caggccccca aagtcagtca ggtgcagaag gaaggacag     2820 gattcaggga caggagacac acagggggtc ccctctgttc caggatgctc ccaaatctga   2880
gcccagctgc ccccagggtg gagggtgcgt ggacagccgg ccaagagggg cggggccaca   2940
gaaggccctg gcgaggccgt ggggccaagc agaggagcct acagtggctg ccagacgggg   3000
tcctaggtga tgcaagggt cctccgcacc cctgttctgt ttccccggct ctgacccagt    3060
gtgcggcctc tcctccatgt ctgtatgtgg ctgcctccaa ggcccctctc ctcaggccct   3120
gtatgtccaa gctgggcctc cttcctctga tcgcccttgg gagaggtggc attgaggtca   3180
cctcctcccc tcccagagtc tgcatcttgt gggcaaatgc cccagtgcct cccaccatcc   3240
tccatgcatg cagctgcctg cccaggtccc ctgtgaacgc agcccagggc cgtgcaggcc   3300
acaggcgggc tcatctccc caggtggggc ctccaagtct acacctgtgg ctgggaaggg    3360
gagtcacagc acagatggaa tgaagcacat gagccctggg tgtggacctg cctcagctca   3420
gagcagcggt gggaccacat cttctccctg ccacaggcca ggtgactagc acccaagccc    3480
gtggcactgg cactgctggg gggccagggc gggctgtggc cttgcaagga gatgtgattt    3540
gctgtcaaag cacagctgcc gcctcggtga gtgactaatg agaactgaat gccgctctta    3600
ttgcttttca ctcgactaat ttgtcagagg ctgtcaagag ccaggggag ggggcagagg    3660 gtggggaccg gaggtctgat tgagtcaccg gcatggggc gaggctgggt gcccggaggg    3720
gtctgcaaga aaccaggagc acctggcagg aactcagggc cggtggggac cttggccatg    3780
atgtcgtgtg agagtccgga gggacacagg agctgggtc accctgtttg ttccatatca    3840
atggctggtc agctcttcta agcccctact gtacacacac atgcacatgc atacatagga    3900
cacacacaca cacttacaca aacacacgca tgcatgcatg tggacataaa atcatacact    3960
cacatgaata attttagaag catgtacaac acatgtacac gcagagaagc actcccacac   4020
atgcttcctg gcacacacac acacgcgcgc acacacacac acccttgaat gcacactctg    4080
tctcccacac agacacagac cagcgaaaac tccaggccaa gctctggtgc gtgggttccc   4140
aagcctggct gcacacacaa ccagggtgct ctcggcaatt ccagcatctc catacccctg   4200
gagcctcttg tcctggtgtg ggcttcctgg tgatgtgggc cagccaggta tgggtggaac   4260
cgtcctactc ccctccagc cccaagcctg agcagcctg agtctggcat ggagctcctg    4320
gagccaggtg agcagtgagg ggcgctggga gctggggaga tgccctgtgg gtaggagatg    4380
```

-continued

```
cgcaccccgc caccccggat acccttcctc ccagctgaat gcctggctgc cagggaccac    4440
ggtgacttct cttgcttggc tctgtaacct gccccctttcg tacccttttcc ctccctctgc    4500 ctccacctct gcccgactcg gtcccacagg accctctggc cactggatcc ccttccctgg    4560
aagcacccct cactgctcac ctggctccag gagctccatg ccagactcag gctggctcag    4620
gcttagggct ggaggggag taggacggtt ccacccatac ctggctggcc cacatcacca    4680
ggaagcccac accaggacaa gaggctccag gggtatggag atgctggaat tgccgagagc    4740
accctggttg tgtgtgcagc caggcttggg aacccacgca ccagagcttg gcctggagtt    4800
ttcgctggtc tgtgtctgtg ggcctttggg gtcccacac acacaagggg ctcaaggctg    4860
acccctcctc ccacaagggc ctgcaactgc taatccctga tgcccccac tgtgtggatg    4920 gcaaaactga gtccagggcc caaggggctg agtcaggacc ctcttttcgg cccctacat    4980 ggtgggtctc aacactgagg cagtccctac aggcaacaag gatggaagga cagcactggc    5040
tgtccaggct ggagggactc agagaggagg ccactggggg actgcctgga ggaggagggc    5100
agcccgggcc tgagggcctg gcaggatttg gtggggaagg gaaagtggag ccccaggtgg    5160
gcagcagcag tagcagaagg ggggcaggga gccgtctgtg ggggacaggg agggtccggc    5220
tgcctgtcca gggtgtggag gaggagaggc agcccacagg ctcagagccc gaaggaggcg    5280
tggtgcctgc tctgccggcc tcgctctggg cctgacttcc aaacacccaa ttatccctaa    5340
gtgcatccga tcgactggca gggcggctgt tccggggccc acctcgtcca tgcgctccgc    5400
ccgccctgct gtgggctcc atctgatggc ctcattaggg ataattgctc tggcatttgg    5460
gtctgacagg gacggcggat tctgtcctgt gttgggcgt cttggttctt ccagcttggg    5520
ggatggaggg gagctgcttc cttacacggc agagaaaggc cctgcacccc aggcggggca    5580
agatggcgtg agggaggat gcaggactca ctgtcccctg ccttcttggg acaatgggaa    5640
ctgagggaca gcccagggtg gcatgacacc ccaaatcctc aggaggtccc ccactgtctc    5700
ccaaatgtga gtgggggtct gggaggctgc aggccggtgt ccctgggagc caggctctag    5760 aggggggcatc tctgggggacc ctggggaccc cgggctataa agagaactgc ggagtagaca    5820 tgggcgggggg ggcagtgtgt gctccagcat gtgtgtgtgt gtgtgcatgt acacgtgtgc    5880
acctgtatcg cctgtgtgtg tgcatgtgat gtgtacacgt gtcatgcatg cacgcacatg    5940
tgtagtgtgt gctcgtgtgt ggtgtgtgcc tgtgtcatgt atgagcacac ttgtatatgt    6000
tgtgtgtact gtgtcatata tgagtgtgtt tgcctgtgta gtgcatgcac atccgtgtgt    6060
gcatctggtg tgtccgtggg tcattacgag tgcatcgtat gtgtatcgtg tacatgagta    6120
cacttgtatg tgtggtgtgt acaggtgcca tgtaagtgtg cttgtacata tatgcatgca    6180
tgtgtcatat gcatctgtgt gtgcatgtgt gtggtgcaca catgtgttat gtctgagtgt    6240
gcctgtatgt gtgctatgta cacgtcatgt gtgagtgtgc ttgcatgtgc agtgtgtgga    6300
tgctgcttgt acctgtggtg tgtacctgtg tcatgggtgt tcacacgtgc atggagtgtt    6360
gtgtgtgtgc ttgtgtgccc catgtgtgca tgtgtgtgtg cctcacacag atgcctgcat    6420
ttgcctaggc acttgcaaga ggacaccatg ctggctctca aagatcacag gccacctga    6480 gccctgtgca caccacagcc aggccatggc tagaccctgc agagccacag ggcgatgcct    6540
gtcagccagg ggaccagaa cacctcctgg gcccctcccc agcacatggc tgggctcctc    6600
cagcaggcct ggatttggga agggcccgtg gtgggcaagg ctggtgctgg ggagcaggcc    6660
tggtggcctc agagactcgc cctgtgggcg gagcagcctc acagccaggt tgaagtcagc    6720
actctgcccc tgcccacgc ggggagcggg caccagtccc agggcacaga cgtgctgggt    6780
```

-continued

```
gattaatctg ggtgattaag cctcgggctg agaggctgtt gagagagaac acgctccatt    6840
gtggagctgg ctcagcattc cttacggcca tggtggcagg ggctgtaacc acagggacgg    6900
cggaagtggt ggagggtggt gggtatgga ggaagcca gagggctctg tgcaggaagg       6960
tggagcctgg tgcaatggag gggacagcaa gggctcctca gacctctgcg ggcccccac     7020
tcccctggtc acctgttttg tctctgatct ggcctgggtc ggccctcact cctgcccca     7080
cctcatagcc ccccctggtg gggctccgct ccagcccttc tccttcccag gggccagtat    7140
gctggcccca gggtctcttt ggggcgtgac ctcggcctcc agagaaccct gtcccagctc    7200
tgcccttccc tctggggtct ctgtagatgg gacgctggtc acagcagcct gtctgatttg    7260
ttccctgtgg cctaggttcc tgagccccac agtgccaggg gatggatgcc accggatctt    7320
tgaaagacca gtgtcaggcc gggcgcagtg gctcacgcct gtaatcccag cactttggga    7380
ggccgaggtg ggcggatcac gaagtcagga gatcgagacc atcctggcta acacggtgaa    7440
accccgtctc cactaaaaat acaaaaagtt agctgggcgt ggtggtgggc gcctgtagtc    7500
ccagctactc gggaggctga ggcaggagaa tggcgtgaac cggggaggcg gagcttgcag    7560
tgagccgaga tcgcgccatt gcactccagc ctgggtgaca gagcgagact cggtctcaaa    7620
aaaaaagaa aaaaggaaa gaccagtgtc ttgggagttg ggaaacctgg gctggagact    7680
cactgcatga cccсctgagaa gttgcacctc agaacctcag tcctcgcatc tgcagaatgg    7740
gtctgtgaac acctcagctg cccgaacgtg gatgccgcag gctgacccag cactgagctc    7800
taccaagacc aggggccagc cgtgtgctcc ctccaggcct gtgcccagcg tggagaggcc    7860
tcgtcccgtg ggcgctgggg tggagccttc ctggtgtttg tggacatctc tggagagggc    7920
cagaggcagg tgggtgacac ggggcatggc tcaatcatgg gtggtccaga ctggagaggt    7980
accctcgggc tgggagcggg gaggctggcc agggtggact ttcggggcct ccatggatac    8040
cctcaccatc tggaatcgga gagggcacg gcacaaagga gggcggggcc agggccagga     8100
ctggagtcgg gggcacctct gtgccaacag gggccttgga tctggggtac agcatggttc    8160
cccgcccctc aaggggctgg cgtgtgggac aggcttccca ggaatggata ggcagggatg    8220
gatgctgcct gattggggcg ggaggctgga ggcagggcag gtgcaggcac ctgagggcag    8280
cactcacctc cacaggggtc cagggccctc cccagcctca gtacctggcc tgggctcctg    8340
cctccagaga gcctggcccc aaggaagagt ctagtaagct tagttcccat cgggcttcca    8400
tgaaagcaca actgggccgg caggaaaccg aattaaaaag caatatttgt atcagtggaa    8460
gacatttgct gaaaggttaa atccacatcc ggcagtgtgg gccatgagcc tccggcgtgg    8520
tgttcatcag gcatgtctct cctcctggcc tgggcacctg agcactgggg ctgccctggg    8580
cagagctggg gcagggtgct ggggggcctg gagctgcctc accgagggat cctcagcagc    8640
cgaccctggg ggaggcaaat gagactctttt ctggggacct tgaggggagc tcgggggagc    8700
catgcagagc ttcaccaggc ctggacactg gcatggagg ctgggccacc caagggccat    8760
caccagggac tcaggtgggt gggcctcagc cctgggtgac agaagctcac gggctgcagg    8820
gcgaggccag aggctgagcc ttcaggctga ggtcttggag gcaaatccct ccaacgccct    8880
tctgagcagg cacccagacc tactgtgggc aggaccaca ggaggtggag cctttgggg    8940
aacaccgtgg aggggcatag catctccgag agaggacagg gtctgcactg ggtgctgaga    9000
gacagcaggg gccgagcggt aggcttccct gccccaggg atgttccagg ggagcgcaag    9060
ggaggggcat taatatcgtg gcaagaaagg gcaggcattg cagagtgagc agcgacggaa    9120
```

```
ctgggttttg tgggatgcat aggagttcac ccggataaga ggtgggtgag gaatgacact    9180
gcaaaccggg gatcacggag ccccaaatcc ttctgggcca ggaagtggga agggttgggg    9240
ggtcttccct ttgctttgac tgagcactca gcctgcctgc agagggcagc gaggagccac    9300
ggaggggtgt gggacaggga tgccatggct gaagcagttt taggaaaggt cccagggggct   9360 attgttgaag agagaacggg gagcggggag tcccacagct gacaggagca gagtgggccc    9420
tgagagatgc cagctctggg tgccacagtg accagccggg gtaggccttc gagaagtcag    9480
ggagcgtcta gggcttctgg ctcctgctgg gcccagggtg tcatcttggg ctgccaacac    9540
cagaaagccc agcagataca ggaagcccca agccctgtcg gaaacggttc ttctccagga    9600
gggacagcgg tggcagcgtt cagccgcagg ccatgcactc tggggccacg tccttccctc    9660
tgtacagtcc agcattgtca aggcgggctc tggccatctc tgctgacccc agagggatgg    9720
ggaggcctcc ccttccacca gaagggccag aagccaccct gggcaggggc atcactctcc    9780
ctgggtgggg cagcggcggg gagcaggagg tgccagtggg cgtgggctgg atgcgggtgc    9840
ctgcggggcg gacatggaac ttgggggagg ctctaggctg gggttgtcct caagggagtt    9900
ctcaggtcac cccagggtca ccctcaaccc ggggcctggt ggggtagagg agaaactgca    9960
aaggtctctc caaggggaag gcatcagggc cctcagcact gagggacgtg cgtgctcttc   10020
aaagaagggg ccacaggacc ccgagggaag ccaggagcta gcagtgggcc atagagggc    10080 tgagtggggt gggtggaagc cgtccctggc cctggtcgcc ctggcaaccc tggtggggac   10140
tgtgatgcag gaggtggcag ccatttggaa acgcgtggcg tctccttaga gatgtcttct   10200
tcagcctccc agggtcctcc acactggaca ggtgggccct cctgggacat tctggacccc   10260
acagggcgag cttgggaagc cgctgcaagg gccacacctg cagggcccgg gggctgtggg   10320
cagatggcac tcctaggaac cacgtctaca agacacacgg cctggaatct tctggagaag   10380
caaacaaatt gcctcctgac atctgaggct ggaggctgga ttccccgtct tggggctttc   10440
tgggtcggtc tgccacgagg ttctggtgtt cattaaaagt gtgcccctgg gctgccagaa   10500
agcccctccc tgtgtgctct cttgagggct gtggggccaa ggggaccctg gctgtctcag   10560
ccccccgcag agcacgagcc cctggtcccc gcaagcccgc gggctgagga tgattcagac   10620
agggctgggg agtgaaggca attagattcc acggacgagc cctttctcct gcgcctccct   10680
ccttcctcac ccacccccgc ctccatcagg cacagcaggc agggtggggg gatgtaagga   10740
ggggaaggtg ggggacccag aggggggcttt gacgtcagct cagcttataa gaggctgctg   10800
ggccagggct gtggagacgg agcccgga                                     10828
```

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agacggagcc cgg                                                        13

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 3
atgcccaccc                                                              10

<210> SEQ ID NO 4
<211> LENGTH: 10
<212> TYPE: DNA
<213> ORGANISM: Homo sapiens

<400> SEQUENCE: 4
ctgtggggcg                                                              10

<210> SEQ ID NO 5
<211> LENGTH: 10
<212> TYPE: DNA
<213> ORGANISM: Homo sapiens

<400> SEQUENCE: 5
gcgtggggcg                                                              10

<210> SEQ ID NO 6
<211> LENGTH: 10
<212> TYPE: DNA
<213> ORGANISM: Homo sapiens

<400> SEQUENCE: 6
gagtggggcg                                                              10

<210> SEQ ID NO 7
<211> LENGTH: 10
<212> TYPE: DNA
<213> ORGANISM: Homo sapiens

<400> SEQUENCE: 7
gcgtggggcc                                                              10

<210> SEQ ID NO 8
<211> LENGTH: 10
<212> TYPE: DNA
<213> ORGANISM: Homo sapiens

<400> SEQUENCE: 8
gcgtggggca                                                              10

<210> SEQ ID NO 9
<211> LENGTH: 10
<212> TYPE: DNA
<213> ORGANISM: Homo sapiens

<400> SEQUENCE: 9
gattggggcg                                                              10

<210> SEQ ID NO 10
<211> LENGTH: 11
<212> TYPE: DNA
<213> ORGANISM: Homo sapiens

<400> SEQUENCE: 10
gcgtggtggc g                                                            11

<210> SEQ ID NO 11
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: Unknown nucleic acid
<220> FEATURE:
<221> NAME/KEY: modified_base
<222> LOCATION: (4)
<223> OTHER INFORMATION: Unknown nucleic acid
<220> FEATURE:
<221> NAME/KEY: modified_base
<222> LOCATION: (7)
<223> OTHER INFORMATION: Unknown nucleic acid
<220> FEATURE:
<221> NAME/KEY: modified_base
<222> LOCATION: (9)..(18)
<223> OTHER INFORMATION: Unknown nucleic acid
<220> FEATURE:
<221> NAME/KEY: modified_base
<222> LOCATION: (20)..(21)
<223> OTHER INFORMATION: Unknown nucleic acid

<400> SEQUENCE: 11
gnantgncnn nnnnnnnnan n                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttcagcacca cggacagcgc c                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: Unknown nucleic acid
<220> FEATURE:
<221> NAME/KEY: modified_base
<222> LOCATION: (8)
<223> OTHER INFORMATION: Unknown nucleic acid
<220> FEATURE:
<221> NAME/KEY: modified_base
<222> LOCATION: (12)..(21)
<223> OTHER INFORMATION: Unknown nucleic acid

<400> SEQUENCE: 13
nnnnnngntc gnnnnnnnnn n                                              21

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtgatattta cctccaaatg ccag                                           24
```

```
<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
taaatatcac                                                          10

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctggcatttg g                                                        11

<210> SEQ ID NO 17
<211> LENGTH: 18
<212> TYPE: DNA
<213> ORGANISM: Mus musculus
<220> FEATURE:
<221> NAME/KEY: modified_base
<222> LOCATION: (6)..(14)
<223> OTHER INFORMATION: Unknown nucleic acid

<400> SEQUENCE: 17
gtttcnnnnn nnnnttcc                                                 18

<210> SEQ ID NO 18
<211> LENGTH: 15
<212> TYPE: DNA
<213> ORGANISM: Rattus sp.

<400> SEQUENCE: 18
taattagatt attaa                                                    15

<210> SEQ ID NO 19
<211> LENGTH: 23
<212> TYPE: DNA
<213> ORGANISM: Homo sapiens
<220> FEATURE:
<221> NAME/KEY: modified_base
<222> LOCATION: (7)..(15)
<223> OTHER INFORMATION: Unknown nucleic acid

<400> SEQUENCE: 19
gaaggcnnnn nnnnnccacg gac                                           23

<210> SEQ ID NO 20
<211> LENGTH: 21
<212> TYPE: DNA
<213> ORGANISM: Mus musculus
<220> FEATURE:
<221> NAME/KEY: modified_base
<222> LOCATION: (7)..(14)
<223> OTHER INFORMATION: Unknown nucleic acid

<400> SEQUENCE: 20
ggatgcnnnn nnnnctaatg g                                             21
```

```
<210> SEQ ID NO 21
<211> LENGTH: 20
<212> TYPE: DNA
<213> ORGANISM: Rattus sp.
<220> FEATURE:
<221> NAME/KEY: modified_base
<222> LOCATION: (7)..(14)
<223> OTHER INFORMATION: Unknown nucleic acid

<400> SEQUENCE: 21
ggatgcnnnn nnnnctaatg                                           20

<210> SEQ ID NO 22
<211> LENGTH: 17
<212> TYPE: DNA
<213> ORGANISM: Homo sapiens
<220> FEATURE:
<221> NAME/KEY: modified_base
<222> LOCATION: (6)..(12)
<223> OTHER INFORMATION: Unknown nucleic acid

<400> SEQUENCE: 22
tacctnnnnn nntgaca                                              17

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 23
ggaaacagct atgaccatg                                            19

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 24
gacaggatcc gggctccgtc tccaca                                    26

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 25
gtcacccggg accgaataaa tacctgtgac g                              31

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 26
gtcacccggg ggatcatatc gtcaattatt acc                            33

<210> SEQ ID NO 27
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcctatgact ctcttaaggt agccaaaa                                           28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggcttttggc taccttaaga gagtcata                                           28

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agacggagcc cggatccacc ggtcgccacc atggtgag                                38

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gacagatctc cgggctccgt ctccaca                                            27

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tgtggagacg gagcccggac ctccacactg agccatgc                                38

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgtggagacg gagcccggag atctgtcaga tct                                     33

<210> SEQ ID NO 33
<211> LENGTH: 19
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 33
tgtggagacg gagcccgga                                                  19

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcgagccgcc acttaagggt gc                                              22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tcgagcaccc ttaagtggcg gc                                              22

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcatcgtcga caccgtac                                                   18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggtgtcgacg atgcgtac                                                   18

<210> SEQ ID NO 38
<211> LENGTH: 12007
<212> TYPE: DNA
<213> ORGANISM: Homo sapiens

<400> SEQUENCE: 38
ggccgcataa cttcgtatag catacattat acgaagttat ggatccaccc tctcttctca     60
tctctgagcc gggtgttccc aaacttccct cctggtctgt tcatccacca ggctctgagg    120
gccagccctg cctggcaagg ggggaaccaa ggggccaact ttagttttcc agaagcctct    180
gtccagggga ggagtcgacg tgaacgaatc ggtcacacac acgcagaaag gtgccgctgc    240
tggggacctg tggggcgggg gcggggcaga aggaaggtcc cctgtttggg ggacccttta    300

-continued

```
ttaaaaacag gcggcaagct gaggcgtcca gctgagttca tcccaggccc caaagtaatc      360
gcacggccaa taagccctgc ctaagatgag gacgggtggg tctggaccga ggccctggcg      420
ggagggaggg tcctgggcgt gccaccagct ctccggtcgg aagcttctgc atgggccgtg      480
ccctgcgctg ggagactcct gcccgggcag ccttgctcca aggtcggctc cacagagggt      540
gcccgccctc tcagccctgg cctgtggcac ctgcccacag ccctttcttc cctggatgca      600
gttttgccc cctctgtgtc ctcggctgca cgagtagggg cttcttggg ttggctgccc        660
gcctggcccg gactgacccg gactggctga ggctgaggct gacagtgcag ggaaggagcc      720
agaagccact atggctgctg tgcagagacc aaggtgtctc cctacacctg tggcccccag      780
ggccccaggg acacagggtc cacaccctgc cccacctgct ccatctccgg gacgccctcg      840
ctccccaatc tgattgcaca gggtgggggg cccagcagcc ttggtgacag ttcttcatcc      900
caagggcccg cccagtttct cctggctcct ggggatggga gtggcctggg ttgtggcccc      960
accagctctg tgacagggct cttgatgctt ctcaggccct agtttccctg agacctgctg     1020
gccaggagct caggcctcct ggtttctggt tacttttcct cccctagaaa gcagccttgg     1080
cagacagaac agaggcccag aagatcccgg gaggctcccc aggcccagaa tctggggaac     1140
ttgcaaggat ttggaatcct ggccgggtgt ggtagccgag cctgtaatcc cagaatttgg     1200
ggaggctaag gtgggaggat tacttgaggc caggagattg agaccagcct gggcaacaca     1260
gtgagacccc ctctctacaa aaaattttt aaaaatagcc aggcgtgctg gtgtgcccct      1320
gcagctccag ctacttggga ggctgaaatg ggaggatggc ttgagcccgg gaggtcaagg     1380
ctgcagtgag ccatgatcaa gccactgcac ttcagcctgg gtgacaaaga ccctgtctct     1440
caaaataaac atttaaaaaa tagaagttaa atcctctttt ggagactgtg gggtgagggg     1500
agtgtggcca caccacagcc cttccacctc cccattgtgt gccccgaact gtgctgtgct     1560
ggccactggc ctcaccctcc ctgaagcatg gcaggtcccc caccccaag gccatgctgg      1620
ggtggggaca ggggccatgt gcttcccact tggagggggc tgttccagac acctccctgg     1680
ccgcccctgg cagggtctcg gctgtactgg atgtgaggac cgtgggcctc ccttcccca      1740
gactatgaga gcctccaaaa ttgggaccgt gctgtttccc tttccgtgct gtttcccaaa     1800
gggcacccag gaaatgcttg ctgcgtgaat cagtgaatga gtgagttcat tcacctgggg     1860
gctgggtggg gacgatggag ccttccagcc tcctgggacc tgccctcagt gtggaaagtg     1920
aggaggcatc tgtcttcctg aggaaaacct gggcttagtc ctccctctgg cccaggaggg     1980
gaccggaccc cacagctgga gggagccggc ttagctgaca gcgagtgtat taaaaacaag     2040
ctttggagca aagcggacaa gctcaggtgt tggtagagtt catcccaggc cccaaagtaa     2100
tcacatggca aacaagccct gtctaaatat cacggcggct ggggcagcgg cacgcagcgg     2160
cctggaaatg tcagccgggg gtgggggctc ctccgagccc cggattagc agaggtacct      2220
gaagtgaatg cgcccacctc ctccttcctg ctcctgctca ggacctgggc tgggccagcc     2280
cggggcacct ggggagggc tcagagggtc tcactgggc cagggctct tctttcagcc       2340
ccagcccggg ctggttccca tgggtagca ggctgaggag agtgggggaga ctgagcttgg    2400
ccggagtggg gcggacgcac ttccaggccc aaaccagcag cccacgggtg gggcagaga     2460
aagctgcccc cctgcaggcc cagtgagtcc tcgagagagg gggccacccg gccatggggg    2520
ggtggtgatg ttggttcggg gaacctaggg catctggacc agccctggga caaggcggtc    2580
acagcagcca ctgcctgagc aggccacctg cgggcttccc tccaggtctg cccatcggct    2640
cagggcttcc agagcccaag ggagcaacac gtttctcctg agcacgggtg gagggaaaat    2700
```

-continued

```
aaggatgttt acgatcgagt tgcccatgga agcgttacca agcccctgg agactcatct      2760 caccgcagtg ggacctttgc attctctcag gcggtggggg tctctgccgt gttgtccgta     2820
aagtgtcagc gtggggccaa ctggggacct cagcagccac gtccaaccct catctgaaac     2880
aagaactgga ggcctgggct gctcctccct tcccgccctc aggagcacag ggtggcagga     2940
ggtgaactcc atgggcgagg ggctcttgct cttgcaggcc cccaaagtca gtcaggtgca     3000
gaagggaagg acaggattca gggacaggag acacacaggg ggtcccctct gttccaggat     3060
gctcccaaat ctgagcccag ctgccccag gtggaggt gcgtggacag ccggccaaga        3120 ggggcgggc cacagaaggc cctggcgagg ccgtggggcc aagcagagga gcctacagtg      3180
gctggccaga cgggtcctag gtgatgcaag gggtcctccg cacccctgtt ctgtttcccc     3240
ggctctgacc cagtgtgcgg cctctcctcc atgtctgtat gtggctgcct ccaaggcccc     3300
tctcctcagg ccctgtatgt ccaagctggg cctccttcct ctgatcgccc ttgggagagg     3360
tggcattgag gtcacctcct cccctcccag agtctgcatc ttgtgggcaa atgcccagt     3420 gcctcccacc atcctccatg catgcagctg cctgcccagg tcccctgtga acgcagccca     3480
gggccgtgca ggccacaggc ggggctcatc tccccaggtg gggcctccaa gtctacacct    3540
gtggctggga agggagtca cagcacagat ggaatgaagc acatgagccc tgggtgtgga    3600
cctgcctcag ctcagagcag cggtgggacc acatcttctc cctgccacag gccaggtgac    3660
tagcacccaa gcccgtggca ctggcactgc tggggggcca gggcgggctg tggccttgca    3720
aggagatgtg atttgctgtc aaagcacagc tgccgcctcg gtgagtgact aatgagaact    3780
gaatgccgct cttattgctt ttcactcgac taatttgtca gaggctgtca agagccaggg    3840 ggaggggca gagggtgggg accggaggtc tgattgagtc accggcatgg gggcgaggct     3900
gggtgcccgg aggggtctgc aagaaaccag gagcacctgg caggaactca gggccggtgg    3960
ggaccttggc catgatgtcg tgtgagagtc cggaggaca caggagctgg ggtcaccctg     4020
tttgttccat atcaatggct ggtcagctct tctaagcccc tactgtacac acacatgcac    4080
atgcatacat aggacacaca cacacactta cacaaacaca cgcatgcatg catgtggaca    4140
taaaatcata cactcacatg aataattta gaagcatgta caacacatgt acgcagag      4200 aagcactccc acacatgctt cctggcacac acacacacac gcgcacacac acacacccctt  4260 gaatgcacac tctgtctccc acacagacac agaccagcga aaactccagg ccaagctctg    4320
gtgcgtgggt tccaagcct ggctgcacac acaaccaggg tgctctcggc aattccagca     4380
tctccatacc cctggagcct cttgtcctgg tgtgggcttc ctggtgatgt gggccagcca    4440
ggtatgggtg gaaccgtcct actccccctc cagccccaag cctgagccag cctgagtctg    4500
gcatggagct cctggagcca ggtgagcagt gaggggcgct gggagctggg gagatgccct    4560
gtgggtagga gatgcgcacc ccgcccaccc ggataccctt cctcccagct gaatgcctgg    4620
ctgccaggga ccacggtgac ttctcttgct tggctctgta acctgccccc ttcgtaccct    4680
ttccctccct ctgcctccac ctctgcccga ctcggtccca caggaccctc tggccactgg    4740
atccccttcc ctggaagcac ccctcactgc tcacctggct ccaggagctc catgccagac    4800
tcaggctggc tcaggcttag ggctggaggg ggagtaggac ggttccaccc atacctggct    4860
ggcccacatc accaggaagc ccacaccagg acaagaggcc caggggtat ggagatgctg     4920 gaattgccga gagcaccctg gttgtgtgtg cagccaggct tggaaccca cgcaccagag     4980 cttggcctgg agttttcgct ggtctgtgtc tgtgggcctt tggggtccc acacacacaa    5040
```

```
ggggctcaag gctgacccct cctcccacaa gggcctgcaa ctgctaatcc ctgatgcccc    5100
ccactgtgtg gatggcaaaa ctgagtccag ggcccaaggg gctgagtcag gaccctcttt    5160 tcggcccccct acatggtggg tctcaacact gaggcagtcc ctacaggcaa caaggatgga   5220
aggacagcac tggctgtcca ggctggaggg actcagagag gaggccactg ggggactgcc    5280
tggaggagga gggcagcccg ggcctgaggg cctggcagga tttggtgggg aagggaaagt    5340 ggagcccag gtgggcagca gcagtagcag aagggggca gggagccgtc tgtgggggac      5400
agggagggtc cggctgcctg tccagggtgt ggaggaggag aggcagccca caggctcaga    5460
gcccgaagga ggcgtggtgc ctgctctgcc ggcctcgctc tgggcctgac ttccaaacac    5520
ccaattatcc ctaagtgcat ccgatcgact ggcagggcgg ctgttccggg gcccacctcg    5580
tccatgcgct ccgcccgccc tgctgtgggg ctccatctga tggcctcatt agggataatt    5640
gctctggcat ttgggtctga cagggacggc ggattctgtc ctgtgttggg gcgtcttggt    5700
tcttccagct tgggggatgg aggggagctg cttccttaca cggcagagaa aggccctgca    5760
ccccaggcgg ggcaagatgg cgtgagggga ggatgcagga ctcactgtcc cctgccttct    5820
tgggacaatg ggaactgagg gacagcccag ggtggcatga caccccaaat cctcaggagg    5880
tcccccactg tctcccaaat gtgagtgggg gtctgggagg ctgcaggccg tgtccctgg     5940 gagccaggct ctagagggg catctctggg gaccctgggg accccgggct ataaagagaa     6000
ctgcggagta gacatgggcg gggggcagt gtgtgctcca gcatgtgtgt gtgtgtgtgc     6060
atgtacacgt gtgcacctgt atcgcctgtg tgtgtgcatg tgatgtgtac acgtgtcatg   6120
catgcacgca catgtgtagt gtgtgctcgt gtgtggtgtg tgcctgtgtc atgtatgagc   6180
acacttgtat atgttgtgtg tactgtgtca tatatgagtg tgtttgcctg tgtagtgcat   6240
gcacatccgt gtgtgcatct ggtgtgtccg tgggtcatta cgagtgcatc gtatgtgtat    6300
cgtgtacatg agtacacttg tatgtgtggt gtgtacaggt gccatgtaag tgtgcttgta    6360
catatatgca tgcatgtgtc atatgcatct gtgtgtgcat gtgtgtggtg cacacatgtg    6420
ttatgtctga gtgtgcctgt atgtgtgcta tgtacacgtc atgtgtgagt gtgcttgcat    6480
gtgcagtgtg tggatgctgc ttgtacctgt ggtgtgtacc tgtgtcatgg gtgctcacac    6540
gtgcatggag tgttgtgtgt gtgcttgtgt gccccatgtg tgcatgtgtg tgtgcctcac    6600
acagatgcct gcatttgcct aggcacttgc aagaggacac catgctggct ctcaaagatc    6660
acagggccac ctgagccctg tgcacaccac agccaggcca tggctagacc ctgcagagcc    6720 acaggcgat gcctgtcagc caggggaccc agaacacctc ctgggcccct ccccagcaca     6780
tggctgggct cctccagcag gcctggattt gggaagggcc cgtggtgggc aaggctggtg    6840
ctggggagca ggcctggtgg cctcagagac tcgccctgtg ggcggagcag cctcacagcc    6900
aggttgaagt cagcactctg cccctgcccc acgcggggag cgggcaccag tcccagggca    6960
cagacgtgct gggtgattaa tctgggtgat taagcctcgg gctgagaggc tgttgagaga    7020
gaacacgctc cattgtggag ctggctcagc attccttacg ccatggtgg caggggctgt     7080 aaccacaggg acggcggaag tggtggaggg tggtggggta tggagggaag cccagagggc    7140
tctgtgcagg aaggtggagc ctggtgcaat ggagggaca gcaagggctc ctcagacctc     7200
tgcgggcccc ccactcccct ggtcacctgt tttgtctctg atctggcctg ggtcggccct    7260
cactcctggc cccacctcat agccccccct ggtgggctc cgctccagcc cttctccttc     7320
ccaggggcca gtatgctggc cccaggggtc tcttggggcg tgacctcggc ctccagagaa    7380
ccctgtccca gctctgccct tccctctggg gtctctgtag atgggacgct ggtcacagca    7440
```

```
gcctgtctga tttgttccct gtggcctagg ttcctgagcc ccacagtgcc agggatgga   7500
tgccaccgga tctttgaaag accagtgtca ggccgggcgc agtggctcac gcctgtaatc   7560
ccagcacttt gggaggccga ggtgggcgga tcacgaagtc aggagatcga gaccatcctg   7620
gctaacacgg tgaaacccccg tctccactaa aatacaaaa agttagctgg gcgtggtggt   7680
gggcgcctgt agtcccagct actcgggagg ctgaggcagg agaatggcgt gaaccgggga   7740
ggcggagctt gcagtgagcc gagatcgcgc cattgcactc cagcctgggt gacagagcga   7800
gactcggtct caaaaaaaaa agaaaaaaag gaaagaccag tgtcttggga gttgggaaac   7860
ctgggctgga gactcactgc atgaccctg agaagttgca cctcagaacc tcagtcctcg   7920
catctgcaga atgggtctgt gaacacctca gctgcccgaa cgtggatgcc gcaggctgac   7980
ccagcactga gctctaccaa gaccagggc cagccgtgtg ctccctccag gcctgtgccc   8040
agcgtggaga ggcctcgtcc cgtgggcgct gggtggagc cttcctggtg tttgtggaca   8100
tctctggaga gggccagagg caggtgggtg acacgggca tggctcaatc atgggtggtc   8160
cagactggag aggtaccctc gggctgggag cggggaggct ggccagggtg gactttcggg   8220
gcctccatgg ataccctcac catctggaat cggagagggg cacggcacaa aggagggcgg   8280
ggccagggcc aggactggag tcgggggcac ctctgtgcca acaggggcct tggatctggg   8340
gtacagcatg gttccccggc cctgaagggg ctggcgtgtg ggacaggctt cccaggaatg   8400
gataggcagg gatggatgct gcctgattgg ggcgggaggc tggaggcagg gcaggtgcag   8460
gcacctgagg gcagcactca cctccacagg ggtccagggg cctccccagc ctcagtacct   8520
ggcctgggct cctgcctcca gagagcctgg ccccaaggaa gagtctagta agcttagttc   8580
ccatcgggct tccatgaaag cacaactggc ccggcaggaa accgaattaa aaagcaatat   8640
ttgtatcagt ggaagacatt tgctgaaagg ttaaatccac atccggcagt gtgggccatg   8700
agcctccggc gtggtgttca tcaggcatgt ctctcctcct ggcctgggca cctgagcact   8760
ggggctgccc tgggcagagc tgggcaggg tgctgggggg cctggagctg cctcaccgag   8820
ggatcctcag cagccgaccc tggggaggc aaatgagact ctttctgggg accttgaggg   8880
gagctcgggg gagccatgca gagcttcacc aggcctggac actgggcatg gaggctgggc   8940
cacccaaggg ccatcaccag ggactcaggt gggtgggcct cagccctggg tgacagaagc   9000
tcacgggctg cagggcgagg ccagaggctg agccttcagg ctgaggtctt ggaggcaaat   9060
ccctccaacg cccttctgag caggcaccca gacctactgt gggcaggacc cacaggaggt   9120
ggaggccttt gggaacacc gtggagggc atagcatctc cgagagagga cagggtctgc   9180
actgggtgct gagagacagc aggggccgag cggtaggctt ccctgccccc agggatgttc   9240
caggggagcg caagggaggg gcattaatat cgtggcaaga aagggcaggc attgcagagt   9300
gagcagcgac ggaactgggt tttgtgggat gcataggagt tcacccggat aagaggtggg   9360
tgaggaatga cactgcaaac cggggatcac ggagccccaa atccttctgg gccaggaagt   9420
gggaagggtt gggggggtctt ccctttgctt tgactgagca ctcagcctgc ctgcagaggg   9480
cagcgaggag ccacggaggg gtgtgggaca gggatgccat ggctgaagca gttttaggaa   9540
aggtcccagg ggctattgtt gaagagagaa cggggagcgg ggagtcccac agctgacagg   9600
agcagagtgg gccctgagag atgccagctc tgggtgccaa agtgaccagc cggggtaggc   9660
cttcgagaag tcaggagcg tctagggctt ctggctcctg ctgggcccag ggtgtcatct   9720
tgggctgcca acaccagaaa gcccagcaga tacaggaagc cccaagccct gtcggaaacg   9780
```

-continued

| | |
|---|---|
| gttcttctcc aggagggaca gcggtggcag cgttcagccg caggccatgc actctggggc | 9840 |
| cacgtccttc cctctgtaca gtccagcatt gtcaaggcgg gctctggcca tctctgctga | 9900 |
| ccccagaggg atggggaggc ctccccttcc accagaaggg ccagaagcca ccctgggcag | 9960 |
| gggcatcact ctccctgggt ggggcagcgg cggggagcag gaggtgccag tgggcgtggg | 10020 |
| ctggatgcgg gtgcctgcgg ggcggacatg gaacttgggg gaggctctag gctggggttg | 10080 |
| tcctcaaggg agttctcagg tcaccccagg gtcaccctca acccgggggcc tggtgggta | 10140 |
| gaggagaaac tgcaaaggtc tctccaaggg gaaggcatca gggccctcag cactgaggga | 10200 |
| cgtgcgtgct cttcaaagaa ggggccacag gaccccgagg gaagccagga gctagcagtg | 10260 |
| ggccatagag gggctgagtg gggtgggtgg aagccgtccc tggccctggt cgccctggca | 10320 |
| accctggtgg ggactgtgat gcaggaggtg gcagccattt ggaaacgcgt ggcgtctcct | 10380 |
| tagagatgtc ttcttcagcc tcccagggtc ctccacactg gacaggtggg ccctcctggg | 10440 |
| acattctgga ccccacaggg cgagcttggg aagccgctgc aagggccaca cctgcagggc | 10500 |
| ccggggggctg tgggcagatg gcactcctag gaaccacgtc tacaagacac acggcctgga | 10560 |
| atcttctgga gaagcaaaca aattgcctcc tgacatctga ggctggaggc tggattcccc | 10620 |
| gtcttggggc tttctgggtc ggtctgccac gaggttctgg tgttcattaa aagtgtgccc | 10680 |
| ctgggctgcc agaaagcccc tccctgtgtg ctctcttgag ggctgtgggg ccaagggggac | 10740 |
| cctggctgtc tcagcccccc gcagagcacg agccctggt ccccgcaagc ccgcgggctg | 10800 |
| aggatgattc agacagggct ggggagtgaa ggcaattaga ttccacggac gagcccttc | 10860 |
| tcctgcgcct ccctccttcc tcacccaccc ccgcctccat caggcacagc aggcagggt | 10920 |
| ggggggatgta aggaggggaa ggtggggggac ccagagggggg ctttgacgtc agctcagctt | 10980 |
| ataagaggct gctgggccag ggctgtggag acggagcccg gatccaccgg tcgccaccat | 11040 |
| ggtgagcaag ggcgaggagc tgttcaccgg ggtggtgccc atcctggtcg agctggacgg | 11100 |
| cgacgtaaac ggccacaagt tcagcgtgtc cggcgagggc gagggcgatg ccacctacgg | 11160 |
| caagctgacc ctgaagttca tctgcaccac cggcaagctg cccgtgccct ggcccaccct | 11220 |
| cgtgaccacc ctgacctacg gcgtgcagtg cttcagccgc tacccgacc acatgaagca | 11280 |
| gcacgacttc ttcaagtccg ccatgcccga aggctacgtc caggagcgca ccatcttctt | 11340 |
| caaggacgac ggcaactaca agacccgcgc cgaggtgaag ttcgagggcg acaccctggt | 11400 |
| gaaccgcatc gagctgaagg gcatcgactt caaggaggac ggcaacatcc tggggcacaa | 11460 |
| gctggagtac aactacaaca gccacaacgt ctatatcatg gccgacaagc agaagaacgg | 11520 |
| catcaaggtg aacttcaaga tccgccacaa catcgaggac ggcagcgtgc agctcgccga | 11580 |
| ccactaccag cagaacaccc ccatcggcga cggccccgtg ctgctgcccg acaaccacta | 11640 |
| cctgagcacc cagtccgccc tgagcaaaga ccccaacgag aagcgcgatc acatggtcct | 11700 |
| gctggagttc gtgaccgccg ccgggatcac tctcggcatg gacgagctgt acaagtaaag | 11760 |
| cggccggccg cgactctagc tagatcataa tcagccatac cacatttgta gaggttttac | 11820 |
| ttgctttaaa aaacctccca cacctccccc tgaacctgaa acataaaatg aatgcaattg | 11880 |
| ttgttgttaa cttgtttatt gcagcttata atggttacaa ataaagcaat agcatcacaa | 11940 |
| atttcacaaa taaagcattt ttttcactgc attctagttg tggtttgtcc aaactcatca | 12000 |
| atgtatc | 12007 |

HUMAN TYROSINE HYDROXYLASE PROMOTER AND USES THEREOF

RELATED APPLICATIONS

This is a continuation-in-part application of the U.S. patent application, Ser. No. 09/942,325, filed Aug. 29, 2001, now abandoned, which claims priority to Provisional Application No. 60/228,931, filed Aug. 30, 2000.

GOVERNMENT RIGHTS IN THE INVENTION

This invention was made with government support under grants NS24204 and NS32519 awarded by the NIH. The government has certain rights to the invention.

BACKGROUND OF THE INVENTION

1. Field of the Invention

The present invention is related to a human tyrosine hydroxylase (TH) promoter and uses thereof.

2. Background of the Invention

A number treatment methods are currently under investigation where healthy cells performing a specialized function are transferred, either directly or after genetic modification, to an individual to treat a disease condition. Such diseases include neurological diseases, leukemia, and immune and genetic disorders. Specifically, cell based therapies have been described or suggested for type I insulin dependent diabetes (Bonner-Weir et al. J Pathol 2002; August 197(4):519–26); adenosine deaminase (ADA)-deficient severe combined immunodeficiency (SCID) (Aiuti et al. Science 2002; Jun. 28, 296(5577):2410–3); Parkinson's disease (Arenas, Brain Res Bull. 2002 April; 57(6):795–808); and mucopolysaccharidoses, a group of lysosomal storage diseases (Vogler et al., Pediatr Dev Pathol 2001 September–October; 4(5):421–33). Cell replacement therapy has also been contemplated for treatment of other diseases such as stroke, head and spinal cord trauma, Alzheimer's Disease, multiple sclerosis, amyotrophic lateral sclerosis (ALS), genetic enzyme deficiencies in general, and muscular dystrophy (see, e.g. Holden, Science, 297:500–502, 2002).

However, the source of such replacement cells and purification procedures to enrich such cells from the sources are not always optimal.

For example, in Parkinson's disease, the degeneration of the TH+ dopaminergic cells of the substantia nigra parallels the symptoms. Cell replacement or transplantation has been hindered by the limited supply of cells as up to 6–8 fetal brains are harvested for treatment of a single patient. Furthermore, the TH+ dopaminergic cells represent only 0.5–1% of the fetal mesencephalon. This may well underlie the variability and low success rate of this treatment. Therefore, for the purposes of cell-transplantation treatments, it would be desirable to develop methods to easily identify, isolate and enrich the population of TH+ dopaminergic cells.

Similar to neurons, the endocrine cells of the mammalian pancreas have been considered to be post-mitotic, i.e., terminal, essentially non-dividing cells. Recent work has shown that the cells of the mammalian pancreas are capable of survival in culture, however, propagation of differentiated cells having endocrine function has met with, at best, limited success. In addition, pancreatic ductal cells have been differentiated into islet cells (Ramiya et al., 2000) and also human embryonic stem cells have been shown to be capable of differentiating into pancreatic islet cells (Lumensky et al. 2001).

However, problems in isolation of the proper insulin-producing population from the cell cultures limits their use in treatment of pancreatic disorders. Such disorders include diabetes mellitus, a disease that impairs or destroys the ability of the beta cells of the islets of Langerhans (structures within the pancreas) to produce sufficient quantities of the hormone insulin, a hormone that serves to prevent accumulation of sugar in the bloodstream. Type I diabetes mellitus (insulin dependent, or juvenile-onset diabetes) typically requires full hormone replacement therapy. In type II diabetes, sometimes referred to as late onset, or senile diabetes, treatment often does not require insulin injections because a patient suffering with Type II diabetes may be able to control his/her blood sugar levels by carefully controlling food intake. However, as many as 30% of these patients also have reduced beta cell function and, therefore, are candidates for hormone replacement therapy as well.

Current treatment of individuals with clinical manifestation of diabetes attempts to emulate the role of the pancreatic beta cells in a non-diabetic individual. Individuals with normal beta cell function have tight regulation of the amount of insulin secreted into their bloodstream. This regulation is due to a feed-back mechanism that resides in the beta cells that ordinarily prevents surges of blood sugar outside of the normal limits. Unless blood sugar is controlled properly, dangerous, even fatal, blood sugar levels can result. Hence, treatment of a diabetic individual nowadays involves the use of recombinantly produced human insulin on a daily basis.

Injected insulin and diet regulation permit survival and in many cases a good quality of life for years after onset of the disease. However, there is often a gradual decline in the health of diabetics that has been attributed to damage to the vascular system due to the inevitable surges (both high and low) in the concentration of glucose in the blood of diabetic patients. In short, diabetics treated with injected insulin cannot adjust their intake of carbohydrates and injection of insulin with sufficient precision of quantity and timing to prevent temporary surges of glucose outside of normal limits. These surges are believed to result in various vascular disorders that impair normal sight, kidney, and even ambulatory functions.

Both of these disease states, i.e., type I and type II diabetes, involving millions of people in the United States alone, preferably should be treated in a more regulated fashion. Successful transplants of whole isolated islets, for example, have been made in animals and in humans. However, long term resolution of diabetic symptoms has not yet been achieved by this method because of a lack of persistent functioning of the grafted islets in situ (see Robertson (1992) *New England J. Med.,* 327:1861–1863).

For the grafts accomplished thus far in humans, one or two donated pancreases per patient treated are required. Unfortunately only some 6000 donated human pancreases become available in the United States in a year, and many of these are needed for whole pancreas organ transplants. Therefore, of the millions of diabetic individuals who could benefit from such grafts, only a few of them may be treated given the current state of technology. If the supply of insulin producing islet cells could be increased by culturing and/or differentiating pluripotent stem cells they would provide much needed material to allow development of new cell replacement treatment options for diabetes. Therefore, it would be useful to develop a method of culturing cells that could be differentiated into pancreatic islet cells and a method that would allow easy selection of insulin-producing cells from the cultures for the purposes of administering such cells to individuals in need thereof.

The enzyme tyrosine hydroxylase (EC 1.14.16.2, TH) is encoded by a single copy gene on human chromosome 11p15[8; 51] and it catalyzes the rate limiting step in the synthesis of catecholamine neurotransmitters in the central and peripheral nervous systems: the hydroxylation of tyrosine to yield dopa.[45] For example, islet cells have been shown to contain TH enzymes involved in the synthesis of catecholamines (Teitelman, et al., *Development* 1993, 118: 1031–1039; Iturriza, et al., *Neuroendocrinology* 1993, 57: 476–480). Thus far, regulation of TH expression has been studied mainly because of its role in biosynthesis of catecholamines in neurophysiology and the alterations associated with a variety of psychiatric illnesses. Classically, drugs effective for treatment of psychotic symptoms have been antagonists of dopamine receptors, and a number of studies have assessed the linkage between mutations in the TH gene and disorders such as schizophrenia and bipolar disorder. However, there is no evidence as of yet for a role in these, or other diseases of mutations in the TH protein coding regions. However, polymorphisms elsewhere in the TH sequence, and in TH-regulating transcription factors have been described.[38, 5]

In light of the above, it would therefore be advantageous to discover the functional domains regulating human TH-gene expression, particularly regulatory regions directing human TH expression to both central and peripheral neurons.

SUMMARY OF THE INVENTION

We have now isolated, purified and characterized a human tyrosine hydroxylase (hTH) promoter nucleic acid sequence. We have further discovered a method of selecting TH positive (TH+) cells by preparing a construct comprising a hTH promoter operably linked to a heterologous nucleic acid sequence, for example, green fluorescent protein encoding sequence, and transfecting cells, particularly stem cells, with the construct. We have also discovered that a hTH promoter is useful in gene therapeutic applications in driving therapeutic genes or other nucleic acid sequences operably linked to the hTH promoter. We also provide cell lines and transgenic animals expressing a transgene comprising the hTH promoter operably linked to a heterologous sequence, which cell lines and transgenic animals are useful for isolating TH+ cells for transplantation or for screening of therapeutic agents that affect TH+ function. Methods of producing cell lines and transgenic animals are also provided.

In one embodiment, the invention provides a human tyrosine hydroxylase (hTH) promoter sequence (SEQ ID NO: 1) or a functional fragment thereof.

In another embodiment, the invention provides a construct comprising an hTH promoter nucleic acid sequence operably linked to a heterologous nucleic acid sequence. In one embodiment, the heterologous sequence encodes a reporter molecule, e.g., a fluorescent protein, an antigen, or a molecule conferring an antibiotic resistance.

In another embodiment, the heterologous nucleic acid sequence encodes a therapeutic protein. The heterologous nucleic acid sequence can alternatively be operably linked with a nucleic acid encoding reporter molecule or another therapeutic protein. In the preferred embodiment, the therapeutic protein is a glial cell derived neurotrophic factor, a superoxide dismutase, a member of the fibroblast growth factor family or brain derived neurotrophic factor (BDNF).

The invention also provides a method of isolating TH positive cells comprising providing a construct comprising a hTH promoter nucleic acid sequence or a functional fragment thereof operably linked to a heterologous nucleic acid sequence encoding a reporter molecule and transfecting a plurality of cells with the construct. The transfected cells are thereafter subjected to a selection procedure wherein the TH positive cells are selected based upon their expression of a reporter molecule.

In an alternative embodiment, the invention provides a method of isolating TH positive cells comprising providing a construct comprising an hTH promoter nucleic acid sequence or a functional fragment thereof operably linked to a nucleic acid encoding a reporter molecule and transfecting a plurality of cells with the construct, differentiating the transfected cells in culture, and selecting the differentiated cells that express the reporter molecule.

The invention also provides a method of treating an individual in need thereof by administering to such individual cells obtained using either of the above described isolation methods.

In one embodiment, the individual is affected by a neurological disorder, such as Parkinson's disease. In another embodiment, the individual is affected with diabetes, preferably type I diabetes.

The invention further provides a method of treating a subject comprising delivering to an individual a construct comprising an hTH promoter nucleic acid sequence or a functional fragment thereof operably linked to a heterologous nucleic acid sequence. Preferably, the heterologous nucleic acid comprises a sequence which encodes a therapeutic protein.

In yet another embodiment, the invention provides a cell line containing a hTH promoter nucleic acid sequence or a functional fragment thereof operably linked to a nucleic acid sequence encoding reporter.

In a further embodiment the invention provides an assay for screening for agents that affect the function of a hTH promoter or a functional fragment thereof comprising providing a cell line containing a hTH promoter nucleic acid sequence or a functional fragment thereof operably linked to a nucleic acid encoding a reporter molecule, contacting said cell line with a candidate agent and detecting expression of the reporter molecule, wherein increase in the amount of expression of the reporter molecule is indicative of an agent capable of increasing the activity of hTH promoter or a functional fragment thereof and decrease in the amount of expression of the reporter molecule is indicative of an agent capable of decreasing the activity of hTH promoter or a functional fragment thereof. The cell line may be in vivo or ex vivo. The method is useful in screening for agents for the treatment of diseases, such as Parkinson's disease or diabetes.

The present invention also provides transgenic animals and a method of producing transgenic animals that contain within their genome a heterologous nucleic acid sequence under the control of the human tyrosine hydroxylase promoter. Preferably, the animal is a mouse. A preferred heterologous nucleic acid sequence encodes a reporter molecule, e.g., the green fluorescent protein.

BRIEF DESCRIPTION OF THE FIGURES

FIGS. 3A–3G show an overview of the TH promoter structure. FIG. 3A marks the nucleotide positions with respect to the start of transcription (Exon I in FIG. 3B, scale in kilobases). FIG. 3B shows the 5' end of the human TH gene is represented, including 11 kb of promoter and the first Exons. BBE's I–IV are recognition sites for the transcription factor bicoid, associated with regulation of the TH gene by Pitx3 (Lebel et al., 2001). FIG. 3C shows the repeat sequences within the human TH promoter including a previously described tetranucleotide (TTCA) repeat in the first intron (Albanese et al., 2001; Meloni et al., 1998). FIG. 3D shows the locations of select response elements. These include the early response factors EGR and AP-1-4; a single cyclic-AMP response element (CRE); a Gli site which may mediate Sonic hedgehog (Shh) action; and two 70% matches to the neuron restrictive silencer element, NRSE (Schoenherr et al., 1996) FIG. 3E shows the human TH promoter. Solid black squares denote Conserved Regions I–V. FIG. 3F shows the mouse TH promoter (GENBANK ACCESSION locus: AP003184; gi[16303287]). Solid black squares denote Conserved Regions I–V. FIG. 3G show the rat TH promoter (GENBANK ACCESSION locus: AF069036; [gi: 5724776]). Solid black squares denote Conserved Regions III–V.

FIGS. 7A and 7C are samples from non-transgenic animals. The sharp cutoff in cell numbers at a fluorescence intensity 1 log above base line can be seen. FIGS. 7B and 7D show samples from ratTH-EGFP and hTH-EGFP transgenics, respectively. Both Figs. show a population of cells with fluorescence intensity above the maximums of FIGS. 7A and 7C (non-transgenic). In FIG. 7B the population extends to 2.5 logs above baseline or 1.5 logs (32×) the intensity of the "background" cells. This represents the maximum signal/noise ratio attainable in discriminating EGFP+ from EGFP– cells in this transgenic model. In contrast, the hTH-EGFP transgene of the present invention yields a signal intensity of about 3.5 logs above baseline (FIG. 7D) and 2.5 above background for a signal/noise ratio of 316×.

FIG. 8A marks the nucleotide positions with respect to the start of transcription (Exon I in B). FIG. 8B shows the 5' end of the human TH gene is represented, including 11 kb of promoter and the first Exons. BBE's I–IV are recognition sites for the transcription factor bicoid, associated with regulation of the TH gene by Pitx3. FIG. 8C shows the repeat sequences within the human TH promoter including a previously described tetranucleotide (TTCA) repeat in the first intron. FIG. 8D shows the locations of select potential response elements. These include the early response factors EGR and AP-1-4; a single cyclic-AMP response element (CRE), a Gli site which may mediate Shh action, and two 70% matches to the neuron restrictive silencer element, NRSE. FIG. 8E shows a Human TH promoter. Solid black squares denote Conserved Regions I–V. FIG. 8F is a 12,007 bp transgene used to generate hTH-11 kb-EGFP transgenic mice. FIG. 8G shows a "minipromoter" and reporter construct. The 12,007 construct has been cleaved at a unique internal restriction site, and a synthetic gene sequence (*) inserted. The bars in this region reflect the numerous sequence elements from B,D, and E above assembled in a 500–1000 bp synthetic sequence. These include EGR, AP-1-4, BBE's I through III, the 5' NRSE, and conserved regions I–IV. To encompasses all the potential response elements illustrated in B through E (above) requires less than 300 bp of total sequence. To be conservative, and to allow for space between elements so that transcription factors are not subject to steric hinderance, we allot up to 1 kb for this synthetic region. This is quite manageable for chemical/enzymatic gene synthesis. The rest of the hTH promoter is in white, the crosshatch represents the reporter (GFP), while the SV40 polyadenylation sequence is in black. FIG. 8H is a diagram of a typical $3^{rd}$ generation lentivirus vector (Ailles,L. E. and Naldini,L., HIV-1-Derived Lentiviral Vectors. In: Trono,D. (Ed.), Lentiviral Vectors, Springer-Verlag, Berlin, Heidelberg, N.Y., 2002, pp. 31–52) drawn roughly to scale. The "cargo" includes a generic promoter ("prom") and reporter ("TRANSGENE"). FIG. 8I shows a design of a lentiviral vector incorporating an hTH minipromoter driving expression of GFP. The entire vector/transgene construct is about 11–12 kb, well within range of the 8–14 kb packaging capacity of the virus.

FIGS. 9A–9C show human tyrosine hydroxylase promoter Bicoid Binding Elements (BBE's). FIG. 9A shows that BBE I–IV sequences all match 9 bp consensus BBTAATCYV (B=C, G, or T; Y=C or T; V=A, C, or G). The orientation of BBE II has been reversed "(−)" in this table to emphasize alignment with other sites. Numbers indicate positions of sites within 13,329 bp gene sequence, or, in parentheses, with respect to transcript start. FIG. 9B shows an EMSA employing 25 bp $^{32}$P-labeled double stranded oligonucleotide corresponding to BBE II (see Methods). Additions, Lane 1: Nuclear protein extract from COS-7 cells transiently transfected with GFP-expressing plasmid. Lane 2: Nuclear protein extract from COS-7 cells transiently transfected with plasmid expressing murine gooscoid-like (gscl) homeodomain protein. Arrowhead (<) indicates bicoid/gscl-specific complex. Lanes 3 and 4: As in 2, but with competition by 25 (lane 3) and 12.5-fold (lane 4) molar excess of unlabeled BBE II oligonucleotide. Lane 5: As in 2 but with competition by 50-fold molar excess of AP-1 oligonucleotide. FIG. 9C shows a supershift assay, performed as in B. lane 2 with the following additions: Lane 1:3 µl of rabbit preimmune serum; Lanes 2,3 and 4:1, 2, and 3 µl of affinity purified anti-gscl rabbit antiserum. Arrowhead (>) indicates bicoid/gscl-specific complex, while the supershifted band is indicated by an asterisk (*).

FIGS. 11A–11K shows SEQ ID NO: 1 and SEQ ID NO: 38.

DETAILED DESCRIPTION OF THE INVENTION

Figure 1:
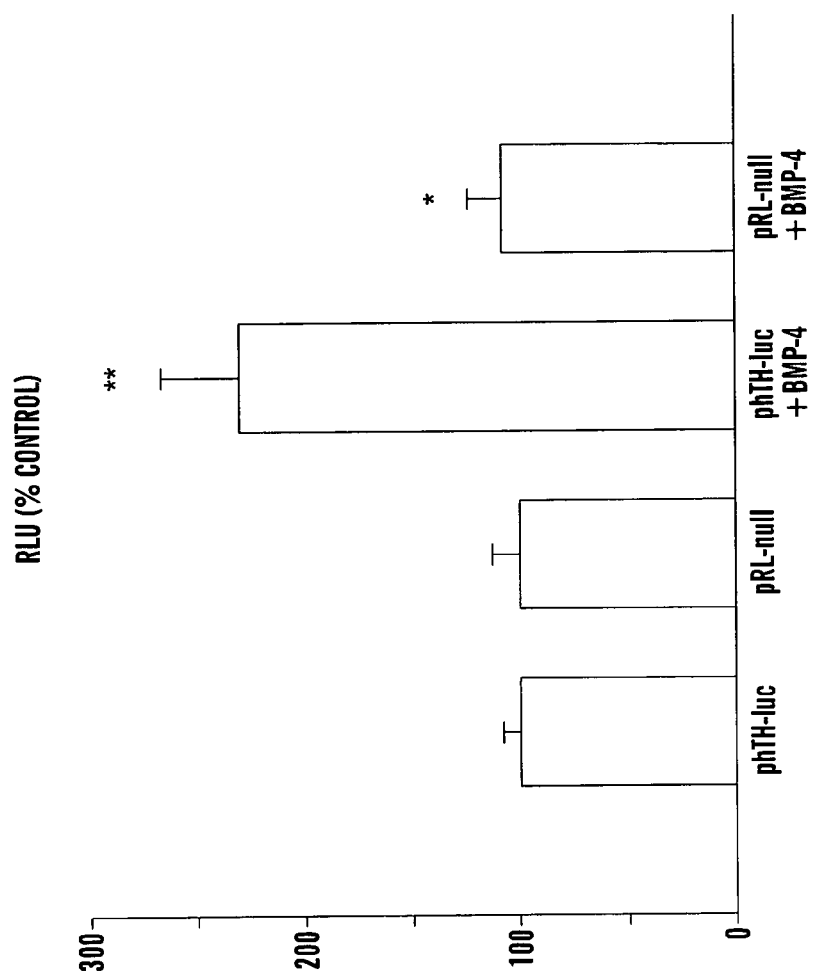
FIG. 1 shows reults from the Dual-Luciferase Reporter Assay System using the hTH promoter driving a luciferase reporter gene. In 18 wells of a 24-well plate, SH-SY5Y human neuroblasotoma cells (ATCC cat. # CRL-2266) are transfected with a calcium coprecipitate of pRL-null (a promoter/enhancer minus control; Promega, Madison, Wis.) and pMAK 1150-5 (see, FIG. 2). Groups 1 and 3 are transfected with the reporter construct (luciferase, pMAK 1150-5). Groups 2 and 4 are transfected with the control construct (renilla, pRL-null). One day following transfection, the culture media is changed to DM for all groups and Bone Morphogenetic Protein-4 (250 ng/ml; R & D Systems) is added to the media of groups 3 and 4, and is ommitted from the media of groups 1 and 2. BMP-4 has previously been shown to specifically augment TH expression in the PNS (Howard et al., 2000; Ernsberger, 2000; Reissmann et al., 1996) and CNS (Stull et al., 2001c). Assays for luciferase and renilla luciferase (control) are performed 24 hours following the BMP-4 addition. The Dual-Luciferase Reporter Assay System (Promega, Part #TM040) is used to assay independently firefly luciferase (groups 1 and 3) and Renilla luciferase (groups 2 and 4) according to the manufacturer's instructions. The control reporter, pRL-null, does not significantly change with BMP-4 treatment (compare Group 2 to Group 4, $p>0.5$). In contrast, the hTH reporter construct has a significant increase in the relative light fluorescence (RLF) when treated with BMP-4 (compare Group 1 to Group 3, $p<0.001$; $n=9$). Thus, the transfected hTH promoter mimics the response to BMP-4 of cultured embryonic striatal neurons ex vivo (Stull et al., 2001b)

We provide an isolated, purified and characterized human tyrosine hydroxylase (hTH) promoter nucleic acid sequence. We have further discovered a method of selecting TH positive (TH+) cells by preparing a construct comprising a hTH promoter operably linked to a heterologous nucleic acid sequence, for example, green fluorescent protein encoding sequence, and transfecting cells, particularly stem cells, with the construct. We have also discovered that a hTH promoter is useful in gene therapeutic applications in driving therapeutic genes or other nucleic acid sequences operably linked to the hTH promoter. We also provide cell lines and transgenic animals expressing a transgene comprising the hTH promoter operably linked to a heterologous sequence, which cell lines and transgenic animals are useful for isolating TH+ cells for transplantation or for screening of therapeutic agents that affect TH+ function. Methods of producing cell lines and transgenic animals are also provided.

Both neuronal cells and islet cells have been shown to contain enzymes involved both in the synthesis of CAs—tyrosine hydroxylase (TH) [9,10] and dihydroxyphenylalanine (DOPA) decarboxylase [11,12]

In one embodiment, the invention provides a human tyrosine hydroxylase (hTH) promoter sequence or a functional fragment thereof. The term "human tyrosine hydroxylase promoter sequence" or "hTH promoter" refers to SEQ ID NO: 1 shown in the Sequence Listing as well as the functional equivalents thereof. The human TH promoter functions, that is referred to herein is to direct high-level cell-specific expression of a reporter to cells of clinical importance, such as cells expressing insulin or dopamine. The term "functional fragment" refers to a region or a combination of regions necessary for efficient, and specific expression by the hTH promoter as described in the Example below. Preferably, a functional fragment is a Conserved Region as described herein and more particularly in the Example and Figures.

FIG. 3A marks the nucleotide positions with respect to the start of transcription (Exon I in B). FIG. 3B shows the 5' end of the human TH gene is represented, including 11 kb of promoter and the first Exons. BBE's I–IV are recognition sites for the transcription factor bicoid, associated with regulation of the TH gene by Pitx3 [32]. FIG. 3C shows the repeat sequences within the human TH promoter including a previously described [1; 42] tetranucleotide (TTCA) repeat in the first intron. FIG. 3D demonstrates the location of select potential response elements are shown. These include the early response factors EGR and AP-1-4; a single cyclic-AMP response element (CRE), a Gli site which may mediate Shh action, and two 70% matches to the neuron restrictive silencer element, NRSE [65] FIG. 3E shows the human TH promoter. Solid black squares denote Conserved Regions I–V. FIG. 3F shows the mouse TH promoter (GENBANK ACCESSION locus: AP003184; gi[16303287]). Solid black squares denote Conserved Regions I–V. FIG. 3G shows the Rat TH promoter (GENBANK ACCESSION locus: AF069036; [gi:5724776]). Solid black squares denote Conserved Regions III–V.

The identification of the hTH promoter of the present invention also allows the use of a reasonably sized promoter sequence in driving expression of desired nucleic acids. For example, using the zinc finger protein RU49 gene, high level cell-specific expression has been achieved in transgenic mice using a 131 kb construct derived from a BAC (bacterial artificial chromosome) (Yang,et al. Nature Biotechnology, 15 (1997) 859–865). However, there is no efficient method for introducing constructs of that size into therapeutically useful cells for an allograft. In xenografts, the 12,007 transgene may be used as is. For example, transgenic pigs are generated using the hTH-11 kb-EGFP transgene. GFP+/TH+ neurons are recovered by FACS and used for xenotransplantation. The pigs may be previously genetically modified to reduce immunological rejection. The unique findings with the hTH-11 kb-EGFP transgenic mice in defining a functional fragment of the hTH promoter which is of a size which can be introduced into cells using traditional methods described in detail below.

In another embodiment, the invention provides a construct comprising an hTH nucleic acid sequence or a functional fragment thereof operably linked to a heterologous nucleic acid sequence.

The heterologous nucleic acid sequence can be any nucleic acid sequence including a fusions sequence comprising two or more isolated and substantially purified naturally occurring or synthetic nucleic acid sequences.

In one embodiment, the heterologous sequence encodes a reporter molecule. The term "reporter molecule" as used herein includes a protein or a fragment thereof that can be used to monitor or select cells expressing the reporter molecule. Reporter molecules useful according to the present invention include but are not limited to fluorescent proteins, antigens, receptors for specific ligands and antibiotic resistance encoding nucleic acid sequences. Examples of specific reporter sequences include, but are not limited to, beta-galactosidase, beta-lactamase, alkaline phosphatase, fluorescent proteins, CAT, and luciferase.

Examples of fluorescent proteins include blue, cyan, green, yellow, red and far-red fluorescent proteins or enhanced forms thereof which are readily available (see, e.g., Clontech, Palo Alto, Calif.). A fluorescent protein as a reporter is preferred, because it will allow a simple visual detection of the transgene under a fluorescent microscope or using fluorescence activated cell sorting (FACS). For example, detection of a transgenic mouse can be performed using a simple tail sample and observing it under a fluorescent microscope instead of more time consuming isolation of DNA and consequent PCR to detect the transgene. Also, in an assay for screening for agents affecting the TH promoter activity, changes in the expression of a fluorescent protein, that can be easily observed under a fluorescence microscope or using FACS, will circumvent the more time consuming immunohistochemical analysis which requires more time consuming sample preparation including fixing and immunohistochemical staining of the cells with specific antibodies.

Fluorescence microscopy is a well known technique to one skilled in the art. Microscopes such as, for example, Leitz Leica DRMB microscope, Olympus BX51 Upright Microscope, or Olympus IX70 Inverted Microscope, can be used to analyze cells or transgenic animals of the present invention, when the hTH promoter construct is operably linked with a heterologous nucleic acid comprising a sequence encoding a fluorescent protein.

Fluorescence activated cell sorting (FACS) is also a technique that is well known to one skilled in the art. In FACS, the cells in suspension are separated based upon properties measured in the fluid flow (see, e.g., Current Protocols in Flow Cytometry, Edited by: J. Paul Robinson, Zbigniew Darzynkiewicz, Phillip Dean, Alan Hibbs, Alberto Orfao, Peter Rabinovitch, Leon Wheeless, John Wiley&Sons, Inc., in affiliation with International Society of Analytical cytology, (last updated July 2002; Flow Cytometry and Cell Sorting by A. Radbruch, Ed., Springer Verlag; ISBN: 3540656308; 2nd spiral edition, January 2000; and Guide to Flow Cytometry Methods by W. McLean Grogan and James M. Collins, Marcel Dekker; ISBN: 0824783301, Jul. 27, 1990).

The term "antibiotic resistance encoding nucleic acid sequence" means a nucleic acid sequence encoding an activity that confers resistance to an antibiotic, a substance produced either synthetically or by a microorganism that, either naturally or with limited chemical modification, will inhibit the growth of or kill an eukaryotic cell. Such antibiotic resistance encoding nucleic acid sequences are known to one skilled in the art (see, e.g. Kriegler M., Gene Transfer and Expression, a Laboratory Manual, Stockton Press, New York, 1990). For example, a neomycin resistance-encoding gene can be used to confer G418 resistance in eukaryotic host cells.

Human TH promoter nucleic acid can also be operably linked to a cell surface receptor or antigen that can be recognized by a specific ligand or antibody and such construct is useful in isolating the cells using the ligand. Such receptor-ligand, or antigen-antibody combinations include high affinity hexapeptide ligands that are known for the anti-dynorphin mAb 32.39, (see Barrett et al, *Neuropeptides* 6:113–120 (1985) and Cull et al., *Proc. Nat'l. Acad. Sci. USA* 89:1865–1869 (1992)) and a variety of short peptides which are known to bind the MAb 3E7 (Schatz, *Biotechnology* 11:1138–43 (1993)). Another combination of tag and antibody is described by Blanar & Rutter, *Science* 256:1014–1018 (1992). Another example of a ligand-receptor pair is the FLAG[R] system (Kodak). The FLAG[R] molecular tag consists of an eight amino acid FLAG peptide marker that is linked to the target binding moiety. A 24 base pair segment containing a FLAG coding sequence can be inserted adjacent to a nucleotide sequence that codes for a polypeptide. The FLAG peptide includes an enterokinase recognition site that corresponds to the carboxyl-terminal five amino acids. Capture moieties suitable for use with the FLAG peptide marker include antibodies Anti-FLAG M1, M2 and M5, which are commercially available.

The term "operably linked" means that a gene and a regulatory sequence(s) are connected in such a way as to permit gene expression when the appropriate molecules (e.g., transcriptional activator proteins) are bound to the regulatory sequence(s).

In another embodiment, the invention provides a construct comprising an hTH promoter nucleic acid sequence operably linked to a heterologous nucleic acid sequence which comprises a nucleic acid sequence encoding a therapeutic molecule. Examples of therapeutic molecules useful according to the present invention include, but are not limited to glial cell derived neurotrophic factor (GDNF), superoxide dismutase (Barkats et al., J. Neurochem., 82:101–109, 2002), a member of a fibroblast growth factor (FGF) family and brain derived neurotrophic factor (BDNF).

The construct comprising the hTH promoter nucleic acid operably linked to a heterologous nucleic acid is introduced into the target cell by any method which will result in the uptake and expression of the nucleic acid by the target cells. The introduction can be by standard techniques, e.g. infection, transfection, transduction or transformation. Examples of modes of gene transfer to cells include e.g., naked DNA, $CaPO_4$ precipitation, DEAE dextran, electroporation, lipofection, cell microinjection, adjuvant-assisted DNA, gene gun, catheters, and viral vectors.

Vectors useful according to the present invention include chemical conjugates such as described in WO 93/04701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic. The particular vector chosen will depend upon the target cell and the condition being treated.

Preferred vectors for therapeutic applications of the present invention such as transferring a construct comprising a hTH promoter operably linked to a heterologous nucleic acid sequence encoding a therapeutic protein, include viral vectors, fusion proteins and chemical conjugates. DNA vectors include pox vectors such as orthopox or avipox vectors, herpesvirus vectors such as a herpes simplex I virus (HSV) vector (Geller, A. I. et al., *J. Neurochem*, 64: 487 (1995); Lim, F., et al., in DNA Cloning: *Mammalian Systems*, D. Glover, Ed. (Oxford Univ. Press, Oxford England) (1995); Geller, A. I. et al., *Proc Natl. Acad. Sci.: U.S.A.:*90 7603 (1993); Geller, A. I., et al., *Proc Natl. Acad. Sci USA:* 87:1149 (1990)), Adenovirus Vectors (LeGal LaSalle et al., *Science*, 259:988 (1993); Davidson, et al., *Nat. Genet* 3: 219 (1993); Yang, et al., *J. Virol.* 69: 2004 (1995), Adeno-associated Virus Vectors (Kaplitt, M. G., et al., *Nat. Genet.* 8:148 (1994)) and gutless adenovirus vectors (Ferry N. et al. Hum Gene Ther 1998 Sep. 20; 9(14):1975–81). Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors.

Retroviral vectors are preferred and include moloney murine leukemia viruses and lentiviral vectors. In a preferred embodiment, a third generation SIN lentivirus is used. Commercial suppliers of third generation SIN (self-inactivating) lentiviruses include Invitrogen (ViraPower Lentiviral Expression System). Detailed methods for construction, transfection, harvesting, and use of lentiviral vectors are given, for example, in the Invitrogen technical manual "ViraPower Lentiviral Expression System version B 050102 25-0501". Lentiviral vectors, derived from HIV, have emerged as an efficient method for gene transfer. Improvements in biosafety characteristics have made these vectors suitable for use at biosafety level 2 (BL2). A number of safety features are incorporated into third generation SIN (self-inactivating) vectors. Deletion of the viral 3' LTR U3 region results in a provirus that is unable to transcribe a full length viral RNA. In addition, a number of essential genes are provided in trans, yielding a viral stock that is capable of but a single round of infection and integration. The great deal of interest in these vectors as potential clinical tools derives from several considerations: 1) pseudotyping of the vector using amphotropic envelope proteins allows them to infect virtually any cell type; 2) gene delivery to quiescent, post mitotic, differentiated cells, including neurons, has been demonstrated; 3) their low cellular toxicity is unique among transgene delivery systems; 4) viral integration into the genome permits long term transgene expression; 5) their packaging capacity (6–14 kb)is much larger than other retroviral, or adeno-associated viral vectors. In a recent dramatic demonstration of the capabilities of this system, lentiviral vectors expressing GFP were used to infect murine stem cellsresulting in live progeny, germline transmission, and promoter-, and tissue-specific expression of the reporter (Ailles, L. E. and Naldini, L., HIV-1-Derived Lentiviral Vectors. In: Trono, D. (Ed.), Lentiviral Vectors, Springer-Verlag, Berlin, Heidelberg, New York, 2002, pp. 31–52). An example of the current generation vectors is outlined in FIG. 2 of a review by Lois et al. (Lois, C., Hong, E. J., Pease, S., Brown, E. J., and Baltimore, D., Germline transmission and tissue-specific expression of transgenes delivered by lentiviral vectors, Science, 295 (2002) 868–872. According to present invention, the human TH promoter is used to direct expression of a reporter gene to TH+ cells of clinical importance, such as islet cells or dopamine producing cells.

The vector can be employed to target essentially any desired target cell, such as a neuronal cells. For example, stereotaxic injection can be used to direct the vectors (e.g. lentivirus) to a desired location. Additionally, the construct can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the construct to the target cell (Bobo et al., *Proc. Natl. Acad. Sci. USA* 91:2076–2080 (1994); Morrison et al., *Am. J. Physiol.* 266: 292–305 (1994)). Other methods that can be used include catheters, intravenous, parenteral, intraperitoneal and subcutaneous injection, and oral or other known routes of administration.

The invention also provides a method of selecting TH positive cells comprising providing a construct comprising an hTH promoter nucleic acid sequence or a functional fragment thereof operably linked to a heterologous nucleic acid encoding a reporter molecule and transfecting a plurality of cells with the construct. The transfected cells are thereafter subjected to a selection procedure and the TH positive cells are selected.

Selection procedures are chosen according to the type of the reporter molecule encoding nucleic acid sequence attached to the hTH promoter. For example, a fluorescence activated cell sorting (FACS) can be used when the hTH promoter nucleic acid is operably linked to a nucleic acid encoding a fluorescent reporter molecule (see, Example below).

The term "cell" or "cells" includes eukaryotic cells, preferably stem cells, most preferably embryonic stem cells, such as mouse and human stem cells. The preferred stem cells include stem cells capable of differentiating into neural cells such as mesenchymal stem cells (Kopen et al., 1999; Sanches-Ramos et al., 2000; Woodbury et al., 2000), mesenchymal and/or hematopoietic stem cells (Eglitis et al., 1997; Mezey et al., 2000; Brazelton et al., 2000), neural stem cells (Reynolds et al, 1996; Doetsch et al., 1999, Johansson et al., 1999).

The cells useful according to the present invention are preferably stem cells that are capable to differentiating into cells of interest such as pancreatic islet cells or dopamine producing neuronal cells.

Preferably the stem cells are embryonal stem cells. Examples of embryonal stem cells useful according to the present invention are described in Brustle et al., Science, 1999, Bain et al., Dev. Biol., 1995; Strubing et al., Mech. Dev., 1995; Li et al., Curr. Biol., 1998; Lee et al., Nat. Biotechnol., 2000; Kawasaki et al., Neuron, 2000; Slager et al, 1993; Gottlieb et al., Cells, Tissues, Organs, 1999; Fraichard et al., *J. Cell. Sci.,* 1995; O'Shea, Anat. Rec., 1999; Liu et al., PNAS, USA 1999; Weiss et al., *J. Neurosci.,* 1996. Sources and protocols of isolating, culturing stem cells are readily available to one skilled in the art. Stem cells, particularly human and mouse stem cells useful according to the present invention, can be found, e.g., in Appendix D, in Stem Cells: Scientific Progress and Future Research Directions. Department of Health and Human Services. June 2001.

Embryonic cells can also be isolated using published methods. For example, human embryonic stem cells are isolated from a cleavage stage embryo obtained, e.g., from a laboratory performing in vitro fertilization treatment for infertility. Cells are allowed to develop into a blastocyst stage and the inner mass of a blastocyst is cultured in a multi-step process (Thompson and Odorico, Biotechnol. 18, 53–57, 2000). The pluripotent cells of the inner mass are separated from the surrounding trophectoderm by immunosurgery, an antibody-mediated dissolution of the trophectoderm. The inner cell masses are plated in culture dished containing growth medium, supplemented, e.g., with fetal bovine serum or feeder layers of of mouse embryonic fibroblasts that are gamma-irradiated to prevent replication. After about 9–15 days, when the inner cell masses have divided and formed clumps of cells, cells from the periphery of the clumps are chemically or mechanically dissociated and replated in the same culture conditions. Colonies of apparently homogenous cells are selectively removed and replated. These cells are consequently expanded and passaged to create a cell line.

Similarly, mouse ES cells are undifferentiated, pluripotent cells derived in vitro from preimplantation embryos (Evans, et al. Nature 292:154–159, 1981; Martin, Proc. Natl. Acad. Sci. USA 78:7634–7638, 1981) or from fetal germ cells (Matsui, et al., Cell 70:841–847, 1992). Mouse ES cells maintain an undifferentiated state through serial passages when cultured in the presence of fibroblast feeder layers in the presence of Leukemia Inhibitory Factor (LIF) (Williams, et al., Nature 336:684–687, 1988). If LIF is removed, mouse ES cells differentiate.

Mouse ES cells cultured in non-attaching conditions aggregate and differentiate into simple embryoid bodies, with an outer layer of endoderm and an inner core of primitive ectoderm. If these embryoid bodies are then allowed to attach onto a tissue culture surface, disorganized differentiation occurs of various cell types, including nerves, blood cells, muscle, and cartilage (Martin, 1981, supra; Doetschman, et al., J. Embryol. Exp. Morph. 87:27–45, 1985). Mouse ES cells injected into syngeneic mice form teratocarcinomas that exhibit disorganized differentiation, often with representatives of all three embryonic germ layers. Mouse ES cells combined into chimeras with normal preimplantation embryos and returned to the uterus participate in normal development (Richard, et al., Cytogenet. Cell Genet. 65:169–171, 1994).

The ability of mouse ES cells to contribute to functional germ cells in chimeras provides a method for introducing site-specific mutations into mouse lines. With appropriate transfection and selection strategies, homologous recombination can be used to derive ES cell lines with planned alterations of specific genes. These genetically altered cells can be used to form chimeras with normal embryos and chimeric animals are recovered. If the ES cells contribute to the germ line in the chimeric animal, then in the next generation a mouse line for the planned mutation is established.

Mouse ES cells can be produced and cultured as described in detail in U.S. Pat. No. 6,190,910. Isolation and culture of primate ES cell lines are described in, e.g., U.S. Pat. No. 6,200,806.

Yet another aspect of the invention provides a method of selecting TH positive cells comprising providing a construct comprising an hTH promoter sequence nucleic acid or a functional fragment thereof operably linked to a nucleic acid encoding a reporter molecule and transfecting a plurality of cells with the construct; differentiating the transfected cells in culture, and subjecting the differentiated cells to a selection procedure.

A number of different differentiation protocols are available to one skilled in the art. For example, stem cells can be differentiated to form different neuronal cell populations as described for mesenchymal stem cells, hematopoetic stem cells, and embryonal stem cells as described in Kopen et al., Proc Natl Acad Sci USA 96:10711–10716, 1999; Sanches-Ramos et al., Exp Neurol 164: 247–256, 2000; Woodbury et al., J Neurosci Res 61:364–370, 2000; Eglitis et al., Proc Natl Acad Sci USA 94:4080–4085, 1997; Mezey et al., Science 290:1779–1782, 2000; Brazelton et al., Science 290:1775–1779, 2000; Reynolds et al., Dev Biol 175:1–13, 1996; Doetsch et al., Cell 97:703–716, 1999; Johansson et al., Cell 96:25–34, 1999; Brustle et al., Science 285:754–756, 1999, Bain et al., Dev Biol 168:324–357, 1995; Strubing et al., Mech Dev 53:275–287, 1995; Li et al., Curr Biol 8:971–974, 1998; Lee et al., Nature Biotechnol 18:675–679, 2000; Kawasaki et al., Neuron 28:31–40, 2000; Slager et al, Dev Genet 14:212–224, 1993; Gottlieb et al., Cells Tissues Organs 165:165–172, 1999; Fraichard et al., J Cell Sci 108:3181–3188, 1995; O'Shea, Anat Rec 257: 32–41, 1999; Liu et al., Proc Natl Acad Sci USA 97:6126–6131, 1999; Weiss et al., J Neurosci 16:7599–7609, 1996.

For example, derivation of dopaminergic (DA) cells from ntES cells performed essentially as described in Wakayama, et al. (Science 292: 740–743, 2001). The method is based on derivation of DA neurons from ES cells, the only difference being that the ES cells used are derived by nuclear transfer. Two protocols have been reported Kawasaki, et al., Induction of midbrain dopaminergic neurons from ES cells by stromal cell-derived inducing activity, in Neuron 28:31–40, 2000; and Lee, et al., in Nature Biotechnology 18:675–679, 2000.; and are reviewed in Hynes, et al. Neuron, 28:11–14, 2000.

In short, ES cells are maintained in the undifferentiated state by growth on gelatin coated surface in the presence of serum and leukemia inhibitory factor (LIF). LIF is withdrawn and the cells are allowed to aggregate and form embryoid bodies in a non-adherent, bacterial petri dish. The cell aggregates are transferred to adherent tissue culture plastic, and expanded in the absence of serum and the presence of insulin, selenium, transferrin and fibronectin. After about 6–10 days induction of DA neurons is accomplished by dissociating the cultures into single cells and plating on a poly-ornithine/laminin substrate in the absence of serum, and with the addition of laminin, basic fibroblast growth factor (bFGF), sonic hedgehog (Shh), and FGF8. After about six days, differentiation to the DA phenotype is accomplished by culture for 6–15 days in the absence of serum. The medium is supplemented during this final stage with: bFGF, Shh, FGF8, laminin, cAMP, and vitamin C.

Alternatively, generation of pancreatic islets from ES cells can be performed, e.g., as described in Lumelsky, et al. (Science, 18 May 2001; 292 (2001) 1389–1394, erratum appears in Science 2001 July 293 (5529):428.). Shortly, ES cells are maintained in the undifferentiated state by growth on gelatin coated surface in the presence of serum and leukemia inhibitory factor (LIF). LIF is withdrawn and the cells are allowed to aggregate and form embryoid bodies in a non-adherent, bacterial petri dish. The cell aggregates are transferred to adherent tissue culture plastic, and expanded in the absence of serum and the presence of insulin, selenium, transferrin and fibronectin. Pancreatic islet progenitors are expanded by growth in N2 medium containing B27 supplement and bFGF. Differentiation and morphogenesis of insulin secreting islet clusters is induced by withdrawing bFGF from above medium and supplementation with nicotinamide.

In one embodiment, the invention provides a method of treating an individual in need thereof with the cells selected using the method of selecting TH positive cells comprising providing a construct comprising an hTH promoter nucleic acid sequence or a functional fragment thereof operably linked to a nucleic acid encoding a reporter molecule and transfecting a plurality of cells with the construct. The transfected cells are thereafter subjected to a selection procedure and the TH positive cells are selected and transplanted to an individual in need thereof.

In another embodiment, the invention provides a method of treating an individual in need thereof with the cells selected using the construct comprising an hTH promoter nucleic acid sequence or a functional fragment thereof operably linked to a nucleic acid encoding reporter molecule and transfecting a plurality of cells with the construct, differentiating the transfected cells in culture and subjecting the differentiated cells to a selection procedure. The selected cells are thereafter transplanted to an individual in need thereof.

The invention further provides a method of treating a subject comprising delivering to a subject a construct comprising an hTH promoter nucleic acid sequence or a functional fragment thereof operably linked to a heterologous nucleic acid sequence encoding a therapeutic protein.

In yet another embodiment, the invention provides a transgenic animal containing a hTH promoter nucleic acid or a functional fragment thereof operably linked to a nucleic acid encoding a reporter molecule.

The present invention also provides transgenic animals and a method of producing transgenic animals that contain within their genome a heterologous nucleic acid sequence under the control of the human tyrosine hydroxylase promoter. Preferably, the animal is a mouse.

"Transgenic" means any cell which includes a DNA sequence which is inserted by artifice into a cell and becomes part of the genome of the organism which develops from that cell or an animal in which a gene has been inactivated by artifice. As used herein, the transgenic organisms are generally transgenic rodents and the DNA (transgene) is inserted by artifice into the nuclear genome or in which a gene has been inactivated.

"Transgene" means any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

More specifically, the present invention provides a construct for the generation of transgenic mice that express, under the control of the human TH promoter, a nucleic acid encoding a reporter molecule in their brain tissue. The present invention also provides transgenic mice carrying the transcript and their offspring as well as cell lines derived from the transgenic mice. The present invention further provides for the use of the transgenic mice in a model to screen for compound that modulate the activity of the TH promoter.

The transgenic mammals are produced as is known in the art. Any method can be used which provides for stable, inheritable, expressible incorporation of the transgene within the nuclear DNA of an animal. These transgenic animals are constructed using standard methods known in the art and as set forth in U.S. Pat. Nos. 5,614,396; 5,487,992; 5,464,764; 5,387,742; 5,347,075; 5,298,422; 5,288,846; 5,221,778; 5,175,384; 5,175,383; 4,873,191; 4,736,866 as well as Burke and Olson [Methods Enzymol. 194:251–70, 1991], Capecchi [Science 244:1288–92, 1989], Lamb et al. [Nat Genet. September; 5(1):22–30, 1993], Schedl et al. [Nucleic Acids Res. October 11; 21(20):4783–7, 1993], Strauss et al. [1993]. Further, patent applications WO 94/23049, WO 93/14200, WO 94/06908, WO 94/28123 also provide information.

More specifically, any techniques known in the art may be used to introduce the transgene into animals, preferably mammals such as a mouse or a pig to produce transgenic lines of animals. Such techniques include, but are not limited to, pronuclear microinjection (U.S. Pat. No. 4,873,191); retrovirus mediated gene transfer into germ lines [Van der Putten et al., 1985]; gene targeting in embryonic stem cells [Thompson et al., 1989 and U.S. Pat. No. 5,614,396]; electroporation of embryos [Lo, 1983]; and sperm-mediated gene transfer [Lavitrano et al., 1989].

Any suitable mammal can be used to produce the mammal carrying a transgene comprising a hTH promoter nucleic acid operably linked to a heterologous nucleic acid sequence described herein. For example, a suitable mammal can be, a mouse (mice), a rat, a rabbit, a pig, a sheep or a cow.

According to techniques well known to those of skill in the art of genetically engineered (e.g., transfected using electroporation or transformed by infection) embryonic stem cells are routinely employed for the production of transgenic non-human embryos. Embryonic stem (ES) cells are pluripotent cells isolated from the inner cell mass of mammalian blastocyst. ES cells can be cultured in vitro under appropriate culture conditions in an undifferentiated state and retain the ability to resume normal in vivo development as a result of being combined with blastocyst and introduced into the uterus of a pseudopregnant foster mother. Those of skill in the art will recognize that various stem cells are known in the art, for example AB-1, HM-1, D3. CC1.2, E-14T62a, RW4 or JI (Teratomacarcinoma and Embryonic Stem Cells: A Practical Approach, E. J. Roberston, ed., IRL Press).

In one embodiment, the hTH -11 kb-Reporter construct is transfected to known human ES cells such as ES cells commercially available from, for example, Geron, Inc., WICell Foundation. The transfection efficiency can be increased by transfecting the ES cells using a minipromoter instead of the full length promoter. This minipromoter comprises preferably one or more of the Concerved Regions described above. Alternatively, episomal expression using an EB based system can be used to express the construct under the hTH promoter of the present invention (Conejero-Goldberg, et al., Experimental. Neurology 2000. February; 161. (2.):453.–61., 161 (2000) 453–461; Lee, et al., Human. Gene Therapy. 12. (8.):945.–953., May 20, 2001. (1 A.D.) 945–953, 2001; Yates, et al., Nature, 313 (812–815).

We believe, that the present invention is the first description of the use of the human TH promoter to allow selection of TH+ living cells. We demonstrate for the first time the sorting and enrichment of TH+ cells which subsequently grow in culture for several days until the experiment was discontinued. The present invention provides a construct which resulted in a signal/noise ratio 2–3 orders of magnitude stronger than what has been described using the rat TH promoter.

In another embodiment, the invention provides a cell line expressing hTH promoter nucleic acid sequence or a functional fragment thereof operably linked to a nucleic acid encoding a reporter.

In a further embodiment the invention provides an assay for screening for agents that affect the function of a hTH promoter or a functional fragment thereof comprising providing a cell line expressing hTH promoter nucleic acid sequence or a functional fragment thereof operably linked to a nucleic acid encoding a reporter molecule, contacting said cell line with a candidate agent and detecting expression of the reporter molecule, wherein increase in the amount of expression of the reporter molecule is indicative of an agent capable of increasing the activity of hTH promoter and decrease in the amount of expression of the reporter sequence is indicative of an agent capable of decreasing the activity of hTH promoter. The cell line may be in vivo or ex vivo.

The candidate agent may be tested individually or as pools of two or more agents. The candidate agent that modulates the activity of hTH promoter can be selected from, e.g., pharmaceutical compounds or a small molecules including organic and inorganic molecules, and unmodified or modified nucleic acids.

In general, novel agents or compounds for modulation of the activity of hTH promoter are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broth, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from, e.g., Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their cell cycle inhibiting or cell cycle inducing activities should be employed whenever possible.

When a crude extract is found to have functional hTH promoter activity increasing or decreasing activities or both, further fractionation of the positive lead extract is necessary to isolate chemical constituents responsible for the observed effect. Thus, the goal of the extraction, fractionation, and purification process is the careful characterization and identification of a chemical entity within the crude extract having hTH promoter inhibiting or hTH promoter inducing activities. The same in vivo and in vitro assays described herein for the detection of activities in mixtures of compounds can be used to purify the active component and to test derivatives thereof. Methods of fractionation and purification of such heterogenous extracts are known in the art. If desired, compounds shown to be useful agents for the treatment of pathogenicity are chemically modified according to methods known in the art. Compounds identified as being of therapeutic value are subsequently analyzed using, e.g. the transgenic mouse of the present invention expressing a reporter gene under the control of the hTH promoter.

Detection of hTH promoter activity can be performed using any number of methods a skilled artisan is knowledgeable of and depend of the type of heterologous reporter protein operably linked to the hTH promoter in the cells. For example, if the cells express green fluorescent promoter under hTH promoter, the level of expression can be simply observed under a fluorescence microscope wherein increase in the activity can be determined by more intense expression of the GFP. Decrease of the hTH activity is readily observed as decrease in the intensity of fluorescence of GFP. Activity is said to be increased if the fluorescence is increased by at least 5%, preferably at least 10%, 20%, 30%, 50%, 100% or more, compared to a control cells wherein no test agent has been applied to. Activity is interpreted as decreased if it is at least 5% less than the control, preferably at least 10% and most preferably about 100%, which is indicated by the point where substantially no fluorescence can be detected. Similar measurements can be made using other reporter molecules.

EXAMPLE

Molecular Cloning of the Human Tyrosine Hydroxylase Promoter.

A partial human tyrosine hydroxylase (hTH) cDNA was purchased from ATCC (ATCC 100604). An EcoRI-Xho I fragment of this cDNA was isolated and used to screen a commercially available lambda cDNA library purchased from Stratagene (catalog no. 936201). The longest hTH cDNA clone of 2 million total plaques screened was isolated and the 5' 350 bp extending from an internal Xho I site to an Eco RI site within the vector was purified for use as a hybridization probe. We screened 3 million plaques of a lambda human genomic library purchased from BIO 101. Of seven positive clones recovered by cre/lox mediated excision in plamid pBSKS+ two contained identical (by restriction mapping) ~15 kb inserts encompassing exons 1,2, and 3 of the hTH gene and 11 kb of 5' flanking (promoter) region as determined by Southern blot analysis.

The proximal 516 bp of the hTH promoter has been previously reported[46]. To sequence the more distal promoter, we isolated an overlapping Not I/SacII 11 kb restriction fragment by electroelution. The promoter is isolated from the vector by agarose gel electrophoresis followed by electroelution. For "shotgun" sequencing this fragment is subjected to titrated ultrasonic shearing to produce an average fragment size of 1.5 kb. After treatment with mung bean nuclease and "polishing" with T4 DNA polymerase, the size range of 1.5–2 kb is isolated by electrophoresis followed by electroelution and ligated into Sma I-cut plasmid pBCKS- (Stratagene). Isolated plasmids are sequenced using the BIGDYE® terminator (cycle sequencing kit) polymerase chain reaction (PCR) sequencing method with ABI PRISM® (sequence detection system) apparatus and software. The resulting data is analyzed and assembled using Lasergene software (DNAstar, Madison, Wis.).

Construction of Plasmid phTH-11 kb-EGFP

Plasmid pMAK 288-12 (=phTH-11 kb-EGFP) places the hTH promoter upstream of the EGFP reporter gene in a manner such that the promoter-reporter cassette can subsequently be isolated from the rest of the vector as an intact 12,007 bp NotI-AflII restriction fragment (SEQ ID NO: 38). Three DNA fragments are ligated to produce plasmid pMAK 288: The distal hTH promoter is isolated as a 10.794 kb NotI-SacII fragment from the original genomic clone pMAK 221-21. The proximal hTH promoter, including the transcription start site, is isolated as a 1.168 kb SacII-KpnI fragment of this insert is cloned into pBSIISK-(Stratagene) to yield pMAK 237. One sequencing primer (pBSII reverse primer, MAKIL 120: ggaaacagctatgaccatg (SEQ ID NO: 23) and one mutagenic primer (MAKIL 119, synthetic BamHI in bold: gacaggatccgggctccgtctccaca; SEQ ID NO: 24) are used to amplify the proximal promoter and add a synthetic BamHI site at position +12 of the 5' untranslated region.

Following cleavage of the PCR product by SacII and BamHI, the 226 bp SacII-BamHI fragment is isolated by electroelution and cloned into SacII-BamHI cut vector pBCKS-(Stratagene) to yield plasmid pMAK 286 (not shown). Electroeluted SacII-BamHI fragment of pMAK 286 is then included in the 288 ligation. The vector and EGFP reporter are provided as a NotI-BamHI fragment of pMAK 285, derived from pEGFP-1 (Clontech) as follows. Unique NotI and XbaI sites were removed sequentially by cleavage, fill-in, re-ligation, and transformation (yielding plasmid pMAK 206). An antibiotic resistance conferring stuffer fragment was constructed by PCR amplification of the chloramphenicol acetyltransferase (CAT) gene from plasmid pBCKS-(Stratagene) using primers containing SmaI (bold) sites: MAKILBC5 (gtcacccgggaccgaataaatacctgtgacg; SEQ ID NO: 25), and MAKIL BC3 (gtcacccgggggatcatatcgtcaattattacc; SEQ ID NO: 26).

The amplimer is cleaved with SmaI and cloned into the SmaI site of pBSIISK-(Stratagene) to yield plasmid construct pMAK 205. The unique BamHI site of this plasmid is removed by Klenow/fill-in to produce pMAK 207. The SacI-EcoRV fragment of pMAK 207 is then isolated and ligated to SacI-SmaI cut pMAK 206. The chloramphenicol/kanamycin double resistant colonies are selected bearing plasmid pMAK 208. The unique Eco0109 site of this construct is removed by cleavage and ligation to a double stranded oligonucleotide (annealed MAKIL 115/MAKIL 116) that destroys the Eco0109 site and contains synthetic sites for I-Ppo I and AflII (the former unique, the latter 1 of 2 in the plasmid): MAKIL 115 (gcCTATGACTCTCTTAAGGTAGCCAAAA; SEQ ID NO: 27) and MAKIL 116 (ggcTTTTGGCTACCTTAAGAGAGTCATA; SEQ ID NO: 28) AflII recognition sequence is in bold.

Figure 4:
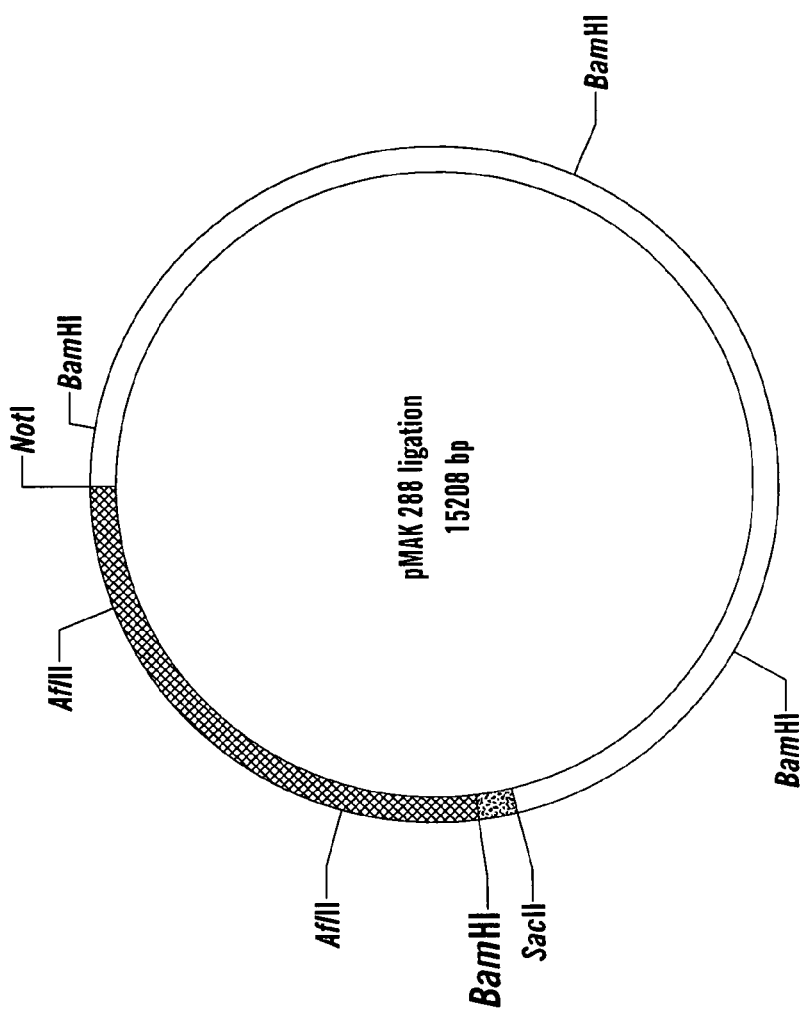
FIG. 4 shows the cloning strategy for hTH transgene in plasmid pMAK 288. The three pieces of DNA are ligated together to yield plasmid pMAK 288. In white is the 10.794 kb distal hTH promoter. In black is the 226 bp semi-synthetic proximal hTH promoter fragment including the synthetic BamHI site. The vector and EGFP reporter are included in the crosshatched region of the upper left quadrant.
Figure 5:
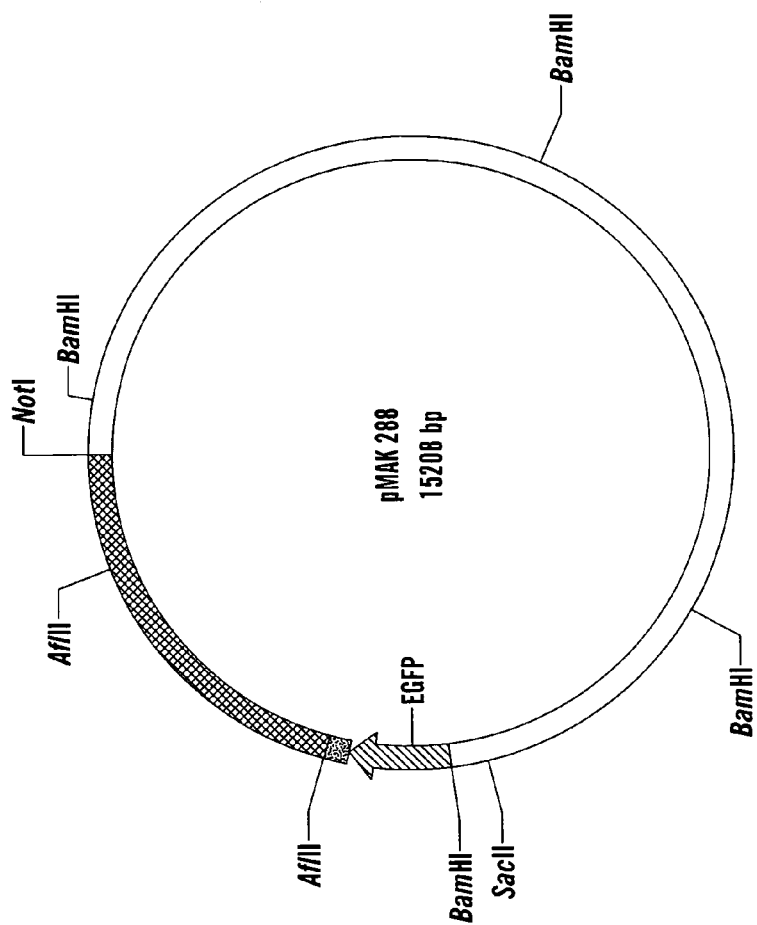
FIG. 5 shows the functional map of cloned hTH-EGFP transgene in plasmid pMAK 288. This figure represents the same plasmid sequence as in FIG. 4, but mapped in functional domains. Again the hTH promoter is in white, extending clockwise from the unique Not I site to the bolded BamHI site. The EGFP reporter is shaded and extends clockwise from the bolded BamHI site through to the arrowhead. The black square symbolized the SV40 polyadenylation sequence. The remaining vector sequences are in crosshatch. For derivation of the transgene, this plasmid was cleaved with NotI and AflII and the larger 12.007 kb fragment isolated by electroelution
Figure 6:
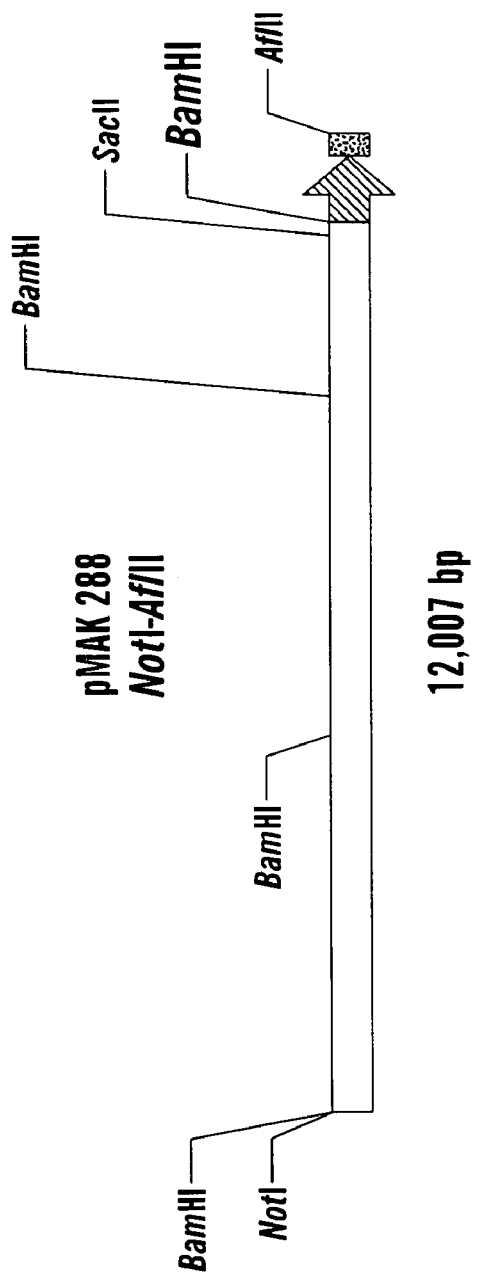
FIG. 6 shows a diagram of the hTH-EGFP transgene used to generate the transgenic mouse. This 12.007 kb NotI-AflII fragment was isolated from plasmid pMAK 288 (FIG. 5), purified, and injected into single-celled embryos for generation of transgenic mice. In this diagram, the hTH promoter is in white, the reporter in crosshatch, and the SV40 polyadenylation sequence in solid black.
Figure 7A:
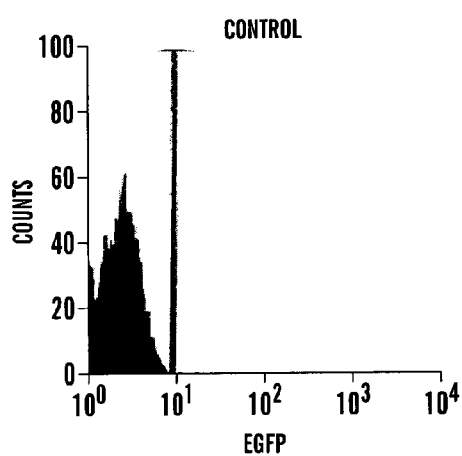
FIGS. 7A–7D show a comparison of the efficiency of the rat TH promoter construct (Sawamoto et al., 2001a) (FIGS. 7A and 7B) to the human TH promoter construct (FIGS. 7C and 7D). The vertical axes, representing the number of cells counted per fluorescence window, have not been scaled to match. It can be seen that in the maximum cell count ranges from 40–60 cells.
Figure 7B:
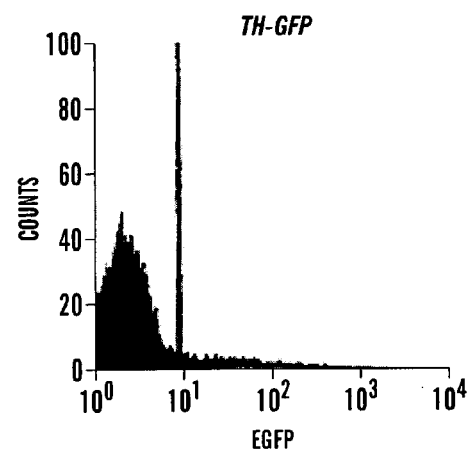
Figure 7C:
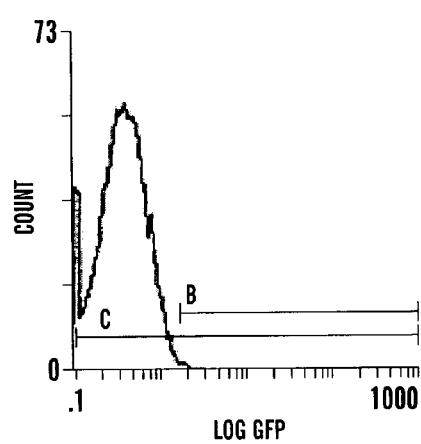
Figure 7D:
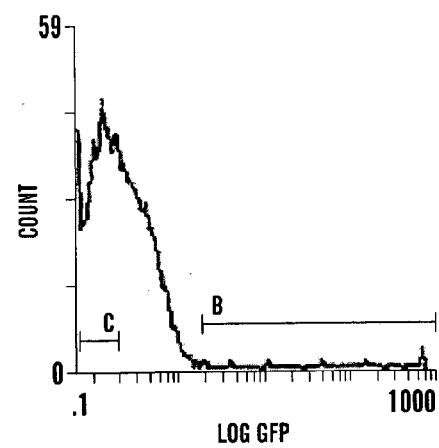
Figure 8A:
FIGS. 8A–8I shows a schematic of a minipromoter.
Figure 8B:
Figure 8C:
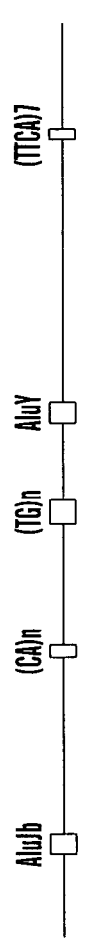
Figure 8D:
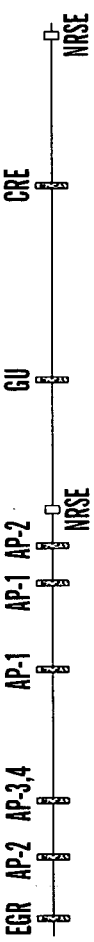
Figure 8E:
Figure 8F:
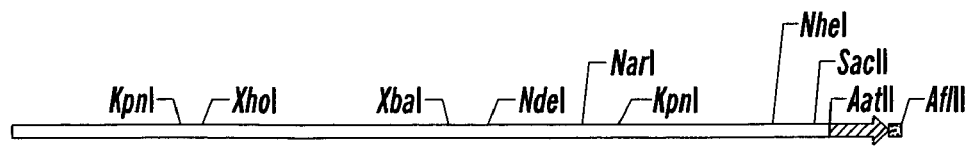
Figure 8G:
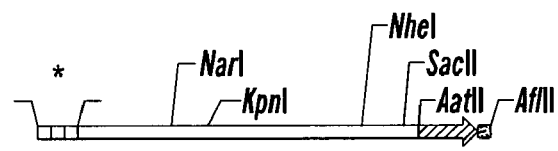
Figure 8H:
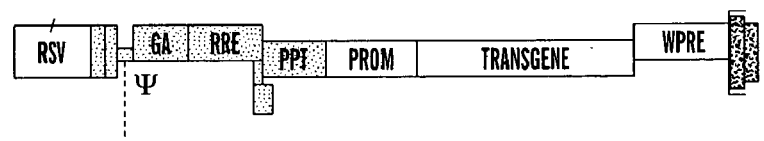
Figure 8I:
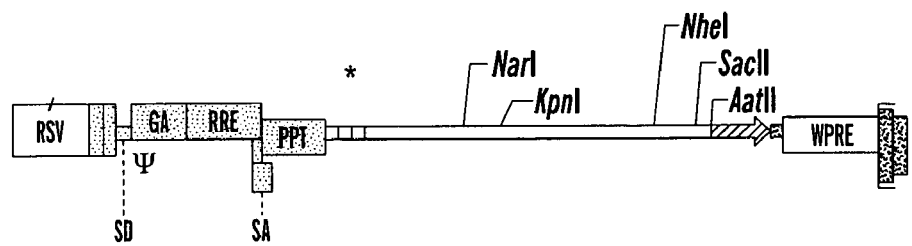
Figure 10B:
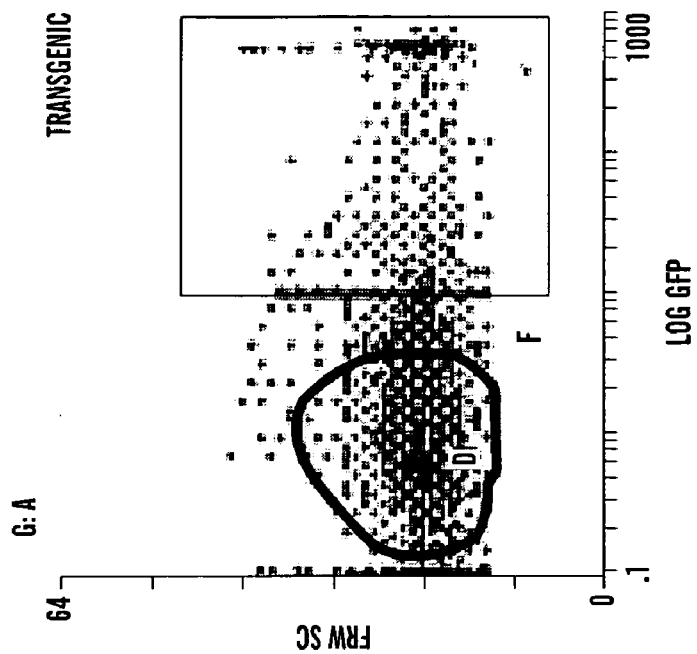
FIGS. 10A and 10B show FACS analysis of a non-transgenic (FIG. 10A) and hTH-11-kb-EGFP transgenic (FIG. 10B) midbrains were dissociated and sorted for GFP fluorescence. The presence of a minor population of highly fluorescent cells can be seen in the transgenic brains only. This population, extending in signal intensity 3 logs above control, was collected and plated in a tissue culture.
Figure 10A:
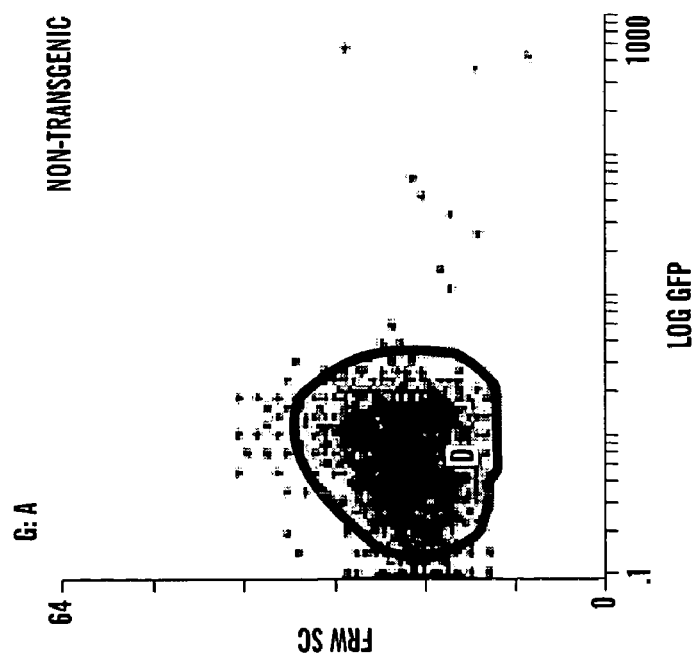

The resulting construct is designated pMAK 285. The larger Not I-BamHI fragment of this plasmid is isolated and included as the vector in the ligation of pMAK 288-12 (see FIGS. 4 and 5). The fusion of the hTH promoter 5' untranslated region to the EGFP reporter is illustrated below with the transcript starting at +1 in uppercase. The synthetic BamHI site is in bold starting at position +12.

The EGFP coding sequence begins at +31 (lower case).

```
                                              (SEQ ID NO:29)
+1         +12         +25      EGFP orf+→
:          :           :        :
AGACGGAGCCCGGATCCACCGGTCGCCACCatggtgagc... ...
```

Construction of Plasmid phTH-11 kb-luc (pMAK 1150-5)

Figure 2:
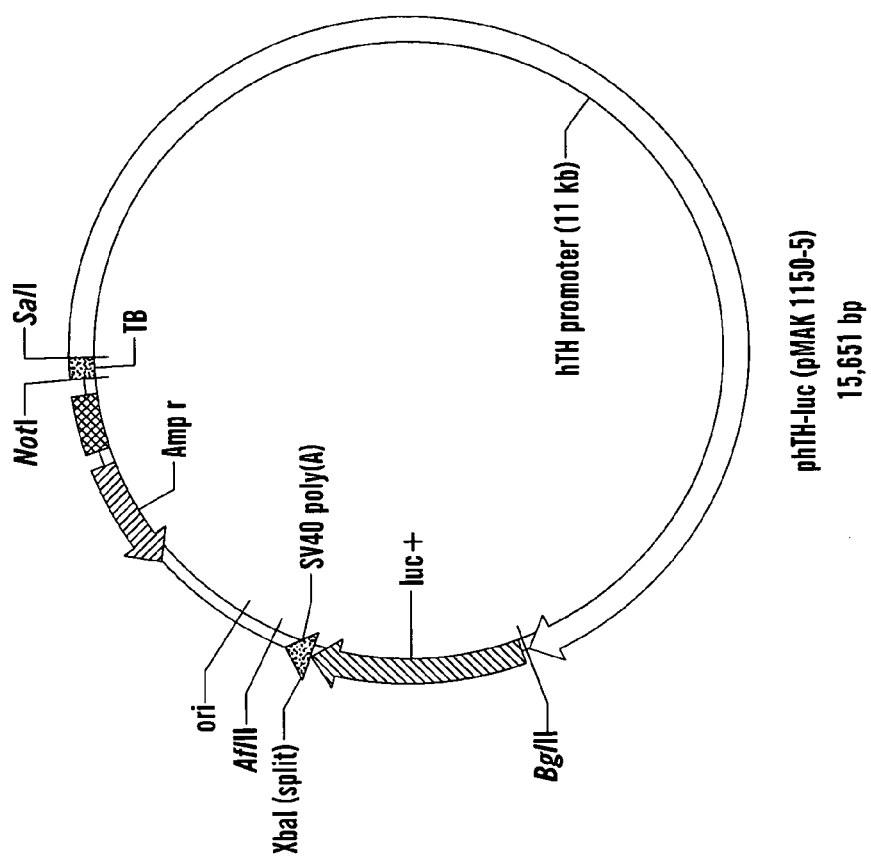
FIG. 2 shows the pMAK 1150-5. The unique sites (Bgl II, Afl II, Sal I and Not I) allow convenient insertion of reporters, introns, and poly(A) cassettes as directionally cloned Bgl II-Afl II fragments. Vector components can be exchanged as Sal I-Afl II or Not I-Afl II pieces.

This hTH-luciferase reporter plasmid is illustrated in FIG. 2 and bears a unique Bgl II site placed within the 5' untranslated region (infra). This allows the isolation of the hTH promoter as a convenient 10.828 kb Sal I/Bgl III cassette (SEQ ID NO: 1) for use with a variety of vectors, as well as a variety of downstream genes, such as, but not limited to, reporter genes. The use of Bgl II does not introduce any unwanted modification(s) to the sequence of hTH promoter. The present invention provides a 10.828 kb hTH promoter sequence wherein this Bgl II is unique. pMAK 1150-5 shows that the unique sites allow convenient insertion of other nucleic acids sequences, for example, reporters, introns, and poly(A) cassettes as directionally cloned Bgl II-Afl II fragments. Similarly, vector components are exchanged as Sal I-Afl II pieces. For all such manipulations it is understood that compatible cohesive ends (eg. BamHI-Bgl II, XhoI-Sal I, or Ava I-Sal I) are also employed as standard procedures of molecular biology.

The plasmid pMAK 237 is mutated by PCR using the T3 sequencing primer and the oligonucleotide GACAGATCTCCGGGCTCCGTCTCCACA MAKIL 124 (SEQ ID NO: 30).

The mutated sequence is isolated as an Aat II-Bgl II fragment and ligated to the larger 10.775 kb Sal I-Aat II 5' promoter fragment isolated from genomic clone pMAK 221-21 to yield the 10.828 kb Sal I-Bgl II sequence.

Outline of the creation of a synthetic Bgl II site in the 5' untranslated region of the human TH gene:

```
                                              (SEQ ID NO:31)
    +1         +10       +20       +30
tgtggAGACGGAGCCCGGACCTCCACACTGAGCCATGC
```

```
                                              (SEQ ID NO:32)
tgtggAGACGGAGCCCGGA GATCTGTC
                    AGATCT
```

```
                                              (SEQ ID NO:33)
       Bgl II    *
   TGTGGAGACGGAGCCCGGA
```

Strategy used for modification of native human tyrosine hydroxylase (hTH) promoter. Only the "top" strand of a portion of the sequence is depicted for ease of alignment. Numbers at top characterize the proximal portion of the hTH transcript that begins with +1. Immediately below is the native hTH sequence with transcribed sequence in CAPS, and translated sequence. Below this is the reverse complement of synthetic oligonucleotide MAKIL 124 used for PCR-mediated mutation. The mutating sequence is in BOLD ITALICS. Note that the mutation creates a Bgl II site (AGATCT) which after digestion (*) yields the final sequence. This unique synthetic Bgl II enables ligation to reporter sequence bearing a compatible cohesive end (e.g. Bgl II, BamHI, Bcl etc.) Note in particular that this mutation leaves unchanged the native sequence of the 5' untranslated region through +14.

The 10,828 bp Sal I-Bgl II modified hTH promoter is assembled by joining the 5' Sal I-Aat II fragment to the 3' Aat II-(synthetic)Bgl II fragment in the vector pMAK 1115. The remainder of the construct hTH-11 kb-luc (pMAK 1150-5) is derived from the commercially available luciferase reporter vector pGL3-basic (Promega Biotech, Madison, Wis.) as follows. The unique Sal I site was changed to a unique Afl II site by insertion of the double stranded oligonucleotide formed by annealing MAKIL 107 and MAKIIL 108 (Afl II in bold:

```
                                 (SEQ ID NO:34)
    TCGAGCCGCCACTTAAGGGTGC          MAKIL 107
```

```
                                 (SEQ ID NO:35)
    TCGAGCACCCTTAAGTGGCGGC          MAKIL 108
```

The unique Kpn I site was changed to a unique Sal I site by insertion of a double stranded oligonucleotide, annealed MAKIL 148/MAKIL 149 (Sal I site in bold):

```
GCATCGTCGACACCGTAC   MAKIL 148   (SEQ ID NO:36)

GGTGTCGACGATGCGTAC   MAKIL 149   (SEQ ID NO:37)
```

Unique BamHI and Xba I sites are eliminated by cutting, Klenow "fill-in," and religation. The final construct is made by ligation of the Sal I-Bgl II hTH promoter from plasmid pMAK 1115 to Sal I-Bgl II cut vector to yield pMAK 1150-5=phTH-11 kb-luc.

Generation of Transgenic Mice

The 12,007 bp NotI AflII restriction fragment from plasmid pMAK 288-12 was isolated by electroelution, precipitated 4× from ethanol/IM ammonium acetate, dried, and resuspended in T.E. buffer. This DNA was microinjected into B6C3F2 single cell embryos which were tranferred to ICR (Taconic, Germantown, N.Y.) pseudopregnant females (Kimmel Cancer Center, Core Transgenic Mouse Facility, Thomas Jefferson University, Jan L. Guz, Transgenic Facility Coordinator, Linda D. Siracusa, Director.) Transgenic pups were identified by Southern blot, using the Not I Afl II fragment as template for the random-primed probe. These founders were mated to the BL6 strain for generation of F1 mice.

B6C3F1's (hybrid of B6×C3) were purchased and mated to each other. This yielded B6C3F2 embryo's which were injected with DNA (288-12). The founders were subsequently mated to B6.

Histology of Transgenic Mice

Immunoperoxidase localization of endogenous TH and the GFP reporter in the basal ganglia of an adult transgenic mouse (founder #7827 line) showed that expression of TH and GFP is highly correlated in the caudate nucleusand substantia nigra.

Further, immunofluorescence localization of endogenous TH and the GFP reporter in the ventral tegmental area and substantia nigra of an adult transgenic mouse (founder #7827 line) showed that the GFP protein was localized with a green FITC conjugate. The merged images revealed extensive co-localization of GFP and TH, about 70% of the TH and GFP signals were co-localized at the anatomic and cellular level.

Analysis of an E12 dissection of transgenic embryonic mesencephalon showed that the function of hTH promoter transgene construct in living tissue and cells resulted in specificity of reporter (EGFP) targeting to TH+ cells.

A tissue sample of mouse encephalon was dissociated with trypsin into a single-cell suspension, plated, and incubated overnight. The 200× image was captured as a single frame by turning up the white light in conjunction with the UV. It demonstrated the high signal/noise ratio of the transgene expression. The brightfield was turned up to clearly visualize the EGFP-negative "background" cells. TH+ neurons were only a small percentage of mesencephalic cells. This image illustrated a corresponding low ratio of EGFP+ to EGFP− (non-fluorescent) cells. The cultures for these analysis were maintained until 48 h after plating, fixed, and processed for double-label fluorescent immunocytochemistry. An image made by merging TH and EGFP images of the cells clearly confirmed the co-expression of TH and the reporter, EGFP.

DAB immunohistochemical analysis of GFP transgene in pancreatic cells of E12 transgenic mouse embryo showed that, in contrast to GFP, which is distributed throughout the cell, TH is cytoplasmic.

Derivation of dopaminergic neurons and pancreatic islet cells from stem cells:

Definitions: ES cell=embryonic stem cell; ntES cell=nuclear transfer embryonic stem cell; neuronal precursor/progenitor cell=general terms for undifferentiated, mitotic cell which may be induced to acquire neuronal characteristics.

Derivation of dopaminergic (DA) cells from ntES cells performed essentially as described in Wakayama, et al. (Science 2001 Apr. 27, 292. (5517.): 740.–3., 292 (1 A.D.) 740–743). The method is based on derivation of DA neurons from ES cells, the only difference being that the ES cells used are derived by nuclear transfer. Two protocols have been reported Kawasaki, et al., Induction of midbrain dopaminergic neurons from ES cells by stromal cell-derived inducing activity, Neuron 2000 Oct. 28, (1.): 31.–40., 28 (2000) 31–40; Lee, et al., Nature Biotechnology 2000 Jun. 18, (6.): 675.–9., 18 (2000) 675–679) and are reviewed in Hynes, et al. Neuron, 2000 Oct. 28, (2000) 11–14).

In short, ES cells are maintained in the undifferentiated state by growth on gelatin coated surface in the presence of serum and leukemia inhibitory factor (LIF). LIF is withdrawn and the cells are allowed to aggregate and form embryoid bodies in a non-adherent, bacterial petri dish. The cell aggregates are transferred to adherent tissue culture plastic, and expanded in the absence of serum and the presence of insulin, selenium, transferrin and fibronectin. After about 6–10 days induction of DA neurons is accomplished by dissociating the cultures into single cells and plating on a poly-ornithine/ lamnin substrate in the absence of serum, and with the addition of lamnin, basic fibroblast growth factor (bFGF), sonic hedgehog (Shh), and FGF8. After about six days, differentiation to the DA phenotype is accomplished by culture for 6–15 days in the absence of serum. The medium is supplemented during this final stage with: bFGF, Shh, FGF8, lamnin, cAMP, and vitamin C.

Generation of pancreatic islets from ES cells is performed as described in Lumelsky, et al. (Science, 2001 May 18, 292 (2001) 1389–1394, erratum appears in Science 2001 July 293 (5529):428.). Shortly, ES cells are maintained in the undifferentiated state by growth on gelatin coated surface in the presence of serum and leukemia inhibitory factor (LIF). LIF is withdrawn and the cells are allowed to aggregate and form embryoid bodies in a non-adherent, bacterial petri dish. The cell aggregates are transferred to adherent tissue culture plastic, and expanded in the absence of serum and the presence of insulin, selenium, transferrin and fibronectin. Pancreatic islet progenitors are expanded by growth in N2 medium containing B27 supplement and bFGF. Differentiation and morphogenesis of insulin secreting islet clusters is induced by withdrawing bFGF from above medium and supplementation with nicotinamide.

Results

Of 93 offspring, 5 tested positive for the transgene by Southern blot of tail DNA (5.4%). These were mated to non-transgenic B6 mice. Thus the 4 transgenic F1 lines we were able to obtain are necessarily heterozygous. We examined single adult individuals of each of these lines by immunocytochemistry for expression of TH and GFP.

Robust transgene expression was detected in most traditional catecholaminergic (CA) tissues with the notable exceptions of the adrenal medulla and locus ceruleus. Conversely, ectopic expression of GFP was detected in a number of regions within the CNS. These include several areas consistently noted by authors employing shorter transgenic constructs derived from rat or human TH: the amygdala, interpeduncular nucleus, nucleus accumbens, and septum.

We used line F1-09 (founder #7827) for examination of TH+ cells of the adult and embryonic nigro-striatal pathway. We compared the expression of endogenous TH and the GFP reporter within the caudate nucleus (CN, A, B) and substantia nigra (SN, C, D) of an adult transgenic mouse DAB immunohistochemistry reveals close anatomical correlation between TH and GFP both in the cell bodies of the substantia nigra and their axonal projections to the caudate nucleus. GFP autoflourescence may be sensitive to fixatives and mounting agents. [7] However, a strong reporter signal is retained in PLP-fixed tissue and preserved for months in slides stored in the dark at 4° C. In a further study of TH-GFP coexpression using dual-label immunofluorescence, the GFP protein is detected with a FITC conjugate yielding a green signal, while a rhodamine signal marks the expression of TH in red coexpression of TH and GFP both in neuronal cell bodies and efferent fibers was indicated by the yellow signal in the merged image. A correlation of >80% was determined for TH and GFP with a slight excess of singly-labeled GFP+ cells.

A 40× brightfield image of a dissected E13 transgenic embryonic mouse midbrain was analyzed. The neural tube was opened longitudinally along the dorsal surface and was oriented with the anterior midbrain at the bottom of the frame. The same field, imaged by GFP fluorescence which showed strong signal within the isthmus was easily distinguished from the surrounding tissue. This has practical significance as it is possible to pick transgenic midbrains by eye, using an inverted fluorescent microscope, and the GFP signal can guide further dissection. Thus far the yield of E13 transgenics per pregnancy has been indistinguishable from 50% implying that the transgene is not toxic, at least in heterozygotes. Pooled GFP-labeled isthmi were dissociated with trypsin to a single cell suspension and plated on polyornithine coated 8-well chamber slides. We examined the cultures for morphology and retention of the GFP signal by inverted brightfield and fluorescence microscopy after incubation overnight. To indicate the number of GFP+ cells among the total dissociated population, the image was captured as a single frame with both UV and brightfield illumination. The GFP+ cells represent a small minority of the cells. Within 18 h of plating they have begun to elaborate processes which distinguish them morphologically from the majority of small round cells. This network of processes continued to grow over the lifetime of the cultures, 4 days. One set of cultures was fixed after 2 days and examined for TH/GFP co-expression by dual label immunofluorescence microscopy. A single field was labeled for TH, or GFP. The yellow signal in the merged image indicated near complete correlation between the two, although, individual GFP+ singly-labeled cells could be detected.

We have demonstrated that 11 kb of the human tyrosine hydroxylase promoter is capable of driving reporter gene expression to dopaminergic sites of the embryonic and adult CNS. In particular, the strong levels of GFP flourescence in the embryonic substantia nigra permits ready identification of TH+ cells suitable for transplant. This implies that this construct may be clinically useful for deriving material for cell replacement therapy of Parkinson's disease. Protocols have been reported for the derivation of human dopaminergic cells from embryonic stem (ES) cells and expandable human neural precursors[9; 24; 25; 30; 57; 71; 74]. However, in all cases the final yield of TH+ cells is quite low. The hTH-GFP reporter construct reported here may thus be of use for final purification of therapeutic cells from such renewable sources. Indeed, successful amelioration of behavioral deficits by transplant of FACS purified embryonic DA neurons has recently been describes by Okano and colleagues using a rodent model of Parkinson's disease[59]. These authors used a GFP reporter driven by 9 kb of the rat TH promoter.

Ectopic expression of the reporter in our transgenic mice showed some parallels to that described in other models using shorter fragments of rat or human TH promoter. These authors have consistently noted expression in the amygdala, interpeduncular nucleus, nucleus accumbens, and septum[33; 40; 44; 70]. Some of this ectopic expression may be ascribed to positional effects dependent on the site of integration of the transgene. However these consistent observations suggest a role for sequences within the transgene. One possibility is that the 11 kb hTH promoter is lacking repressor elements which may lie beyond this region[70]. Another possibility amenable to experiment is that gene dosage could titrate out repressors that define the anatomical limits of normal expression. The surprising failure of TH promoter-driven expression which we observed within the adrenal medulla and locus ceruleus has been noted before in experiments utilizing a 5.3 kb fragment of the rat TH promoter[70]. In that case it was possible to ascribe this anomaly to instability of the reporter in those tissues. The lacZ reporter construct utilized contained a polyadenylation signal from SV40, but not a splice site, similar to the GFP reporter (EGFP-1, Clontech). Thus, although not wishing to be bound by a theory, the relatively rapid turnover of mRNA in amygdala and locus ceruleus may account for these observations (Alterio et al., Id.:296).

The availability of our murine transgenic model enables the design of future genetic, biochemical, and functional studies to examine this issue.

To genetically tag living embryonic dopaminergic cells which can be purified using FACS for use in cell replacement therapies to treat Parkinson's disease we dissected mesencephalons from 52 hTH/GFP transgene-positive E13 mouse embryos (of 126 total embryos). The neural tube was opened longitudinally along the dorsal surface and ventral portion containing the brightly fluorescent GFP+ DA neurons was isolated. Pooled ventral midbrains were dissociated with trypsin to a single cell suspension. Cells were then analyzed and sorted by FACS.

Fluorescence analysis (FIG. 7) revealed a population of cells with fluorescence signal intensity 3.5 logs above baseline. These cells represented 13.6% ($2.3 \times 10^6$) of the 17 million cells collected. When this group of cells was sorted, we recovered $1.2 \times 10^6$ GFP$^+$ cells and $7.9 \times 10^5$ GFP$^-$ cells.

Cells were plated on polyornithine coated 8-well chambers slides and examined for the retention of the GFP signal by inverted brightfield and fluorescence microscopy after incubation in culture overnight. Cultures plated from the GFP− cell population were indeed devoid of fluorescent cells the following day. In cultures derived from the GFP+ cell population, approximately 75% of total cells fluoresced brightly from endogenous green GFP signal. While this represents n enormous enrichment, as compared with the usual 1–5% cells that is present in unsorted midbrain cultures, it is believed that by re-sorting the cells a second time before plating in culture, it will be possible next time to achieve a near total purification of GFP+ cells. By 16 hours in culture, GFP+ cells had elaborated a neuritic plexus. One set of cultures was fixed after 36 hours and examined for TH/GFP coexpression by dual label immunoflourescence microscopy. We found a complete overlap in the cells which expressed endogenous TH and those that expressed the transgene GFP, indicating that sorting DA neurons to near purity based on their expression of the GFP reporter gene enables recovery of purified DA neurons for the use in cell transplantation for Parkinson's Disease.

REFERENCES

1. Altschul, S. F., Gish, W., Miller, W., Myers, E. W. and Lipman, D. J., Basic local alignment search tool, *Journal of Molecular Biology*, 215 (1990) 403–410.
2. Anonymous, A unified nomenclature system for the nuclear receptor superfamily, *Cell*, 97 (1999) 161–163.
3. Aubin, J., Lemieux, M., Tremblay, M., Behringer, R. R. and Jeannotte, L., Transcriptional interferences at the Hoxa4/Hoxa5 locus: importance of correct Hoxa5 expression for the proper specification of the axial skeleton, *Developmental Dynamics*, 212 (1998) 141–156.
4. Baffi, J. S., Palkovits, M., Castillo, S. O., Mezey, E. and Nikodem, V. M., Differential expression of tyrosine hydroxylase in catecholaminergic neurons of neonatal wild-type and Nurr1-deficient mice, *Neuroscience*, 93 (1999) 631–642.
5. Buervenich, S., Carmine, A., Arvidsson, M., Xiang, F., Zhang, Z., Sydow, O., Jonsson, E. G., Sedvall, G. C., Leonard, S., Ross, R. G., Freedman, R., Chowdari, K. V., Nimgaonkar, V. L., Perlmann, T., Anvret, M. and Olson, L., NURR1 mutations in cases of schizophrenia and manic-depressive disorder, *American Journal of Medical Genetics*, 2000 Dec. 4, 96 808–813.
6. Buscher, D., Bosse, B., Heymer, J. and Ruther, U., Evidence for genetic control of Sonic hedgehog by Gli3 in mouse limb development, *Mechanisms.of.Development*, 62 (1997) 175–182.
7. Chalfie, M., Green fluorescent protein. [Review] [42 refs], *Photochemistry.& Photobiology.*, 62 (1995) 651–656.
8. Craig, S. P., Buckle, V. J., Lamouroux, A., Mallet, J. and Craig, I., Localization of the human tyrosine hydroxylase gene to 11p15: gene duplication and evolution of metabolic pathways, *Cytogenetics.& Cell Genetics*, 42 (1986) 29–32.
9. Daadi, M. M. and Weiss, S., Generation of tyrosine hydroxylase-producing neurons from precursors of the embryonic and adult forebrain f, *Journal of Neuroscience*, 19 (1999) 4484–4497.
10. Driever, W. and Nusslein-Volhard, C., The bicoid protein determines position in the Drosophila embryo in a concentration-dependent manner, *Cell*, 54 (1988) 95–104.
11. Drouin, J., Lamolet, B., Lamonerie, T., Lanctot, C. and Tremblay, J. J., The PTX family of homeodomain transcription factors during pituitary developments. [Review] [16 refs], *Molecular & Cellular Endocrinology*, 140 (1998) 31–36.
12. Du, X. and Iacovitti, L., Multiple signaling pathways direct the initiation of tyrosine hydroxylase gene expression in cultured brain neurons, *Brain Research.Molecular.Brain Research*, 50 (1997) 1–8.
13. German, M. S., Wang, J., Chadwick, R. B. and Rutter, W. J., Synergistic activation of the insulin gene by a LIM-homeo domain protein and a basic helix-loop-helix protein: building a functional insulin minienhancer complex, *Genes & Development*, 6 (1992) 2165–2176.
14. Ghosh, D., TFD: the transcription factors database, *Nucleic.Acids.Research.*, 20 Suppl (1992) 2091–2093.
15. Giguere, V., Orphan nuclear receptors: from gene to function. [Review] [639 refs], *Endocrine Reviews*, 20 (1999) 689–725.
16. Hobert, O. and Westphal, H., Functions of LIM-homeobox genes. [Review] [78 refs], *Trends in Genetics*, 2000 Feb. 16, (2000) 75–83.
17. Homer, M. A., Quintin, S., Domeier, M. E., Kimble, J., Labouesse, M. and Mango, S. E., pha-4, an HNF-3 homolog, specifies pharyngeal organ identity in *Caenorhabditis elegans*, *Genes & Development*, 12 (1998) 1947–1952.
18. Hynes, M., Porter, J. A., Chiang, C., Chang, D., Tessier-Lavigne, M., Beachy, P. A. and Rosenthal, A., Induction of midbrain dopaminergic neurons by Sonic hedgehog, *Neuron*, 15 (1995) 35–44.
19. Hynes, M. and Rosenthal, A., Specification of dopaminergic and serotonergic neurons in the vertebrate CNS. [Review] [85 refs], *Current Opinion in Neurobiology*, 9 (1999) 26–36.
20. Iler, N., Rowitch, D. H., Echelard, Y., McMahon, A. P. and Abate-Shen, C., A single homeodomain binding site restricts spatial expression of Wnt-1 in the developing brain, *Mechanisms of Development*, 53 (1995) 87–96.
21. Kaneda, N., Kobayashi, K., Ichinose, H., Kishi, F., Nakazawa, A., Kurosawa, Y., Fujita, K. and Nagatsu, T., Isolation of a novel cDNA clone for human tyrosine hydroxylase: alternative RNA splicing produces four kinds of mRNA from a single gene, *Biochemical & Biophysical Research Communications*, 146 (1987) 971–975.
22. Karlsson, O., Thor, S., Norberg, T., Ohlsson, H. and Edlund, T., Insulin gene enhancer binding protein Isl-1 is a member of a novel class of proteins containing both a homeo- and a Cys-His domain, *Nature*, 344 (1990) 879–882.
23. Kawai, S. and Sugiura, T., Characterization of human bone morphogenetic protein (BMP)-4 and -7 gene promoters: activation of BMP promoters by Gli, a sonic hedgehog mediator, *Bone* 2001 Jul. 29, (1.):54.–61., 29 (2001) 54–61.
24. Kawasaki, H., Mizuseki, K., Nishikawa, S., Kaneko, S., Kuwana, Y., Nakanishi, S., Nishikawa, S. I. and Sasai, Y., Induction of midbrain dopaminergic neurons from ES cells by stromal cell-derived inducing activity, *Neuron* Oct. 2000 28, (1.):31.–40., 28 31–40.
25. Kawasaki, H., Suemori, H., Mizuseki, K., Watanabe, K., Urano, F., Ichinose, H., Haruta, M., Takahashi, M., Yoshikawa, K., Nishikawa, S. I., Nakatsuji, N. and Sasai, Y., Generation of dopaminergic neurons and pigmented epithelia from primate ES cells by stromal cell-derived inducing activity, *Proceedings of the National Academy of Sciences of the United States of America*, 99 (2002) 1580–1585.
26. Kinzler, K. W., Bigner, S. H., Bigner, D. D., Trent, J. M., Law, M. L., O'Brien, S. J., Wong, A. J. and Vogelstein, B., Identification of an amplified, highly expressed gene in a human glioma, *Science*, 236 (1987) 70–73.
27. Kuziora, M. A. and McGinnis, W., Autoregulation of a Drosophila homeotic selector gene, *Cell*, 55 (1988) 477–485.
28. Lebel, M., Gauthier, Y., Moreau, A. and Drouin, J., Pitx3 activates mouse tyrosine hydroxylase promoter via a high-affinity binding site, *Journal. of. Neurochemistry.* 77.(2.):558.–567., 2001 April 558–567, 2001.
29. Lee, J., Platt, K. A., Censullo, P. and Ruiz, Gli1 is a target of Sonic hedgehog that induces ventral neural tube development, *Development*, 124 (1997) 2537–2552.

30. Lee, S. H., Lumelsky, N., Studer, L., Auerbach, J. M. and McKay, R. D., Efficient generation of midbrain and hindbrain neurons from mouse embryonic stem cells, *Nature Biotechnology* 2000 Jun. 18. (6.):675.–9., 18 675–679.
31. LeMotte, P. K., Kuroiwa, A., Fessler, L. I. and Gehring, W. J., The homeotic gene Sex Combs Reduced of Drosophila: gene structure and embryonic expression, *EMBO Journal*, 8 (1989) 219–227.
32. Litingtung, Y. and Chiang, C., Specification of ventral neuron types is mediated by an antagonistic interaction between Shh and Gli3, *Nature Neuroscience*, 2000 Oct. 3, (2000) 979–985.
33. Liu, J., Merlie, J. P., Todd, R. D. and O'Malley, K. L., Identification of cell type-specific promoter elements associated with the rat tyrosine hydroxylase gene using transgenic founder analysis, *Brain Research.Molecular. Brain Research.*, 50 (1997) 33–42.
34. Lonnerberg, P., Schoenherr, C. J., Anderson, D. J. and Ibanez, C. F., Cell type-specific regulation of choline acetyltransferase gene expression. Role of the neuron-restrictive silencer element and cholinergic-specific enhancer sequences, *Journal of Biological Chemistry*, 271 (1996) 33358–33365.
35. Lubon, H. and Hennighausen, L., Nuclear proteins from lactating mammary glands bind to the promoter of a milk protein gene, *Nucleic Acids Research*, 15 (1987) 2103–2121.
36. Mahaffey, J. W. and Kaufman, T. C., Distribution of the Sex combs reduced gene products in Drosophila melanogaster, *Genetics*, 117 (1987) 51–60.
37. McGinnis, W., Jack, T., Chadwick, R., Regulski, M., Bergson, C., McGinnis, N. and Kuziora, M. A., Establishment and maintenance of position-specific expression of the Drosophila homeotic selector gene Deformed. [Review] [71 refs], *Advances in Genetics*, 27 (1990) 363–402.
38. Meloni, R., Albanese, V., Ravassard, P., Treilhou, F. and Mallet, J., A tetranucleotide polymorphic microsatellite, located in the first intron of the tyrosine hydroxylase gene, acts as a transcription regulatory element in vitro, *Human. Molecular.Genetics*, 7 (1998) 423–428.
39. Milbrandt, J., Nerve growth factor induces a gene homologous to the glucocorticoid receptor gene, *Neuron*, 1 (1988) 183–188.
40. Min, N., Joh, T. H., Kim, K. S., Peng, C. and Son, J. H., 5' upstream DNA sequence of the rat tyrosine hydroxylase gene directs high-level and tissue-specific expression to catecholaminergic neurons in the central nervous system of transgenic mice, *Brain Research.Molecular.Brain Research.*, 27 (1994) 281–289.
41. Miwa, K. and Strominger, J. L., The HLA-DQ beta gene upstream region contains an immunoglobulin-like octamer motif that binds cell-type specific nuclear factors, *Nucleic Acids Research*, 15 (1902) 8057–8067.
42. Morello, R., Zhou, G., Dreyer, S. D., Harvey, S. J., Ninomiya, Y., Thorner, P. S., Miner, J. H., Cole, W., Winterpacht, A., Zabel, B., Oberg, K. C. and Lee, B., Regulation of glomerular basement membrane collagen expression by LMX1B contributes to renal disease in nail patella syndrome, *Nature Genetics*, 2001 Feb. 27, (2001) 205–208.
43. Murphy, E. P. and Conneely, O. M., Neuroendocrine regulation of the hypothalamic pituitary adrenal axis by the nurr1/nur77 subfamily of nuclear receptors, *Molecular.Endocrinology*, 11 (1997) 39–47.
44. 44 Nagatsu, I., Karasawa, N., Yamada, K., Sakai, M., Fujii, T., Takeuchi, T., Arai, R., Kobayashi, K. and Nagatsu, T., Expression of human tyrosine hydroxylase-chloramphenicol acetyltransferase (CAT) fusion gene in the brains of transgenic mice as examined by CAT immunocytochemistry, *Journal.of.Neural Transmission.—General.Section.*, 96 (1994) 85–104.
45. Nagatsu, T., Levitt, M. and Udenfriend, S., Tyrosine Hydroxylase, The Initial Step in Norepinephrine Biosynthesis, *Journal of Biological Chemistry*, 239 (1964) 2910–2917.
46. O'Malley, K. L., Anhalt, M. J., Martin, B. M., Kelsoe, J. R., Winfield, S. L. and Ginns, E. I., Isolation and characterization of the human tyrosine hydroxylase gene: identification of 5' alternative splice sites responsible for multiple mRNAs, *Biochemistry*, 26 (1987) 2910–2914.
47. Packer, A. I., Crotty, D. A., Elwell, V. A. and Wolgemuth, D. J., Expression of the murine Hoxa4 gene requires both autoregulation and a conserved retinoic acid response element, *Development*, 125 (1998) 1991–1998.
48. Perlmann, T. and Jansson, L., A novel pathway for vitamin A signaling mediated by RXR heterodimerization with NGFI-B and NURR1, *Genes & Development*, 9 (1995) 769–782.
49. Peverali, F. A., D'Esposito, M., Acampora, D., Bunone, G., Negri, M., Faiella, A., Stomaiuolo, A., Pannese, M., Migliaccio, E. and Simeone, A., Expression of HOX homeogenes in human neuroblastoma cell culture lines, *Differentiation*, 45 (1990) 61–69.
50. Philips, A., Lesage, S., Gingras, R., Maira, M. H., Gauthier, Y., Hugo, P. and Drouin, J., Novel dimeric Nur77 signaling mechanism in endocrine and lymphoid cells, *Molecular & Cellular Biology*, 17 (1997) 5946–5951.
51. Powell, J. F., Boni, C., Lamouroux, A., Craig, I. W. and Mallet, J., Assignment of the human tyrosine hydroxylase gene to chromosome 11, *FEBS Letters.*, 175 (1984) 37–40.
52. Prestridge, D. S., SIGNAL SCAN: a computer program that scans DNA sequences for eukaryotic transcriptional elements, *Computer.Applications.in the.Biosciences.*, 7 (1991) 203–206.
53. Riddle, R. D., Johnson, R. L., Laufer, E. and Tabin, C., Sonic hedgehog mediates the polarizing activity of the ZPA, *Cell*, 75 (1993) 1401–1416.
54. Roelink, H., Porter, J. A., Chiang, C., Tanabe, Y., Chang, D. T., Beachy, P. A. and Jessell, T. M., Floor plate and motor neuron induction by different concentrations of the amino-terminal cleavage product of sonic hedgehog autoproteolysis, *Cell*, 81 (1995) 445–455.
55. Ruppert, J. M., Vogelstein, B. and Kinzler, K. W., The zinc finger protein GLI transforms primary cells in cooperation with adenovirus EIA, *Molecular & Cellular Biology*, 11 (1991) 1724–1728.
56. Sacchetti, P., Mitchell, T. R., Granneman, J. G. and Bannon, M. J., Nurr1 enhances transcription of the human dopamine transporter gene through a novel mechanism, *Journal.of.Neurochemistry.* 76.(5.):1565.–1572., March 2001, 1565–1572, 2001.
57. Sanchez-Pernaute, R., Studer, L., Bankiewicz, K. S., Major, E. O. and McKay, R. D., In vitro generation and transplantation of precursor-derived human dopamine neurons, *Journal.of.Neuroscience Research.* 2001 Aug. 15, 65.(4.):284.–8., 65 284–288.
58. Saucedo-Cardenas, O., Quintana-Hau, J. D., Le, W. D., Smidt, M. P., Cox, J. J., De Mayo, F., Burbach, J. P. and Conneely, O. M., Nurr1 is essential for the induction of the dopaminergic phenotype and the survival of ventral mesencephalic late dopaminergic precursor neurons, *Pro-* ceedings.of.the.National.Academy.of.Sciences.of.the. United.States.of.America., 95 (1998) 4013–4018.
59. Sawamoto, K., Nakao, N., Kobayashi, K., Matsushita, N., Takahashi, H., Kakishita, K., Yamamoto, A., Yoshizaki, T., Terashima, T., Murakami, F., Itakura, T. and Okano, H., Visualization, direct isolation, and transplantation of midbrain dopaminergic neurons, Proceedings.of.the.National.Academy.of.Sciences.of.the.United. States.of.America. 98.(11.):64 23.–6428., 2001 May 22, (1 A.D.) 6423–6428, 2001.
60. Schimmel, J. J., Crews, L., Roffler-Tarlov, S. and Chikaraishi, D. M., 4.5 kb of the rat tyrosine hydroxylase 5 ' flanking sequence directs tissue specific expression during development and contains consensus sites for multiple transcription factors, Molecular.Brain Research. 74.(1.–2.): 1.–14., (1999)
61. Schoenherr, C. J., Paquette, A. J. and Anderson, D. J., Identification of potential target genes for the neuron-restrictive silencer factor, Proceedings of the National Academy of Sciences of the United States of America, 93 (1996) 9881–9886.
62. Scott, M. P., Vertebrate homeobox gene nomenclature, Cell, 71 (1992) 551–553.
63. Simeone, A., Acampora, D., Gulisano, M., Stornaiuolo, A. and Boncinelli, E., Nested expression domains of four homeobox genes in developing rostral brain. [see comments.], Nature, 358 (1992) 687–690.
64. Simeone, A., Acampora, D., Nigro, V., Faiella, A., D'Esposito, M., Stomaiuolo, A., Mavilio, F. and Boncinelli, E., Differential regulation by retinoic acid of the homeobox genes of the four HOX loci in human embryonal carcinoma cells, Mechanisms of Development, 33 (1991) 215–227.
65. Smidt, M. P., Asbreuk, C. H., Cox, J. J., Chen, H., Johnson, R. L. and Burbach, J. P., A second independent pathway for development of mesencephalic dopaminergic neurons requires Lmx1b, Nature Neuroscience, 2000 Apr. 3, (2000) 337–341.
66. Smidt, M. P., van Schaick, H. S., Lanctot, C., Tremblay, J. J., Cox, J. J., van der Kleij, A. A., Wolterink, G., Drouin, J. and Burbach, J. P., A homeodomain gene Ptx3 has highly restricted brain expression in mesencephalic dopaminergic neurons, Proceedings.of.the.National. Academy.of.Sciences.of.the.United.States.of.America., 94 (1997) 13305–13310.
67. Smit, A. F. A. and Green, P., 2002, (UnPub)
68. Stull, N. D., Jung, J. W. and lacovitti, L., Induction of a dopaminergic phenotype in cultured striatal neurons by bone morphogenetic proteins, Brain Research.Developmental Brain Research, 2001 Sep. 23, 130 (2001) 91–98.
69. Tornqvist, N., Hermanson, E., Perlmann, T. and Stromberg, I., Generation of tyrosine hydroxylase-immunoreactive neurons in ventral mesencephalic tissue of Nurr1 deficient mice, Dev.Brain Research, 133 (2002) 37–47.
70. Trocme, C., Sarkis, C., Hermel, J. M., Duchateau, R., Harrison, S., Simonneau, M., Al-Shawi, R. and Mallet, J., CRE and TRE sequences of the rat tyrosine hydroxylase promoter are required for TH basal expression in adult mice but not in the embryo, European.Journal.of.Neuroscience, 10 (1998) 508–521.
71. Wakayama, T., Tabar, V., Rodriguez, I., Perry, A. C., Studer, L. and Mombaerts, P., Differentiation of embryonic stem cell lines generated from adult somatic cells by nuclear transfer. [see comments], Science 2001 Apr. 27, 292.(5517.):740.–3., 292 (1 A.D.) 740–743.
72. Wilson, T. E., Fahrner, T. J., Johnston, M. and Milbrandt, J., Identification of the DNA binding site for NGFI-B by genetic selection in yeast, Science, 252 (1991) 1296–1300.
73. Wingender, E., Chen, X., Fricke, E., Geffers, R., Hehl, R., Liebich, I., Krull, M., Matys, V., Michael, H., Ohnhauser, R., Pruss, M., Schacherer, F., Thiele, S. and Urbach, S., The TRANSFAC system on gene expression regulation, Nucleic Acids Research, 2001 Jan. 1, 29 281–283.
74. Zhang, S. C., Wernig, M., Duncan, I. D., Brustle, O. and Thomson, J. A., In vitro differentiation of transplantable neural precursors from human embryonic stem cells. [see comments.], Nature Biotechnology, 2001 Dec. 19, (2001) 1129–1133.
75. Albanese,V., Biguet,N. F., Kiefer,H., Bayard,E., Mallet, J., and Meloni,R. (2001). Quantitative effects on gene silencing by allelic variation at a tetranucleotide microsatellite. Human Molecular Genetics 10, 1785–1792.
76. Ghosh,D. (1992). TFD: the transcription factors database. Nucleic. Acids. Research. 20 Suppl, 2091–2093.
77. Lebel,M., Gauthier,Y., Moreau,A., and Drouin,J. (2001). Pitx3 activates mouse tyrosine hydroxylase promoter via a high-affinity binding site. Journal of Neurochemistry 77, 558–567.
78. Lubon,H. and Hennighausen,L. (1987). Nuclear proteins from lactating mammary glands bind to the promoter of a milk protein gene. Nucleic Acids Research 15, 2103–2121.
79. Meloni,R., Albanese,V., Ravassard,P., Treilhou,F., and Mallet,J. (1998). A tetranucleotide polymorphic microsatellite, located in the first intron of the tyrosine hydroxylase gene, acts as a transcription regulatory element in vitro. Human Molecular Genetics 7, 423–428.
80. Miwa,K. and Strominger,J. L. (1987). The HLA-DQ beta gene upstream region contains an immunoglobulin-like octamer motif that binds cell-type specific nuclear factors. Nucleic Acids Research 15, 8057–8067.
81. Morello,R., Zhou,G., Dreyer,S. D., Harvey,S. J., Ninomiya,Y., Thorner,P. S., Miner,J. H., Cole,W., Winterpacht,A., Zabel,B., Oberg,K. C., and Lee,B. (2001). Regulation of glomerular basement membrane collagen expression by LMX1B contributes to renal disease in nail patella syndrome. Nature Genetics 27, 205–208.
82. Philips,A., Lesage,S., Gingras,R., Maira,M. H., Gauthier,Y., Hugo,P., and Drouin,J. (1997). Novel dimeric Nur77 signaling mechanism in endocrine and lymphoid cells. Molecular & Cellular Biology 17, 5946–5951.
83. Prestridge,D. S. (1991). SIGNAL SCAN: a computer program that scans DNA sequences for eukaryotic transcriptional elements. Computer. Applications. in the. Biosciences. 7, 203–206.
84. Schoenherr,C. J., Paquette,A. J., and Anderson,D. J. (1996). Identification of potential target genes for the neuron-restrictive silencer factor. Proceedings of the National Academy of Sciences of the United States of America 93, 9881–9886.
85. Wingender,E., Chen,X., Fricke,E., Geffers,R., Hehl,R., Liebich,I., Krull,M., Matys,V., Michael,H., Ohnhauser,R., Pruss,M., Schacherer,F., Thiele,S., and Urbach,S. (2001). The TRANSFAC system on gene expression regulation. Nucleic Acids Research 29, 281–283.

The references cited herein and throughout the specification are herein incorporated by reference in their entirety.

The invention claimed is:

1. The isolated human tyrosine hydroxylase promoter nucleic acid sequence of SEQ ID NO:1.

2. A nucleic acid construct comprising a human tyrosine hydroxylase promoter sequence of SEQ ID NO: 1 operably linked to a heterologous nucleic acid sequence.

3. The construct of claim 2, wherein the heterologous nucleic acid sequence encodes a reporter molecule.

4. The construct of claim 3, wherein the reporter molecule is a fluorescent protein.

5. The construct of claim 2, wherein the heterologous nucleic acid sequence encodes a protein.

6. The construct of claim 5, wherein the protein is selected from the group consisting of a glial cell derived neurotrophic factor, superoxide dismutase, fibroblast growth factor, and brain derived neurotrophic factor.

* * * * *